(12) United States Patent
Kyhse-Andersen

(10) Patent No.: US 9,376,463 B2
(45) Date of Patent: Jun. 28, 2016

(54) DUAL AFFINITY POLYPEPTIDES FOR PURIFICATION

(71) Applicant: CHRETO ApS, Værløse (DK)

(72) Inventor: Jan Kyhse-Andersen, Værløse (DK)

(73) Assignee: CHRETO ApS, Værløse (DK)

( * ) Notice: Subject to any disclaimer, the term of this patent is extended or adjusted under 35 U.S.C. 154(b) by 182 days.

(21) Appl. No.: 14/086,621

(22) Filed: Nov. 21, 2013

(65) Prior Publication Data

US 2014/0081001 A1    Mar. 20, 2014

Related U.S. Application Data

(63) Continuation of application No. 12/740,940, filed as application No. PCT/EP2008/065346 on Nov. 12, 2008, now abandoned.

(30) Foreign Application Priority Data

Nov. 12, 2007 (EP) .................................... 07120454

(51) Int. Cl.
*C07K 1/22* (2006.01)

(52) U.S. Cl.
CPC ....................................... *C07K 1/22* (2013.01)

(58) Field of Classification Search
None
See application file for complete search history.

(56) References Cited

U.S. PATENT DOCUMENTS

| | | | |
|---|---|---|---|
| 5,169,936 A | 12/1992 | Staples | |
| 5,328,985 A | 7/1994 | Sano | |
| 2007/0218535 A1 | 9/2007 | Lin | |
| 2007/0224620 A1 | 9/2007 | Hartzell | |
| 2008/0108053 A1 | 5/2008 | Patchornik | |

FOREIGN PATENT DOCUMENTS

| | | |
|---|---|---|
| EP | 0962771 A1 | 12/1999 |
| EP | 1529844 A2 | 5/2005 |
| WO | 97/09068 A2 | 3/1997 |
| WO | 97/19957 A1 | 6/1997 |
| WO | WO8809344 * | 12/1998 |
| WO | 01/53325 A2 | 7/2001 |
| WO | 01/95857 A2 | 12/2001 |
| WO | 2005/047317 A1 | 5/2005 |
| WO | WO 2006059904 A1 * | 6/2006 |
| WO | 2008/28218 A1 | 3/2008 |
| WO | 2009/062942 A2 | 5/2009 |

OTHER PUBLICATIONS

Arbabi-Ghahroudi et al. "Prokaryotic expression of antibodies" Cancer and Metastasis Reviews 24: 501-519, 2005.*
Ford et al, "Fusion Tails for the Recovery and Purification of Recombinant Proteins", Protein Expression and Purification, vol. 2, pp. 95-107 (1991).
Hammarbergh et al., Proc. Natl. Acad. Sci, USA, vol. 86, pp. 4367-4371 (1989).
Hytonen et al., "Dual Affinity Avidin Molecules", Proteins: Structure, Function and Bioinformatics, vol. 61, pp. 597-607 (2005).
Janson and Ryden, Protein Purification: Principles, high-Resolution, Methods and Applications, 2nd Ed. (1998).
Linder et al. Biotechnology and Bioengineering, vol. 60, No. 5, pp. 642-647 (1998).
Nygrel et al., "Immunochemistry at Interfaces", Immunology, vol. 66, pp. 321-327 (1989).
Rigaut et al., "A Generic Protein Purification Method for Protein Complex Characterization and Proteom Exploration", Nature Biotechnology, vol. 17, pp. 1030-1032 (1991).
Sano et al., "A Streptavidin-Protein A Chimera that Allows One-Step Production of a Variety of Specific Antibody Conjugates", Biotechnology, vol. 9, pp. 1378-1381 (1991).
Shinagawa et al., "Purification of staphylococcal enterotoxins A and E by immunoaffinity chromatography using a murine monoclonal antibody with dual specificity for both of these toxins", Journal of Immunological Methods, vol. 139, No. 1, pp. 49-53 (1991).
Shpigel et al., "Expression, purification and application of Staphylococcal Protein A fused to cellulose-binding domain", Biotechnology Appl. Biochemistry, vol. 31, pp. 197-203 (2000).
Wilchek and Gorecki, "A New Approach for isolation of Biologically Active Compounds by Affinity Chromatography: Isolation of Trypsin", FEBS Letters, vol. 31, No. 1, pp. 149-152(1973).
Kindermann et al., "Covalent and Selective Immobilization of Fusion Proteins", J Am Chem Soc 125, 7810-7811 (2003).

* cited by examiner

*Primary Examiner* — Daniel E Kolker
*Assistant Examiner* — James Rogers
(74) *Attorney, Agent, or Firm* — McHale & Slavin, P.A.

(57) ABSTRACT

The present invention relates to a process for purification of a target biomolecule, comprising the steps: (a) contacting (i) a target biomolecule, (ii) a dual affinity polypeptide, and (iii) a solid support comprising a catching ligand, wherein the ratio between the equilibrium dissociation constants of the dual affinity polypeptide, $[K_{D,t}/K_{D,s}]$, is at least $10^0$ at standard conditions; and (b) recovering the target biomolecule by elution.

19 Claims, No Drawings

SEQUENCE LISTING

```
<160> NUMBER OF SEQ ID NOS: 39

<210> SEQ ID NO 1
<211> LENGTH: 972
<212> TYPE: DNA
<213> ORGANISM: Artificial Sequence
<220> FEATURE:
<223> OTHER INFORMATION: fusion protein coding sequence

<400> SEQUENCE: 1
ggatccacca tgaaggcgat cctctctctc gctgccgcgc tcttgagcgc cgcgcccgcg      60
ttctcgaccg cagtctgggg ccagtgcggt ggcatcggct tctccggcga caccacgtgc     120
accgcttcca cctgcgtgaa ggtcaacgac tactactcgc agtgccagcc tggcgcgtcc     180
gcacccacgt caaccgcctc cgcgcccggc ccgtccgcgt gcccttttggt gaagcgtcag    240 gtgcagttgc aggaatcggg tggaggactc gtgcaggcag gtggctcgct ccggttgtcg     300
tgtgcagcct cgggcagggc gacatcggga catggccatt acggtatggg atggttccgc     360
caggtgcctg gaaaggaacg agaattcgtc gcagccatcc ggtggtccgg caaagagacc     420
tggtacaaag attcggtgaa aggacggttc accatctcca gggataacgc gaaaactact     480
gtctacctcc agatgaactc gctcaagccc gaggatacga cagtgtatta ctgtgccgca     540
aggcctgtcc gagtggacga catctcgctc cccgtgggtt tcgattactg gggacagggt     600
acgcaggtga cggtctcctc cgataacaaa ttcaacaagg aacagcagaa cgcgttctac     660
gagatcttgc acctccccaa cctcaacgag gaacagagga acgtttcat tcagtcgctc     720 aaggacgacc cctcccagtc cgccaacctc ttggcagaag ccaagaagtt gaacgatgca     780
caggcaccga aagacaacaa gttcaacaaa gagcagcaga acgccttcta tgagatcttg     840
catctcccga acttgaacga ggagcagcgg aacggcttca tccagtcctt gaaagatgat     900
ccctcgcagt cggccaacct cctcgcagaa gcgaagaagc tcaacgacgc gcaggcacct     960
aagtgactcg ag                                                        972

<210> SEQ ID NO 2
<211> LENGTH: 318
<212> TYPE: PRT
<213> ORGANISM: Artificial Sequence
<220> FEATURE:
<223> OTHER INFORMATION: fusion protein
```

<400> SEQUENCE: 2

```
Met Lys Ala Ile Leu Ser Leu Ala Ala Leu Leu Ser Ala Ala Pro
1               5                   10                  15

Ala Phe Ser Thr Ala Val Trp Gly Gln Cys Gly Gly Ile Gly Phe Ser
                20                  25                  30

Gly Asp Thr Thr Cys Thr Ala Ser Thr Cys Val Lys Val Asn Asp Tyr
                35                  40                  45

Tyr Ser Gln Cys Gln Pro Gly Ala Ser Ala Pro Thr Ser Thr Ala Ser
            50                  55                  60

Ala Pro Gly Pro Ser Ala Cys Pro Leu Val Lys Arg Gln Val Gln Leu
65                  70                  75                  80

Gln Glu Ser Gly Gly Gly Leu Val Gln Ala Gly Gly Ser Leu Arg Leu
                85                  90                  95

Ser Cys Ala Ala Ser Gly Arg Ala Thr Ser Gly His Gly His Tyr Gly
                100                 105                 110

Met Gly Trp Phe Arg Gln Val Pro Gly Lys Glu Arg Glu Phe Val Ala
            115                 120                 125

Ala Ile Arg Trp Ser Gly Lys Glu Thr Trp Tyr Lys Asp Ser Val Lys
130                 135                 140

Gly Arg Phe Thr Ile Ser Arg Asp Asn Ala Lys Thr Thr Val Tyr Leu
145                 150                 155                 160

Gln Met Asn Ser Leu Lys Pro Glu Asp Thr Ala Val Tyr Tyr Cys Ala
                165                 170                 175

Ala Arg Pro Val Arg Val Asp Asp Ile Ser Leu Pro Val Gly Phe Asp
            180                 185                 190

Tyr Trp Gly Gln Gly Thr Gln Val Thr Val Ser Ser Asp Asn Lys Phe
        195                 200                 205

Asn Lys Glu Gln Gln Asn Ala Phe Tyr Glu Ile Leu His Leu Pro Asn
    210                 215                 220

Leu Asn Glu Glu Gln Arg Asn Gly Phe Ile Gln Ser Leu Lys Asp Asp
225                 230                 235                 240

Pro Ser Gln Ser Ala Asn Leu Leu Ala Glu Ala Lys Lys Leu Asn Asp
                245                 250                 255

Ala Gln Ala Pro Lys Asp Asn Lys Phe Asn Lys Glu Gln Gln Asn Ala
            260                 265                 270

Phe Tyr Glu Ile Leu His Leu Pro Asn Leu Asn Glu Glu Gln Arg Asn
        275                 280                 285

Gly Phe Ile Gln Ser Leu Lys Asp Asp Pro Ser Gln Ser Ala Asn Leu
    290                 295                 300

Leu Ala Glu Ala Lys Lys Leu Asn Asp Ala Gln Ala Pro Lys
305                 310                 315
```

<210> SEQ ID NO 3
<211> LENGTH: 261
<212> TYPE: PRT
<213> ORGANISM: Artificial Sequence
<220> FEATURE:
<223> OTHER INFORMATION: fusion protein

<400> SEQUENCE: 3

```
Met Lys Ala Ile Leu Ser Leu Ala Ala Leu Leu Ser Ala Ala Pro
1               5                   10                  15

Ala Phe Ser Thr Ala Val Trp Gly Gln Cys Gly Gly Ile Gly Phe Ser
                20                  25                  30

Gly Asp Thr Thr Cys Thr Ala Ser Thr Cys Val Lys Val Asn Asp Tyr
```

```
                   35                  40                  45
Tyr Ser Gln Cys Gln Pro Gly Ala Ser Ala Pro Thr Ser Thr Ala Ser
 50                  55                  60

Ala Pro Gly Pro Ser Ala Cys Pro Leu Val Lys Arg Gln Val Gln Leu
 65                  70                  75                  80

Gln Glu Ser Gly Gly Gly Leu Val Gln Ala Gly Gly Ser Leu Arg Leu
                 85                  90                  95

Ser Cys Ala Ala Ser Gly Arg Ala Thr Ser Gly His Gly His Tyr Gly
                100                 105                 110

Met Gly Trp Phe Arg Gln Val Pro Gly Lys Glu Arg Glu Phe Val Ala
            115                 120                 125

Ala Ile Arg Trp Ser Gly Lys Glu Thr Trp Tyr Lys Asp Ser Val Lys
        130                 135                 140

Gly Arg Phe Thr Ile Ser Arg Asp Asn Ala Lys Thr Thr Val Tyr Leu
145                 150                 155                 160

Gln Met Asn Ser Leu Lys Pro Glu Asp Thr Ala Val Tyr Tyr Cys Ala
                165                 170                 175

Ala Arg Pro Val Arg Val Asp Asp Ile Ser Leu Pro Val Gly Phe Asp
            180                 185                 190

Tyr Trp Gly Gln Gly Thr Gln Val Thr Val Ser Ser Asp Asn Lys Phe
        195                 200                 205

Asn Lys Glu Gln Gln Asn Ala Phe Tyr Glu Ile Leu His Leu Pro Asn
210                 215                 220

Leu Asn Glu Glu Gln Arg Asn Gly Phe Ile Gln Ser Leu Lys Asp Asp
225                 230                 235                 240

Pro Ser Gln Ser Ala Asn Leu Leu Ala Glu Ala Lys Lys Leu Asn Asp
                245                 250                 255

Ala Gln Ala Pro Lys
            260

<210> SEQ ID NO 4
<211> LENGTH: 469
<212> TYPE: DNA
<213> ORGANISM: Artificial Sequence
<220> FEATURE:
<223> OTHER INFORMATION: fusion protein coding sequence

<400> SEQUENCE: 4
cacctcgtgg ccgagtatcg tggctactgg cggcaccact acgacggcta ccccactgg     60 atcaggcagc gtgacctcga ccagcaagac caccgcgact gctagcaaga ccagcaccga    120
taacaaattc aacaaggaac agcagaacgc gttctacgag atcttgcacc tccccaacct    180
caacgaggaa cagaggaacg gtttcattca gtcgctcaag gacgacccct cccagtccgc    240
caacctcttg gcagaagcca agaagttgaa cgatgcacag gcaccgaaag acaacaagtt    300
caacaaagag cagcagaacg ccttctatga gatcttgcat ctcccgaact tgaacgagga    360
gcagcggaac ggcttcatcc agtccttgaa agatgatccc tcgcagtcgg ccaacctcct    420
cgcagaagcg aagaagctca acgacgcgca ggcacctaag tgactcgag               469

<210> SEQ ID NO 5
<211> LENGTH: 77
<212> TYPE: DNA
<213> ORGANISM: Artificial Sequence
<220> FEATURE:
<223> OTHER INFORMATION: adaptor sequence

<400> SEQUENCE: 5
```
cgcgcttgga aatcacattt gccaaccctg tgcagacgag gccgctcagg gcgagtagag    60
atcggaacga catggtg                                                  77

<210> SEQ ID NO 6
<211> LENGTH: 77
<212> TYPE: DNA
<213> ORGANISM: Artificial Sequence
<220> FEATURE:
<223> OTHER INFORMATION: adaptor sequence

<400> SEQUENCE: 6
gatccaccat gtcgttccga tctctactcg ccctgagcgg cctcgtctgc acagggttgg    60
caaatgtgat tccaag                                                   77

<210> SEQ ID NO 7
<211> LENGTH: 639
<212> TYPE: PRT
<213> ORGANISM: Artificial Sequence
<220> FEATURE:
<223> OTHER INFORMATION: fusion protein

<400> SEQUENCE: 7

```
Met Ser Phe Arg Ser Leu Leu Ala Leu Ser Gly Leu Val Cys Thr Gly
1               5                   10                  15
Leu Ala Asn Val Ile Ser Lys Arg Ala Thr Leu Asp Ser Trp Leu Ser
            20                  25                  30
Asn Glu Ala Thr Val Ala Arg Thr Ala Ile Leu Asn Asn Ile Gly Ala
        35                  40                  45
Asp Gly Ala Trp Val Ser Gly Ala Asp Ser Gly Ile Val Val Ala Ser
    50                  55                  60
Pro Ser Thr Asp Asn Pro Asp Phe Tyr Thr Trp Thr Arg Asp Ser Gly
65                  70                  75                  80
Leu Val Leu Lys Thr Leu Val Asp Leu Phe Arg Asn Gly Asp Thr Ser
                85                  90                  95
Leu Leu Ser Thr Ile Glu Asn Tyr Ile Ser Ala Gln Ala Ile Val Gln
            100                 105                 110
Gly Ile Ser Asn Pro Ser Gly Asp Leu Ser Ser Gly Ala Gly Leu Gly
        115                 120                 125
Glu Pro Lys Phe Asn Val Asp Glu Thr Ala Tyr Thr Gly Ser Trp Gly
    130                 135                 140
Arg Pro Gln Arg Asp Gly Pro Ala Leu Arg Ala Thr Ala Met Ile Gly
145                 150                 155                 160
Phe Gly Gln Trp Leu Leu Asp Asn Gly Tyr Thr Ser Thr Ala Thr Asp
                165                 170                 175
Ile Val Trp Pro Leu Val Arg Asn Asp Leu Ser Tyr Val Ala Gln Tyr
            180                 185                 190
Trp Asn Gln Thr Gly Tyr Asp Leu Trp Glu Glu Val Asn Gly Ser Ser
        195                 200                 205
Phe Phe Thr Ile Ala Val Gln His Arg Ala Leu Val Glu Gly Ser Ala
    210                 215                 220
Phe Ala Thr Ala Val Gly Ser Ser Cys Ser Trp Cys Asp Ser Gln Ala
225                 230                 235                 240
Pro Glu Ile Leu Cys Tyr Leu Gln Ser Phe Trp Thr Gly Ser Phe Ile
                245                 250                 255
Leu Ala Asn Phe Asp Ser Ser Arg Ser Gly Lys Asp Ala Asn Thr Leu
            260                 265                 270
```

```
Leu Gly Ser Ile His Thr Phe Asp Pro Glu Ala Ala Cys Asp Asp Ser
        275                 280                 285

Thr Phe Gln Pro Cys Ser Pro Arg Ala Leu Ala Asn His Lys Glu Val
    290                 295                 300

Val Asp Ser Phe Arg Ser Ile Tyr Thr Leu Asn Asp Gly Leu Ser Asp
305                 310                 315                 320

Ser Glu Ala Val Ala Val Gly Arg Tyr Pro Glu Asp Thr Tyr Tyr Asn
                325                 330                 335

Gly Asn Pro Trp Phe Leu Cys Thr Leu Ala Ala Ala Glu Gln Leu Tyr
                340                 345                 350

Asp Ala Leu Tyr Gln Trp Asp Lys Gln Gly Ser Leu Glu Val Thr Asp
            355                 360                 365

Val Ser Leu Asp Phe Phe Lys Ala Leu Tyr Ser Asp Ala Ala Thr Gly
        370                 375                 380

Thr Tyr Ser Ser Ser Ser Ser Thr Tyr Ser Ser Ile Val Asp Ala Val
385                 390                 395                 400

Lys Thr Phe Ala Asp Gly Phe Val Ser Ile Val Glu Thr His Ala Ala
                405                 410                 415

Ser Asn Gly Ser Met Ser Glu Gln Tyr Asp Lys Ser Asp Gly Glu Gln
                420                 425                 430

Leu Ser Ala Arg Asp Leu Thr Trp Ser Tyr Ala Ala Leu Leu Thr Ala
            435                 440                 445

Asn Asn Arg Arg Asn Ser Val Val Pro Ala Ser Trp Gly Glu Thr Ser
450                 455                 460

Ala Ser Ser Val Pro Gly Thr Cys Ala Ala Thr Ser Ala Ile Gly Thr
465                 470                 475                 480

Tyr Ser Ser Val Thr Val Thr Ser Trp Pro Ser Ile Val Ala Thr Gly
                485                 490                 495

Gly Thr Thr Thr Thr Ala Thr Pro Thr Gly Ser Gly Ser Val Thr Ser
                500                 505                 510

Thr Ser Lys Thr Thr Ala Thr Ala Ser Lys Thr Ser Thr Asp Asn Lys
        515                 520                 525

Phe Asn Lys Glu Gln Gln Asn Ala Phe Tyr Glu Ile Leu His Leu Pro
        530                 535                 540

Asn Leu Asn Glu Glu Gln Arg Asn Gly Phe Ile Gln Ser Leu Lys Asp
545                 550                 555                 560

Asp Pro Ser Gln Ser Ala Asn Leu Leu Ala Glu Ala Lys Lys Leu Asn
                565                 570                 575

Asp Ala Gln Ala Pro Lys Asp Asn Lys Phe Asn Lys Glu Gln Gln Asn
            580                 585                 590

Ala Phe Tyr Glu Ile Leu His Leu Pro Asn Leu Asn Glu Glu Gln Arg
            595                 600                 605

Asn Gly Phe Ile Gln Ser Leu Lys Asp Asp Pro Ser Gln Ser Ala Asn
        610                 615                 620

Leu Leu Ala Glu Ala Lys Lys Leu Asn Asp Ala Gln Ala Pro Lys
625                 630                 635

<210> SEQ ID NO 8
<211> LENGTH: 583
<212> TYPE: PRT
<213> ORGANISM: Artificial Sequence
<220> FEATURE:
<223> OTHER INFORMATION: fusion protein

<400> SEQUENCE: 8
```

-continued

```
Met Ser Phe Arg Ser Leu Leu Ala Leu Ser Gly Leu Val Cys Thr Gly
1               5                  10                 15

Leu Ala Asn Val Ile Ser Lys Arg Ala Thr Leu Asp Ser Trp Leu Ser
            20                 25                 30

Asn Glu Ala Thr Val Ala Arg Thr Ala Ile Leu Asn Asn Ile Gly Ala
        35                 40                 45

Asp Gly Ala Trp Val Ser Gly Ala Asp Ser Gly Ile Val Val Ala Ser
50                 55                 60

Pro Ser Thr Asp Asn Pro Asp Tyr Phe Tyr Thr Trp Thr Arg Asp Ser
65                 70                 75                 80

Gly Leu Val Leu Lys Thr Leu Val Asp Leu Phe Arg Asn Gly Asp Thr
                85                 90                 95

Ser Leu Leu Ser Thr Ile Glu Asn Tyr Ile Ser Ala Gln Ala Ile Val
            100                105                110

Gln Gly Ile Ser Asn Pro Ser Gly Asp Leu Ser Ser Gly Ala Gly Leu
        115                120                125

Gly Glu Pro Lys Phe Asn Val Asp Glu Thr Ala Tyr Thr Gly Ser Trp
130                135                140

Gly Arg Pro Gln Arg Asp Gly Pro Ala Leu Arg Ala Thr Ala Met Ile
145                150                155                160

Gly Phe Gly Gln Trp Leu Leu Asp Asn Gly Tyr Thr Ser Thr Ala Thr
                165                170                175

Asp Ile Val Trp Pro Leu Val Arg Asn Asp Leu Ser Tyr Val Ala Gln
            180                185                190

Tyr Trp Asn Gln Thr Gly Tyr Asp Leu Trp Glu Glu Val Asn Gly Ser
        195                200                205

Ser Phe Phe Thr Ile Ala Val Gln His Arg Ala Leu Val Glu Gly Ser
210                215                220

Ala Phe Ala Thr Ala Val Gly Ser Ser Cys Ser Trp Cys Asp Ser Gln
225                230                235                240

Ala Pro Glu Ile Leu Cys Tyr Leu Gln Ser Phe Trp Thr Gly Ser Phe
                245                250                255

Ile Leu Ala Asn Phe Asp Ser Ser Arg Ser Gly Lys Asp Ala Asn Thr
            260                265                270

Leu Leu Gly Ser Ile His Thr Phe Asp Pro Glu Ala Ala Cys Asp Asp
        275                280                285

Ser Thr Phe Gln Pro Cys Ser Pro Arg Ala Leu Ala Asn His Lys Glu
290                295                300

Val Val Asp Ser Phe Arg Ser Ile Tyr Thr Leu Asn Asp Gly Leu Ser
305                310                315                320

Asp Ser Glu Ala Val Ala Val Gly Arg Tyr Pro Glu Asp Thr Tyr Tyr
                325                330                335

Asn Gly Asn Pro Trp Phe Leu Cys Thr Leu Ala Ala Ala Glu Gln Leu
            340                345                350

Tyr Asp Ala Leu Tyr Gln Trp Asp Lys Gln Gly Ser Leu Glu Val Thr
        355                360                365

Asp Val Ser Leu Asp Phe Phe Lys Ala Leu Tyr Ser Asp Ala Ala Thr
370                375                380

Gly Thr Tyr Ser Ser Ser Ser Ser Thr Tyr Ser Ser Ile Val Asp Ala
385                390                395                400

Val Lys Thr Phe Ala Asp Gly Phe Val Ser Ile Val Glu Thr His Ala
                405                410                415
```

```
Ala Ser Asn Gly Ser Met Ser Glu Gln Tyr Asp Lys Ser Asp Gly Glu
            420                 425                 430

Gln Leu Ser Ala Arg Asp Leu Thr Trp Ser Tyr Ala Ala Leu Leu Thr
        435                 440                 445

Ala Asn Asn Arg Arg Asn Ser Val Val Pro Ala Ser Trp Gly Glu Thr
    450                 455                 460

Ser Ala Ser Ser Val Pro Gly Thr Cys Ala Ala Thr Ser Ala Ile Gly
465                 470                 475                 480

Thr Tyr Ser Ser Val Thr Val Thr Ser Trp Pro Ser Ile Val Ala Thr
                485                 490                 495

Gly Gly Thr Thr Thr Thr Ala Thr Pro Thr Gly Ser Gly Ser Val Thr
            500                 505                 510

Ser Thr Ser Lys Thr Thr Ala Thr Ala Ser Lys Thr Ser Thr Asp Asn
        515                 520                 525

Lys Phe Asn Lys Glu Gln Gln Asn Ala Phe Tyr Glu Ile Leu His Leu
    530                 535                 540

Pro Asn Leu Asn Glu Glu Gln Arg Asn Gly Phe Ile Gln Ser Leu Lys
545                 550                 555                 560

Asp Asp Pro Ser Gln Ser Ala Asn Leu Leu Ala Glu Ala Lys Lys Leu
                565                 570                 575

Asn Asp Ala Gln Ala Pro Lys
            580
```

<210> SEQ ID NO 9
<211> LENGTH: 259
<212> TYPE: PRT
<213> ORGANISM: Artificial Sequence
<220> FEATURE:
<223> OTHER INFORMATION: fusion protein

<400> SEQUENCE: 9

```
Met Lys Ala Ile Leu Ser Leu Ala Ala Ala Leu Leu Ser Ala Ala Pro
1               5                   10                  15

Ala Phe Ser Thr Ala Val Trp Gly Gln Cys Gly Gly Ile Gly Phe Ser
            20                  25                  30

Gly Asp Thr Thr Cys Thr Ala Ser Thr Cys Val Lys Val Asn Asp Tyr
        35                  40                  45

Tyr Ser Gln Cys Gln Pro Gly Ala Ser Ala Pro Thr Ser Thr Ala Ser
    50                  55                  60

Ala Pro Gly Pro Ser Ala Cys Pro Gly Ser Asp Asn Lys Phe Asn Lys
65                  70                  75                  80

Glu Gln Gln Asn Ala Phe Tyr Glu Ile Leu His Leu Pro Asn Leu Asn
                85                  90                  95

Glu Glu Gln Arg Asn Gly Phe Ile Gln Ser Leu Lys Asp Asp Pro Ser
            100                 105                 110

Gln Ser Ala Asn Leu Leu Ala Glu Ala Lys Lys Leu Asn Asp Ala Gln
        115                 120                 125

Ala Pro Lys Asp Asn Lys Phe Asn Lys Glu Gln Gln Asn Ala Phe Tyr
    130                 135                 140

Glu Ile Leu His Leu Pro Asn Leu Asn Glu Glu Gln Arg Asn Gly Phe
145                 150                 155                 160

Ile Gln Ser Leu Lys Asp Asp Pro Ser Gln Ser Ala Asn Leu Leu Ala
                165                 170                 175

Glu Ala Lys Lys Leu Asn Asp Ala Gln Ala Pro Lys Ser Ser Ser Thr
            180                 185                 190
```

```
Ser Ser Pro Val Asn Gln Pro Thr Ser Thr Thr Ser Thr Ser
        195                 200                 205

Thr Thr Ser Ser Pro Pro Val Gln Pro Thr Thr Pro Ser Gly Cys Thr
210                 215                 220

Ala Glu Arg Trp Ala Gln Cys Gly Gly Asn Gly Trp Ser Gly Cys Thr
225                 230                 235                 240

Thr Cys Val Ala Gly Ser Thr Cys Thr Lys Ile Asn Asp Trp Tyr His
                245                 250                 255

Gln Cys Leu
```

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
gcaagggatg ccatgcttgg                                          20

<210> SEQ ID NO 11
<211> LENGTH: 38
<212> TYPE: DNA
<213> ORGANISM: Artificial Sequence
<220> FEATURE:
<223> OTHER INFORMATION: Primer

<400> SEQUENCE: 11
cttgttgaat ttgttatccg agccagggca cgcggacg                      38

<210> SEQ ID NO 12
<211> LENGTH: 38
<212> TYPE: DNA
<213> ORGANISM: Artificial Sequence
<220> FEATURE:
<223> OTHER INFORMATION: Primer

<400> SEQUENCE: 12
cgtccgcgtg ccctggctcg gataacaaat tcaacaag                      38

<210> SEQ ID NO 13
<211> LENGTH: 42
<212> TYPE: DNA
<213> ORGANISM: Artificial Sequence
<220> FEATURE:
<223> OTHER INFORMATION: Primer

<400> SEQUENCE: 13
ggagagctgg tgctgctgga cttaggtgcc tgcgcgtcgt tg                  42

<210> SEQ ID NO 14
<211> LENGTH: 42
<212> TYPE: DNA
<213> ORGANISM: Artificial Sequence
<220> FEATURE:
<223> OTHER INFORMATION: Primer

<400> SEQUENCE: 14
caacgacgcg caggcaccta agtccagcag caccagctct cc                  42

<210> SEQ ID NO 15
<211> LENGTH: 19
<212> TYPE: DNA
<213> ORGANISM: Artificial Sequence

```
<220> FEATURE:
<223> OTHER INFORMATION: Primer

<400> SEQUENCE: 15
catataacca attgccctc                                                    19

<210> SEQ ID NO 16
<211> LENGTH: 372
<212> TYPE: DNA
<213> ORGANISM: Artificial Sequence
<220> FEATURE:
<223> OTHER INFORMATION: fusion protein coding sequence

<400> SEQUENCE: 16
atgaaggcga tcctctctct cgctgccgcg ctcttgagcg ccgcgcccgc gttctcgacc        60
gcagtctggg gccagtgcgg tggcatcggc ttctccggcg acaccacgtg caccgcttcc       120
acctgcgtga aggtcaacga ctactactcg cagtgccagc ctggcgcgtc cgcacccacg       180
tcaaccgcct ccgcgcccgg ccgtccgcgc tgccctggct cgcagtcgag cccgccagtc       240
cagcctacga ctcccagcgg ctgcactgct gagaggtggg ctcagtgcgg cggcaatggc       300
tggagcggct gcaccacctg cgtcgctggc agcacttgca cgaagattaa tgactggtac       360
catcagtgcc tg                                                          372

<210> SEQ ID NO 17
<211> LENGTH: 124
<212> TYPE: PRT
<213> ORGANISM: Artificial Sequence
<220> FEATURE:
<223> OTHER INFORMATION: fusion protein

<400> SEQUENCE: 17

Met Lys Ala Ile Leu Ser Leu Ala Ala Ala Leu Leu Ser Ala Ala Pro
1               5                   10                  15

Ala Phe Ser Thr Ala Val Trp Gly Gln Cys Gly Gly Ile Gly Phe Ser
            20                  25                  30

Gly Asp Thr Thr Cys Thr Ala Ser Thr Cys Val Lys Val Asn Asp Tyr
        35                  40                  45

Tyr Ser Gln Cys Gln Pro Gly Ala Ser Ala Pro Thr Ser Thr Ala Ser
    50                  55                  60

Ala Pro Gly Pro Ser Ala Cys Pro Gly Ser Gln Ser Ser Pro Pro Val
65                  70                  75                  80

Gln Pro Thr Thr Pro Ser Gly Cys Thr Ala Glu Arg Trp Ala Gln Cys
                85                  90                  95

Gly Gly Asn Gly Trp Ser Gly Cys Thr Thr Cys Val Ala Gly Ser Thr
            100                 105                 110

Cys Thr Lys Ile Asn Asp Trp Tyr His Gln Cys Leu
        115                 120

<210> SEQ ID NO 18
<211> LENGTH: 294
<212> TYPE: PRT
<213> ORGANISM: Artificial Sequence
<220> FEATURE:
<223> OTHER INFORMATION: fusion protein

<400> SEQUENCE: 18

Met Lys Ala Ile Leu Ser Leu Ala Ala Ala Leu Leu Ser Ala Ala Pro
1               5                   10                  15

Ala Phe Ser Thr Ala Val Trp Gly Gln Cys Gly Gly Ile Gly Phe Ser
```

```
              20                  25                  30
Gly Asp Thr Thr Cys Thr Ala Ser Thr Cys Val Lys Val Asn Asp Tyr
        35                  40                  45
Tyr Ser Gln Cys Gln Pro Gly Ala Ser Ala Pro Thr Ser Thr Ala Ser
     50                  55                  60
Ala Pro Gly Pro Ser Ala Cys Pro Leu Val Lys Arg Asp Asn Lys Phe
 65                  70                  75                  80
Asn Lys Glu Gln Gln Asn Ala Phe Tyr Glu Ile Leu His Leu Pro Asn
                 85                  90                  95
Leu Asn Glu Glu Gln Arg Asn Gly Phe Ile Gln Ser Leu Lys Asp Asp
            100                 105                 110
Pro Ser Gln Ser Ala Asn Leu Leu Ala Glu Ala Lys Lys Leu Asn Asp
        115                 120                 125
Ala Gln Ala Pro Lys Asp Asn Lys Phe Asn Lys Glu Gln Gln Asn Ala
    130                 135                 140
Phe Tyr Glu Ile Leu His Leu Pro Asn Leu Asn Glu Glu Gln Arg Asn
145                 150                 155                 160
Gly Phe Ile Gln Ser Leu Lys Asp Asp Pro Ser Gln Ser Ala Asn Leu
                165                 170                 175
Leu Ala Glu Ala Lys Lys Leu Asn Asp Ala Gln Ala Pro Lys Ala Val
            180                 185                 190
Trp Gly Gln Cys Gly Gly Ile Gly Phe Ser Gly Asp Thr Thr Cys Thr
        195                 200                 205
Ala Ser Thr Cys Val Lys Val Asn Asp Tyr Tyr Ser Gln Cys Gln Pro
    210                 215                 220
Gly Ala Ser Ala Pro Thr Ser Thr Ala Ser Ala Pro Gly Pro Ser Ala
225                 230                 235                 240
Cys Pro Gly Ser Gln Ser Ser Pro Pro Val Gln Pro Thr Thr Pro Ser
                245                 250                 255
Gly Cys Thr Ala Glu Arg Trp Ala Gln Cys Gly Gly Asn Gly Trp Ser
            260                 265                 270
Gly Cys Thr Thr Cys Val Ala Gly Ser Thr Cys Thr Lys Ile Asn Asp
        275                 280                 285
Trp Tyr His Gln Cys Leu
    290

<210> SEQ ID NO 19
<211> LENGTH: 38
<212> TYPE: DNA
<213> ORGANISM: Artificial Sequence
<220> FEATURE:
<223> OTHER INFORMATION: Primer

<400> SEQUENCE: 19
cttgttgaat ttgttatcac gcttcaccaa agggcacg                              38

<210> SEQ ID NO 20
<211> LENGTH: 38
<212> TYPE: DNA
<213> ORGANISM: Artificial Sequence
<220> FEATURE:
<223> OTHER INFORMATION: Primer

<400> SEQUENCE: 20
cgtgcccttt ggtgaagcgt gataacaaat tcaacaag                              38

<210> SEQ ID NO 21
```

```
<211> LENGTH: 42
<212> TYPE: DNA
<213> ORGANISM: Artificial Sequence
<220> FEATURE:
<223> OTHER INFORMATION: Primer

<400> SEQUENCE: 21
ccgcactggc cccagactgc cttaggtgcc tgcgcgtcgt tg                              42

<210> SEQ ID NO 22
<211> LENGTH: 42
<212> TYPE: DNA
<213> ORGANISM: Artificial Sequence
<220> FEATURE:
<223> OTHER INFORMATION: Primer

<400> SEQUENCE: 22
caacgacgcg caggcaccta aggcagtctg gggccagtgc gg                              42

<210> SEQ ID NO 23
<211> LENGTH: 242
<212> TYPE: PRT
<213> ORGANISM: Artificial Sequence
<220> FEATURE:
<223> OTHER INFORMATION: fusion protein

<400> SEQUENCE: 23

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Ala Thr Ser Gly His
            20                  25                  30

Gly His Tyr Gly Met Gly Trp Phe Arg Gln Val Pro Gly Lys Glu Arg
        35                  40                  45

Glu Phe Val Ala Ala Ile Arg Trp Ser Gly Lys Glu Thr Trp Tyr Lys
    50                  55                  60

Asp Ser Val Lys Gly Arg Phe Thr Ile Ser Arg Asp Asn Ala Lys Thr
65                  70                  75                  80

Thr Val Tyr Leu Gln Met Asn Ser Leu Lys Pro Glu Asp Thr Ala Val
                85                  90                  95

Tyr Tyr Cys Ala Ala Arg Pro Val Arg Val Asp Asp Ile Ser Leu Pro
            100                 105                 110

Val Gly Phe Asp Tyr Trp Gly Gln Gly Thr Gln Val Thr Val Ser Ser
        115                 120                 125

Asp Asn Lys Phe Asn Lys Glu Gln Gln Asn Ala Phe Tyr Glu Ile Leu
    130                 135                 140

His Leu Pro Asn Leu Asn Glu Glu Gln Arg Asn Gly Phe Ile Gln Ser
145                 150                 155                 160

Leu Lys Asp Asp Pro Ser Gln Ser Ala Asn Leu Leu Ala Glu Ala Lys
                165                 170                 175

Lys Leu Asn Asp Ala Gln Ala Pro Lys Asp Asn Lys Phe Asn Lys Glu
            180                 185                 190

Gln Gln Asn Ala Phe Tyr Glu Ile Leu His Leu Pro Asn Leu Asn Glu
        195                 200                 205

Glu Gln Arg Asn Gly Phe Ile Gln Ser Leu Lys Asp Asp Pro Ser Gln
    210                 215                 220

Ser Ala Asn Leu Leu Ala Glu Ala Lys Lys Leu Asn Asp Ala Gln Ala
225                 230                 235                 240

Pro Lys
```

```
<210> SEQ ID NO 24
<211> LENGTH: 615
<212> TYPE: PRT
<213> ORGANISM: Artificial Sequence
<220> FEATURE:
<223> OTHER INFORMATION: fusion protein

<400> SEQUENCE: 24

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
            20                  25                  30

Asp Ser Gly Ile Val Val Ala Ser Pro Ser Thr Asp Asn Pro Asp Phe
        35                  40                  45

Tyr Thr Trp Thr Arg Asp Ser Gly Leu Val Leu Lys Thr Leu Val Asp
    50                  55                  60

Leu Phe Arg Asn Gly Asp Thr Ser Leu Leu Ser Thr Ile Glu Asn Tyr
65                  70                  75                  80

Ile Ser Ala Gln Ala Ile Val Gln Gly Ile Ser Asn Pro Ser Gly Asp
                85                  90                  95

Leu Ser Ser Gly Ala Gly Leu Gly Glu Pro Lys Phe Asn Val Asp Glu
            100                 105                 110

Thr Ala Tyr Thr Gly Ser Trp Gly Arg Pro Gln Arg Asp Gly Pro Ala
        115                 120                 125

Leu Arg Ala Thr Ala Met Ile Gly Phe Gly Gln Trp Leu Leu Asp Asn
    130                 135                 140

Gly Tyr Thr Ser Thr Ala Thr Asp Ile Val Trp Pro Leu Val Arg Asn
145                 150                 155                 160

Asp Leu Ser Tyr Val Ala Gln Tyr Trp Asn Gln Thr Gly Tyr Asp Leu
                165                 170                 175

Trp Glu Glu Val Asn Gly Ser Ser Phe Phe Thr Ile Ala Val Gln His
            180                 185                 190

Arg Ala Leu Val Glu Gly Ser Ala Phe Ala Thr Ala Val Gly Ser Ser
        195                 200                 205

Cys Ser Trp Cys Asp Ser Gln Ala Pro Glu Ile Leu Cys Tyr Leu Gln
    210                 215                 220

Ser Phe Trp Thr Gly Ser Phe Ile Leu Ala Asn Phe Asp Ser Ser Arg
225                 230                 235                 240

Ser Gly Lys Asp Ala Asn Thr Leu Leu Gly Ser Ile His Thr Phe Asp
                245                 250                 255

Pro Glu Ala Ala Cys Asp Asp Ser Thr Phe Gln Pro Cys Ser Pro Arg
            260                 265                 270

Ala Leu Ala Asn His Lys Glu Val Val Asp Ser Phe Arg Ser Ile Tyr
        275                 280                 285

Thr Leu Asn Asp Gly Leu Ser Asp Ser Glu Ala Val Ala Val Gly Arg
    290                 295                 300

Tyr Pro Glu Asp Thr Tyr Tyr Asn Gly Asn Pro Trp Phe Leu Cys Thr
305                 310                 315                 320

Leu Ala Ala Ala Glu Gln Leu Tyr Asp Ala Leu Tyr Gln Trp Asp Lys
                325                 330                 335

Gln Gly Ser Leu Glu Val Thr Asp Val Ser Leu Asp Phe Phe Lys Ala
            340                 345                 350

Leu Tyr Ser Asp Ala Ala Thr Gly Thr Tyr Ser Ser Ser Ser Ser Thr
        355                 360                 365
```

```
Tyr Ser Ser Ile Val Asp Ala Val Lys Thr Phe Ala Asp Gly Phe Val
    370                 375                 380

Ser Ile Val Glu Thr His Ala Ala Ser Asn Gly Ser Met Ser Glu Gln
385                 390                 395                 400

Tyr Asp Lys Ser Asp Gly Glu Gln Leu Ser Ala Arg Asp Leu Thr Trp
            405                 410                 415

Ser Tyr Ala Ala Leu Leu Thr Ala Asn Asn Arg Arg Asn Ser Val Val
        420                 425                 430

Pro Ala Ser Trp Gly Glu Thr Ser Ala Ser Ser Val Pro Gly Thr Cys
    435                 440                 445

Ala Ala Thr Ser Ala Ile Gly Thr Tyr Ser Ser Val Thr Val Thr Ser
450                 455                 460

Trp Pro Ser Ile Val Ala Thr Gly Gly Thr Thr Thr Ala Thr Pro
465                 470                 475                 480

Thr Gly Ser Gly Ser Val Thr Ser Thr Ser Lys Thr Thr Ala Thr Ala
                485                 490                 495

Ser Lys Thr Ser Thr Asp Asn Lys Phe Asn Lys Glu Gln Gln Asn Ala
                500                 505                 510

Phe Tyr Glu Ile Leu His Leu Pro Asn Leu Asn Glu Glu Gln Arg Asn
            515                 520                 525

Gly Phe Ile Gln Ser Leu Lys Asp Asp Pro Ser Gln Ser Ala Asn Leu
    530                 535                 540

Leu Ala Glu Ala Lys Lys Leu Asn Asp Ala Gln Ala Pro Lys Asp Asn
545                 550                 555                 560

Lys Phe Asn Lys Glu Gln Gln Asn Ala Phe Tyr Glu Ile Leu His Leu
                565                 570                 575

Pro Asn Leu Asn Glu Glu Gln Arg Asn Gly Phe Ile Gln Ser Leu Lys
                580                 585                 590

Asp Asp Pro Ser Gln Ser Ala Asn Leu Leu Ala Glu Ala Lys Lys Leu
            595                 600                 605

Asn Asp Ala Gln Ala Pro Lys
            610                 615

<210> SEQ ID NO 25
<211> LENGTH: 559
<212> TYPE: PRT
<213> ORGANISM: Artificial Sequence
<220> FEATURE:
<223> OTHER INFORMATION: fusion protein

<400> SEQUENCE: 25

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
                20                  25                  30

Asp Ser Gly Ile Val Val Ala Ser Pro Ser Thr Asp Asn Pro Asp Tyr
            35                  40                  45

Phe Tyr Thr Trp Thr Arg Asp Ser Gly Leu Val Leu Lys Thr Leu Val
        50                  55                  60

Asp Leu Phe Arg Asn Gly Asp Thr Ser Leu Leu Ser Thr Ile Glu Asn
65                  70                  75                  80

Tyr Ile Ser Ala Gln Ala Ile Val Gln Gly Ile Ser Asn Pro Ser Gly
                85                  90                  95

Asp Leu Ser Ser Gly Ala Gly Leu Gly Glu Pro Lys Phe Asn Val Asp
            100                 105                 110
```

-continued

Glu Thr Ala Tyr Thr Gly Ser Trp Gly Arg Pro Gln Arg Asp Gly Pro
                115                 120                 125

Ala Leu Arg Ala Thr Ala Met Ile Gly Phe Gly Gln Trp Leu Leu Asp
130                 135                 140

Asn Gly Tyr Thr Ser Thr Ala Thr Asp Ile Val Trp Pro Leu Val Arg
145                 150                 155                 160

Asn Asp Leu Ser Tyr Val Ala Gln Tyr Trp Asn Gln Thr Gly Tyr Asp
                165                 170                 175

Leu Trp Glu Glu Val Asn Gly Ser Ser Phe Phe Thr Ile Ala Val Gln
                180                 185                 190

His Arg Ala Leu Val Glu Gly Ser Ala Phe Ala Thr Ala Val Gly Ser
                195                 200                 205

Ser Cys Ser Trp Cys Asp Ser Gln Ala Pro Glu Ile Leu Cys Tyr Leu
            210                 215                 220

Gln Ser Phe Trp Thr Gly Ser Phe Ile Leu Ala Asn Phe Asp Ser Ser
225                 230                 235                 240

Arg Ser Gly Lys Asp Ala Asn Thr Leu Leu Gly Ser Ile His Thr Phe
                245                 250                 255

Asp Pro Glu Ala Ala Cys Asp Asp Ser Thr Phe Gln Pro Cys Ser Pro
                260                 265                 270

Arg Ala Leu Ala Asn His Lys Glu Val Val Asp Ser Phe Arg Ser Ile
            275                 280                 285

Tyr Thr Leu Asn Asp Gly Leu Ser Asp Ser Glu Ala Val Ala Val Gly
            290                 295                 300

Arg Tyr Pro Glu Asp Thr Tyr Tyr Asn Gly Asn Pro Trp Phe Leu Cys
305                 310                 315                 320

Thr Leu Ala Ala Ala Glu Gln Leu Tyr Asp Ala Leu Tyr Gln Trp Asp
                325                 330                 335

Lys Gly Ser Leu Glu Val Thr Asp Val Ser Leu Asp Phe Phe Lys
                340                 345                 350

Ala Leu Tyr Ser Asp Ala Ala Thr Gly Thr Tyr Ser Ser Ser Ser Ser
                355                 360                 365

Thr Tyr Ser Ser Ile Val Asp Ala Val Lys Thr Phe Ala Asp Gly Phe
370                 375                 380

Val Ser Ile Val Glu Thr His Ala Ala Ser Asn Gly Ser Met Ser Glu
385                 390                 395                 400

Gln Tyr Asp Lys Ser Asp Gly Glu Gln Leu Ser Ala Arg Asp Leu Thr
                405                 410                 415

Trp Ser Tyr Ala Ala Leu Leu Thr Ala Asn Asn Arg Arg Asn Ser Val
                420                 425                 430

Val Pro Ala Ser Trp Gly Glu Thr Ser Ala Ser Ser Val Pro Gly Thr
                435                 440                 445

Cys Ala Ala Thr Ser Ala Ile Gly Thr Tyr Ser Ser Val Thr Val Thr
            450                 455                 460

Ser Trp Pro Ser Ile Val Ala Thr Gly Gly Thr Thr Thr Thr Ala Thr
465                 470                 475                 480

Pro Thr Gly Ser Gly Ser Val Thr Ser Thr Ser Lys Thr Thr Ala Thr
                485                 490                 495

Ala Ser Lys Thr Ser Thr Asp Asn Lys Phe Asn Lys Glu Gln Gln Asn
                500                 505                 510

Ala Phe Tyr Glu Ile Leu His Leu Pro Asn Leu Asn Glu Glu Gln Arg
                515                 520                 525

Asn Gly Phe Ile Gln Ser Leu Lys Asp Asp Pro Ser Gln Ser Ala Asn

```
                530                 535                 540
Leu Leu Ala Glu Ala Lys Lys Leu Asn Asp Ala Gln Ala Pro Lys
545                 550                 555

<210> SEQ ID NO 26
<211> LENGTH: 239
<212> TYPE: PRT
<213> ORGANISM: Artificial Sequence
<220> FEATURE:
<223> OTHER INFORMATION: fusion protein

<400> SEQUENCE: 26

Ala Val Trp Gly Gln Cys Gly Gly Ile Gly Phe Ser Gly Asp Thr Thr
1               5                   10                  15

Cys Thr Ala Ser Thr Cys Val Lys Val Asn Asp Tyr Tyr Ser Gln Cys
            20                  25                  30

Gln Pro Gly Ala Ser Ala Pro Thr Ser Thr Ala Ser Ala Pro Gly Pro
        35                  40                  45

Ser Ala Cys Pro Gly Ser Asp Asn Lys Phe Asn Lys Glu Gln Gln Asn
    50                  55                  60

Ala Phe Tyr Glu Ile Leu His Leu Pro Asn Leu Asn Glu Glu Gln Arg
65                  70                  75                  80

Asn Gly Phe Ile Gln Ser Leu Lys Asp Asp Pro Ser Gln Ser Ala Asn
                85                  90                  95

Leu Leu Ala Glu Ala Lys Lys Leu Asn Asp Ala Gln Ala Pro Lys Asp
            100                 105                 110

Asn Lys Phe Asn Lys Glu Gln Gln Asn Ala Phe Tyr Glu Ile Leu His
        115                 120                 125

Leu Pro Asn Leu Asn Glu Glu Gln Arg Asn Gly Phe Ile Gln Ser Leu
    130                 135                 140

Lys Asp Asp Pro Ser Gln Ser Ala Asn Leu Leu Ala Glu Ala Lys Lys
145                 150                 155                 160

Leu Asn Asp Ala Gln Ala Pro Lys Ser Ser Thr Ser Ser Pro Val
                165                 170                 175

Asn Gln Pro Thr Ser Thr Ser Thr Ser Thr Ser Thr Thr Ser Ser
            180                 185                 190

Pro Pro Val Gln Pro Thr Thr Pro Ser Gly Cys Thr Ala Glu Arg Trp
        195                 200                 205

Ala Gln Cys Gly Gly Asn Gly Trp Ser Gly Cys Thr Thr Cys Val Ala
    210                 215                 220

Gly Ser Thr Cys Thr Lys Ile Asn Asp Trp Tyr His Gln Cys Leu
225                 230                 235

<210> SEQ ID NO 27
<211> LENGTH: 218
<212> TYPE: PRT
<213> ORGANISM: Artificial Sequence
<220> FEATURE:
<223> OTHER INFORMATION: fusion protein

<400> SEQUENCE: 27

Asp Asn Lys Phe Asn Lys Glu Gln Gln Asn Ala Phe Tyr Glu Ile Leu
1               5                   10                  15

His Leu Pro Asn Leu Asn Glu Glu Gln Arg Asn Gly Phe Ile Gln Ser
            20                  25                  30

Leu Lys Asp Asp Pro Ser Gln Ser Ala Asn Leu Leu Ala Glu Ala Lys
        35                  40                  45
```

```
Lys Leu Asn Asp Ala Gln Ala Pro Lys Asp Asn Lys Phe Asn Lys Glu
 50                  55                  60
Gln Gln Asn Ala Phe Tyr Glu Ile Leu His Leu Pro Asn Leu Asn Glu
 65                  70                  75                  80
Glu Gln Arg Asn Gly Phe Ile Gln Ser Leu Lys Asp Asp Pro Ser Gln
                 85                  90                  95
Ser Ala Asn Leu Leu Ala Glu Ala Lys Lys Leu Asn Asp Ala Gln Ala
                100                 105                 110
Pro Lys Ala Val Trp Gly Gln Cys Gly Gly Ile Gly Phe Ser Gly Asp
                115                 120                 125
Thr Thr Cys Thr Ala Ser Thr Cys Val Lys Val Asn Asp Tyr Tyr Ser
130                 135                 140
Gln Cys Gln Pro Gly Ala Ser Ala Pro Thr Ser Thr Ala Ser Ala Pro
145                 150                 155                 160
Gly Pro Ser Ala Cys Pro Gly Ser Gln Ser Ser Pro Val Gln Pro
                165                 170                 175
Thr Thr Pro Ser Gly Cys Thr Ala Glu Arg Trp Ala Gln Cys Gly Gly
                180                 185                 190
Asn Gly Trp Ser Gly Cys Thr Thr Cys Val Ala Gly Ser Thr Cys Thr
                195                 200                 205
Lys Ile Asn Asp Trp Tyr His Gln Cys Leu
210                 215

<210> SEQ ID NO 28
<211> LENGTH: 185
<212> TYPE: PRT
<213> ORGANISM: Artificial Sequence
<220> FEATURE:
<223> OTHER INFORMATION: fusion protein

<400> SEQUENCE: 28

Gln Val Gln Leu Gln Glu Ser Gly Gly Gly Leu Val Gln Ala Gly Gly
  1               5                  10                  15
Ser Leu Arg Leu Ser Cys Ala Ala Ser Gly Arg Ala Thr Ser Gly His
                 20                  25                  30
Gly His Tyr Gly Met Gly Trp Phe Arg Gln Val Pro Gly Lys Glu Arg
             35                  40                  45
Glu Phe Val Ala Ala Ile Arg Trp Ser Gly Lys Glu Thr Trp Tyr Lys
 50                  55                  60
Asp Ser Val Lys Gly Arg Phe Thr Ile Ser Arg Asp Asn Ala Lys Thr
 65                  70                  75                  80
Thr Val Tyr Leu Gln Met Asn Ser Leu Lys Pro Glu Asp Thr Ala Val
                 85                  90                  95
Tyr Tyr Cys Ala Ala Arg Pro Val Arg Val Asp Asp Ile Ser Leu Pro
                100                 105                 110
Val Gly Phe Asp Tyr Trp Gly Gln Gly Thr Gln Val Thr Val Ser Ser
            115                 120                 125
Asp Asn Lys Phe Asn Lys Glu Gln Gln Asn Ala Phe Tyr Glu Ile Leu
130                 135                 140
His Leu Pro Asn Leu Asn Glu Glu Gln Arg Asn Gly Phe Ile Gln Ser
145                 150                 155                 160
Leu Lys Asp Asp Pro Ser Gln Ser Ala Asn Leu Leu Ala Glu Ala Lys
                165                 170                 175
Lys Leu Asn Asp Ala Gln Ala Pro Lys
                180                 185
```

<210> SEQ ID NO 29
<211> LENGTH: 390
<212> TYPE: DNA
<213> ORGANISM: Artificial Sequence
<220> FEATURE:
<223> OTHER INFORMATION: Z::Z domain coding sequence

<400> SEQUENCE: 29

| | | |
|---|---|---|
| tcattctgca gcagcggcgg ataacaaatt taacaaagaa cagcagaacg cgttttatga | 60 |
| aatcctgcat ctgccgaacc tgaacgaaga acagcgcaac gcgtttatcc agagcctgaa | 120 |
| agatgatccg agccagagcg cgaacctgct ggcggaagcg aaaaaactga acgatgcgca | 180 |
| ggcgccgaaa gtcgacaaca aatttaataa ggaacaacaa aacgccttct acgaaattct | 240 |
| ccatctaccc aatcttaatg aagagcagcg caacgctttt attcaatcgc ttaaggacga | 300 |
| tcccagccaa tcggcaaatc ttctggctga agctaaaaag cttaatgacg cgcaagctcc | 360 |
| taaagtgtag tcgctagcgg ccgcttagtt | 390 |

<210> SEQ ID NO 30
<211> LENGTH: 626
<212> TYPE: DNA
<213> ORGANISM: Artificial Sequence
<220> FEATURE:
<223> OTHER INFORMATION: streptavidin coding sequence

<400> SEQUENCE: 30

| | | |
|---|---|---|
| aagcttaatg acgcgcaagc tcctaaagtg gacccgtcaa agattccaa agcccaggta | 60 |
| agtgcagctg aagcaggcat aacgggaaca tggtacaatc aactgggaag cacgtttatc | 120 |
| gtaacagcag gagcggacgg agcgttgaca ggcacatacg aatctgccgt tggaaacgca | 180 |
| gaatcgcgtt acacacttac aggtagatac gattcagcac cggctaccga tggaagcgga | 240 |
| actgcattgg gatggagagt ggcttggaaa acaactata gaaatgcgca tagcgccacg | 300 |
| acatggtctg gccaatacgt cggaggagca gaagctagaa tcaatacaca atggacatta | 360 |
| acgagcggga ctacagaagc aaatgcctgg aaatcgacgt taagaggtca tgataccttt | 420 |
| accaaagtaa agccgtccgc agcatcaatt gatgcagcga agaaagcagg agtgaataac | 480 |
| ggtaatcctt tggatgcagt gcaacaatag tcgctagcgg ccgcgtcgac tagaagagca | 540 |
| gagaggacgg atttcctgaa ggaaatccgt ttttttattt tgcccgtctt ataaatttcg | 600 |
| ttgagatctt gatcatcgat aagctt | 626 |

<210> SEQ ID NO 31
<211> LENGTH: 4084
<212> TYPE: DNA
<213> ORGANISM: Artificial Sequence
<220> FEATURE:
<223> OTHER INFORMATION: plasmid pSJ6208

<400> SEQUENCE: 31

| | | |
|---|---|---|
| tcgcgcgttt cggtgatgac ggtgaaaacc tctgacacat gcagctcccg gagacggtca | 60 |
| cagcttgtct gtaagcggat gccgggagca gacaagcccg tcagggcgcg tcagcgggtg | 120 |
| ttggcgggtg tcgggctgg cttaactatg cggcatcaga gcagattgta ctgagagtgc | 180 |
| accatatgcg gtgtgaaata ccgcacagat gcgtaaggag aaaataccgc atcaggcgcc | 240 |
| attcgccatt caggctgcgc aactgttggg aagggcgatc ggtgcgggcc tcttcgctat | 300 |
| tacgccagct ggcgaaaggg ggatgtgctg caaggcgatt aagttgggta acgccagggt | 360 |
| tttcccagtc acgacgttgt aaaacgacgg ccagtgaatt cagatctaaa gataatatct | 420 |

```
ttgaattgta acscccctca aaagtaagaa ctacaaaaaa agaatacgtt atatagaaat      480
atgtttgaac cttcttcaga ttacaaatat attcggacgg actctacctc aaatgcttat      540
ctaactatag aatgacatac aagcacaacc ttgaaaattt gaaaatataa ctaccaatga      600
acttgttcat gtgaattatc gctgtattta attttctcaa ttcaatatat aatatgccaa      660
tacattgtta caagtagaaa ttaagacacc cttgatagcc ttactatacc taacatgatg      720
tagtattaaa tgaatatgta aatatattta tgataagaag cgacttattt ataatcatta      780 catattttc tattggaatg attaagattc aatagaata gtgtataaat tatttatctt       840
gaaaggaggg atgcctaaaa acgaagaaca ttaaaaacat atatttgcac cgtctaatgg      900
atttatgaaa aatcatttta tcagtttgaa aattatgtat tatggccaca ttgaaagggg      960
aggagaatca tgaaacaaca aaaacggctt tacgcccgat tgctgacgct gttatttgcg     1020
ctcatcttct tgctgcctca ttctgcagca gcggcgatcg tcggcggtac gaaggccagt     1080
acctcgacct acccgttcgt ggtcttcctg actgacagca ccggtttcca gttctgcggt     1140
ggcacgctgg tcaagccgaa caaggtggtc acggcggcgc actgcaccgt cggtgagtcc     1200
gcggccaaca tccgcgttgt cgccggtcgc gacgacaagc agagcaccgc cggcactgtc     1260
tcgaaggtca gcaagatctg gatccacccg agttaccagg acgccaccaa gggcagcgac     1320
gtgtcggtgc tgaccctgtc gaccagcctg acccagttca cgccgttgcc gctggctgcc     1380
accactgaca ccgcgctgta caaggagggc accgccgcga ccatcctcgg ctggggtgac     1440
accaccgagg gcgggtcggc ctctcggtac ctgctcaagg cgacagtgcc gctgaccagc     1500
gacgccacct gcaagaaggc gtacggcgag tacagttcca ccgcgatggt ctgtgccgga     1560
tacccgcagg gtggcacgga cacctgccag ggcgactccg gcggtccgct cgtcgcggc      1620 aacaagctga tcggcatcac ctcgtggggc cagggctgcg ccgaggccgg ttatccaggc     1680
gtctacaccc gggtcgccac ctacagttcg ctgatcaccc agcagctcgg ctagtcgcta     1740
gcggccgcgt cgactagaag agcagagagg acggatttcc tgaaggaaat ccgttttttt     1800
attttgcccg tcttataaat ttcgttgaga tcttgatcat cgataagctt ggcgtaatca     1860
tggtcatagc tgtttcctgt gtgaaattgt tatccgctca caattccaca caacatacga     1920
gccggaagca taaagtgtaa agcctggggt gcctaatgag tgagctaact cacattaatt     1980
gcgttgcgct cactgcccgc tttccagtcg ggaaacctgt cgtgccagct gcattaatga     2040
atcggccaac gcgcggggag aggcggtttg cgtattgggc gctcttccgc ttcctcgctc     2100
actgactcgc tgcgctcggt cgttcggctg cggcgagcgg tatcagctca ctcaaaggcg     2160
gtaatacggt tatccacaga atcaggggat aacgcaggaa agaacatgtg agcaaaaggc     2220
cagcaaaagg ccaggaaccg taaaaaggcc gcgttgctgg cgtttttcca taggctccgc     2280 cccccctgacg agcatcacaa aaatcgacgc tcaagtcaga ggtggcgaaa cccgacagga     2340
ctataaagat accaggcgtt tccccctgga agctccctcg tgcgctctcc tgttccgacc     2400
ctgccgctta ccggatacct gtccgccttt ctcccttcgg aagcgtggc gctttctcaa      2460 tgctcacgct gtaggtatct cagttcggtg taggtcgttc gctccaagct gggctgtgtg     2520
cacgaacccc ccgttcagcc cgaccgctgc gccttatccg gtaactatcg tcttgagtcc     2580
aacccggtaa gacacgactt atcgccactg gcagcagcca ctggtaacag gattagcaga     2640
gcgaggtatg taggcggtgc tacagagttc ttgaagtggt ggcctaacta cggctacact     2700
agaaggacag tatttggtat ctgcgctctg ctgaagccag ttaccttcgg aaaaagagtt     2760
```

```
ggtagctctt gatccggcaa acaaaccacc gctggtagcg gtggtttttt tgtttgcaag   2820
cagcagatta cgcgcagaaa aaaggatctc aagaagatc  ctttgatctt ttctacgggg   2880
tctgacgctc agtggaacga aaactcacgt taagggattt tggtcatgag attatcaaaa   2940
aggatcttca cctagatcct tttaaattaa aaatgaagtt ttaaatcaat ctaaagtata   3000
tatgagtaaa cttggtctga cagttaccaa tgcttaatca gtgaggcacc tatctcagcg   3060
atctgtctat ttcgttcatc catagttgcc tgactccccg tcgtgtagat aactacgata   3120
cgggagggct taccatctgg ccccagtgct gcaatgatac cgcgagaccc acgctcaccg   3180
gctccagatt tatcagcaat aaaccagcca gccggaaggg ccgagcgcag aagtggtcct   3240
gcaactttat ccgcctccat ccagtctatt aattgttgcc gggaagctag agtaagtagt   3300
tcgccagtta atagtttgcg caacgttgtt gccattgcta caggcatcgt ggtgtcacgc   3360
tcgtcgtttg gtatggcttc attcagctcc ggttcccaac gatcaaggcg agttacatga   3420
tcccccatgt tgtgcaaaaa agcggttagc tccttcggtc ctccgatcgt tgtcagaagt   3480
aagttggccg cagtgttatc actcatggtt atggcagcac tgcataattc tcttactgtc   3540
atgccatccg taagatgctt ttctgtgact ggtgagtact caaccaagtc attctgagaa   3600
tagtgtatgc ggcgaccgag ttgctcttgc ccggcgtcaa tacgggataa taccgcgcca   3660
catagcagaa cttttaaagt gctcatcatt ggaaaacgtt cttcggggcg aaaactctca   3720
aggatcttac cgctgttgag atccagttcg atgtaaccca ctcgtgcacc caactgatct   3780
tcagcatctt ttactttcac cagcgtttct gggtgagcaa aaacaggaag gcaaaatgcc   3840
gcaaaaaagg aataagggc  gacacggaaa tgttgaatac tcatactctt ccttttttcaa   3900 tattattgaa gcatttatca gggttattgt ctcatgagcg gatacatatt tgaatgtatt   3960
tagaaaaata aacaaatagg ggttccgcgc acatttcccc gaaaagtgcc acctgacgtc   4020
taagaaacca ttattatcat gacattaacc tataaaaata ggcgtatcac gaggcccttt   4080
cgtc                                                                4084
```

<210> SEQ ID NO 32
<211> LENGTH: 6691
<212> TYPE: DNA
<213> ORGANISM: Artificial Sequence
<220> FEATURE:
<223> OTHER INFORMATION: Plasmid sequence pSJ6321

<400> SEQUENCE: 32

```
gaattcagat ctaaagataa tatctttgaa ttgtaacscc cctcaaaagt aagaactaca     60 aaaaagaat  acgttatata gaaatatgtt tgaaccttct tcagattaca aatatattcg    120
gacggactct acctcaaatg cttatctaac tatagaatga catacaagca caaccttgaa    180
aatttgaaaa tataactacc aatgaacttg ttcatgtgaa ttatcgctgt atttaatttt    240
ctcaattcaa tatataatat gccaatacat tgttacaagt agaaattaag acacccttga    300
tagccttact ataacctaaca tgatgtagta ttaaatgaat atgtaaatat atttatgata    360
agaagcgact tatttataat cattacatat ttttctattg gaatgattaa gattccaata    420
gaatagtgta taaattattt atcttgaaag gagggatgcc taaaaacgaa gaacattaaa    480
aacatatatt tgcaccgtct aatggattta tgaaaatca ttttatcagt ttgaaaatta     540
tgtattatgg ccacattgaa agggaggag  aatcatgaaa caacaaaaac ggctttacgc    600
ccgattgctg acgctgttat ttgcgctcat cttcttgctg cctcattctg cagcagcggc    660
ggccaccgga gcgctccccc agtcacccac cccggaggcc gacgcggtct ccatgcagga    720
```

```
ggcgctccag cgcgacctcg acctgacctc cgccgaggcc gaggagctgc tggccgccca    780
ggacaccgcc ttcgaggtcg acgaggccgc ggccgaggcc gccggggacg cctacggcgg    840
ctccgtcttc gacaccgaga gcctggaact gaccgtcctg gtcaccgatg ccgccgcggt    900
cgaggccgtg gaggccaccg cgccgggac cgagctggtc tcctacggca tcgacggtct    960
cgacgagatc gtccaggagc tcaacgccgc cgacgccgtt cccggtgtgg tcggctggta   1020
cccgacgtg gcgggtgaca ccgtcgtcct ggaggtcctg gagggttccg gagccgacgt   1080
cagcggcctg ctcgcggacg ccggcgtgga cgcctcggcc gtcgaggtga ccacgagcga   1140
ccagcccgag ctctacgccg acatcatcgg tggtctggcc tacaccatgg gcggccgctg   1200
ttcggtcggc ttcgcggcca ccaacgccgc cggtcagccc gggttcgtca ccgccggtca   1260
ctgcggccgc gtgggcaccc aggtgaccat cggcaacggc aggggcgtct tcgagcagtc   1320
cgtcttcccc ggcaacgacg cggccttcgt ccgcggtacg tccaacttca cgctgaccaa   1380
cctggtcagc cgctacaaca ccggcgggta cgccacggtc gccggtcaca accaggcccc   1440
catcggctcc tccgtctgcc gctccggctc caccaccggt tggcactgcg gcaccatcca   1500
ggcccgcggc cagtcggtga gctaccccga gggcaccgtc accaacatga cccgaccac    1560
cgtgtgcgcc gagcccggcg actccggcgg ctcctacatc tccggcaccc aggcccaggg   1620
cgtgacctcc ggcggctccg gcaactgccg caccggcggg accacttct accaggaggt   1680
cacccccatg gtgaactcct ggggcgtccg tctccggacc tgaacgcgtg ctagcggccg   1740
cgtcgactag aagagcagag aggacggatt tcctgaagga aatccgtttt tttattttgc   1800
ccgtcttata aatttcgttg agatctacgc gtccatgggc tagcgcggcc gcgtcgacag   1860
gcctctttga ttcatttta taattaattt taacaaagtg tcatcagccc tcaggaagga   1920
cttgctgaca gtttgaatcg cataggtaag gcggggatga aatggcaacg ttatctgatg   1980
tagcaaagaa agcaaatgtg tcgaaaatga cggtatcgcg ggtgatcaat catcctgaga   2040
ctgtgacgga tgaattgaaa aagcttgttc attccgcaat gaaggagctc aattatatac   2100
cgaactatgc agcaagagcg ctcgttcaaa acagaacaca ggtcgtcaag ctgctcatac   2160
tggaagaaat ggatacaaca gaaccttatt atatgaatct gttaacggga atcagccgcg   2220
agctggaccg tcatcattat gctttgcagc ttgtcacaag gaaatctctc aatatcggcc   2280
agtgcgacgg cattattgcg acggggttga gaaaagccga ttttgaaggg ctcatcaagg   2340
tttttgaaaa gcgtgtcgtt gtattcggga cgtcgattca caaaatagg cacacgaaaa   2400
acaagtaagg gatgcagttt atgcatccct taacttactt attaaataat ttatagctat   2460
tgaaaagaga taagaattgt tcaaagctaa tattgtttaa atcgtcaatt cctgcatgtt   2520
ttaaggaatt gttaaattga ttttttgtaa atatttctt gtattctttg ttaacccatt   2580
tcataacgaa ataattatac ttttgtttat ctttgtgtga tattcttgat ttttttctac   2640
ttaatctgat aagtgagcta ttcactttag gtttaggatg aaaatattct cttgaaacca   2700
tacttaatat agaaatatca acttctgcca ttaaaagtaa tgccaatgag cgttttgtat   2760
ttaataatct tttagcaaac ccgtattcca cgattaaata aatctcatta gctatactat   2820
caaaaacaat tttgcgtatt atatccgtac ttatgttata aggtatatta ccatatattt   2880
tataggattg gttttttagga aatttaaact gcaatatatc cttgtttaaa acttggaaat   2940
tatcgtgatc aacaagttta ttttctgtag ttttgcataa tttatggtct atttcaatgg   3000
cagttacgaa attacacctc tttactaatt caagggtaaa atggcctttt cctgagccga   3060
```

```
tttcaaagat attatcatgt tcatttaatc ttatatttgt cattattttta tctatattat    3120 gttttgaagt aataaagttt tgactgtgtt ttatatttttt ctcgttcatt ataaccctct    3180
ttaatttggt tatatgaatt ttgcttatta acgattcatt ataaccactt attttttgtt    3240
tggttgataa tgaactgtgc tgattacaaa aatactaaaa atgcccatat ttttttcctcc   3300 ttataaaatt agtataatta tagcacgagc tctgataaat atgaacatga tgagtgatcg    3360
ttaaatttat actgcaatcg gatgcgatta ttgaataaaa gatatgagag atttatctaa    3420
tttctttttt cttgtaaaaa aagaaagttc ttaaaggttt tatagttttg gtcgtagagc    3480
acacggttta acgacttaat tacgaagtaa ataagtctag tgtgttagac tttatgaaat    3540
ctatatacgt ttatatatat ttattatccg gaggtgtagc atgtctcatt caattttgag    3600
ggttgccaga gttaaaggat caagtaatac aaacgggata caaagacata atcaaagaga    3660
gaataaaaac tataataata aagacataaa tcatgaggaa acatataaaa attatgattt    3720
gattaacgca caaatataa agtataaaga taaaattgat gaaacgattg atgagaatta    3780
ttcagggaaa cgtaaaattc ggtcagatgc aattcgacat gtggacggac tggttacaag    3840
tgataaagat ttctttgatg atttaagcgg agaagaaata gaacgatttt ttaaagatag    3900
cttggagttt ctagaaaatg aatacggtaa ggaaaatatg ctgtatgcga ctgtccatct    3960
ggatgaaaga gtcccacata tgcactttgg ttttgtccct ttaacagagg acgggagatt    4020
gtctgcaaaa gaacagttag gcaacaagaa agactttact caattacaag atagatttaa    4080
tgagtatgtg aatgagaaag gttatgaact tgaaagaggc acgtccaaag aggttacaga    4140
acgagaacat aaagcgatgg atcagtacaa gaaagatact gtatttcata aacaggaact    4200
gcaagaagtt aaggatgagt tacagaaggc aaataagcag ttacagagtg aatagagca    4260 tatgaggtct acgaaaccct ttgattatga aaatgagcgt acaggtttgt tctctggacg    4320
tgaagagact ggtagaaaga tattaactgc tgatgaattt gaacgcctgc aagaaacaat    4380
ctcttctgca gaacggattg ttgatgatta cgaaaatatt aagagcacag actattacac    4440
agaaaatcaa gaattaaaaa aacgtagaga gagtttgaaa gaagtagtga atacatggaa    4500
agaggggtat cacgaaaaaa gtaaagaggt taataaatta aagcgagaga atgatagttt    4560
gaatgagcag ttgaatgtat cagagaaatt tcaagctagt acagtgactt tatatcgtgc    4620
tgcgagggcg aatttccctg ggtttgagaa agggtttaat aggcttaaag agaaattctt    4680
taatgattcc aaatttgagc gtgtgggaca gtttatggat gttgtacagg ataatgtcca    4740
gaaggtcgat agaaagcgtg agaaacagcg tacagacgat ttagagatgt agaggtactt    4800
ttatgccgag aaaactttt gcgtgtgaca gtccttaaaa tatacttaga gcgtaagcga    4860
aagtagtagc gacagctatt aactttcggt ttcaaagctc taggattttt aatgggacgca    4920 gcgcatcaca cgcaaaaagg aaattggaat aaatgcgaaa tttgagatgt taattaaaga    4980 ccttttttgag gtcttttttt cttagatttt tgggttatt taggggagaa acatagggg    5040 ggtactacga cctcccccct aggtgtccat tgtccattgt ccaaacaaat aaataaatat    5100
tgggttttta atgttaaaag gttgttttt atgttaaagt gaaaaaaaca gatgttggga    5160
ggtacagtga tggttgtaga tagaaaagaa gagaaaaaag ttgctgttac tttaagactt    5220
acaacagaag aaaatgagat attaaataga atcaaagaaa aatataatat tagcaaatca    5280
gatgcaaccg gtattctaat aaaaaaatat gcaaaggagg aatacggtgc attttaaaca    5340
aaaaaagata gacagcactg gcatgctgcc tatctatgac taaattttgt taagtgtatt    5400
agcaccgtta ttatatcatg agcgaaaatg taataaaaga aactgaaaac aagaaaaatt    5460

```
caagaggacg taattggaca tttgttttat atccagaatc agcaaaagcc gagtggttag 5520
agtatttaaa agagttacac attcaatttg tagtgtctcc attacatgat agggatactg 5580
atacagaagg taggatgaaa aaagagcatt atcatattct agtgatgtat gagggtaata 5640
aatcttatga acagataaaa ataattacag aagaattgaa tgcgactatt ccgcagattg 5700
caggaagtgt gaaaggtctt gtgagatata tgcttcacat ggacgatcct aataaattta 5760
aatatcaaaa agaagatatg atagtttatg gcggtgtaga tgttgatgaa ttattaaaga 5820
aaacaacaac agatagatat aaattaatta aagaaatgat tgagtttatt gatgaacaag 5880
gaatcgtaga atttaagagt ttaatggatt atgcaatgaa gtttaaattt gatgattggt 5940
tcccgctttt atgtgataac tcggcgtatg ttattcaaga atatataaaa tcaaatcggt 6000
ataaatctga ccgatagatt ttgaatttag gtgtcacaag acactctttt ttcgcaccag 6060
cgaaaactgg tttaagccga ctgcgcaaaa gacataatcg actctagagg atccccgggt 6120
accgagctct gccttttagt ccagctgatt tcactttttg cattctacaa actgcataac 6180
tcatatgtaa atcgctcctt tttaggtggc acaaatgtga ggcattttcg ctctttccgg 6240
caaccacttc caagtaaagt ataacacact atactttata ttcataaagt gtgtgctctg 6300
cgaggctgtc ggcagtgccg accaaaacca taaaaccttt aagacctttc ttttttttac 6360
gagaaaaaag aaacaaaaaa acctgccctc tgccacctca gcaaaggggg gttttgctct 6420
cgtgctcgtt taaaaatcag caagggacag gtagtatttt ttgagaagat cactcaaaaa 6480
atctccacct ttaaaccctt gccaattttt attttgtccg ttttgtctag cttaccgaaa 6540
gccagactca gcaagaataa aatttttatt gtctttcggt tttctagtgt aacggacaaa 6600
accactcaaa ataaaaaaga tacaagagag gtctctcgta tcttttattc agcaatcgcg 6660
cccgattgct gaacagatta ataatgagct c 6691

<210> SEQ ID NO 33
<211> LENGTH: 3757
<212> TYPE: DNA
<213> ORGANISM: Artificial Sequence
<220> FEATURE:
<223> OTHER INFORMATION: Plasmid sequence pMOL2743

<400> SEQUENCE: 33
tcgcgcgttt cggtgatgac ggtgaaaacc tctgacacat gcagctcccg gagacggtca 60
cagcttgtct gtaagcggat gccgggagca gacaagcccg tcagggcgcg tcagcgggtg 120
ttggcgggtg tcggggctgg cttaactatg cggcatcaga gcagattgta ctgagagtgc 180
accatatgcg gtgtgaaata ccgcacagat gcgtaaggag aaaataccgc atcaggcgcc 240
attcgccatt caggctgcgc aactgttggg aagggcgatc ggtgcgggcc tcttcgctat 300
tacgccagct ggcgaaaggg ggatgtgctg caaggcgatt aagttgggta acgccagggt 360
tttcccagtc acgacgttgt aaaacgacgg ccagtgaatt cagatctaaa gataatatct 420
ttgaattgta acscccctca aaagtaagaa ctacaaaaaa agaatacgtt atatagaaat 480
atgtttgaac cttcttcaga ttacaaatat attcggacgg actctacctc aaatgcttat 540
ctaactatag aatgacatac aagcacaacc ttgaaaattt gaaaatataa ctaccaatga 600
acttgttcat gtgaattatc gctgtattta attttctcaa ttcaatatat aatatgccaa 660
tacattgtta caagtagaaa ttaagacacc cttgatagcc ttactatacc taacatgatg 720
tagtattaaa tgaatatgta aatatattta tgataagaag cgacttattt ataatcatta 780

```
catatttttc tattggaatg attaagattc caatagaata gtgtataaat tatttatctt    840
gaaaggaggg atgcctaaaa acgaagaaca ttaaaaacat atatttgcac cgtctaatgg    900
atttatgaaa aatcatttta tcagtttgaa aattatgtat tatggccaca ttgaaagggg    960
aggagaatca tgaaacaaca aaaacggctt tacgcccgat tgctgacgct gttatttgcg   1020
ctcatcttct tgctgcctca ttctgcagca gcggcggata acaaatttaa caaagaacag   1080
cagaacgcgt tttatgaaat cctgcatctg ccgaacctga cgaagaaca gcgcaacgcg    1140
tttatccaga gcctgaaaga tgatccgagc cagagcgcga acctgctggc ggaagcgaaa   1200
aaactgaacg atgcgcaggc gccgaaagtc gacaacaaat taataagga acaacaaaac    1260
gccttctacg aaattctcca tctacccaat cttaatgaag agcagcgcaa cgcttttatt   1320
caatcgctta aggacgatcc cagccaatcg gcaaatcttc tggctgaagc taaaaagctt   1380
aatgacgcgc aagctcctaa agtgtagtcg ctagcggccg cgtcgactag aagagcagag   1440
aggacggatt tcctgaagga aatccgtttt tttattttgc ccgtcttata aatttcgttg   1500
agatcttgat catcgataag cttggcgtaa tcatggtcat agctgtttcc tgtgtgaaat   1560
tgttatccgc tcacaattcc acacaacata cgagccggaa gcataaagtg taaagcctgg   1620
ggtgcctaat gagtgagcta actcacatta attgcgttgc gctcactgcc cgctttccag   1680
tcgggaaacc tgtcgtgcca gctgcattaa tgaatcggcc aacgcgcggg gagaggcggt   1740
ttgcgtattg ggcgctcttc cgcttcctcg ctcactgact cgctgcgctc ggtcgttcgg   1800
ctgcggcgag cggtatcagc tcactcaaag gcggtaatac ggttatccac agaatcaggg   1860
gataacgcag gaaagaacat gtgagcaaaa ggccagcaaa aggccaggaa ccgtaaaaag   1920
gccgcgttgc tggcgttttt ccataggctc cgcccccctg acgagcatca caaaaatcga   1980
cgctcaagtc agaggtggcg aaacccgaca ggactataaa gataccaggc gtttccccct   2040
ggaagctccc tcgtgcgctc tcctgttccg accctgccgc ttaccggata cctgtccgcc   2100
tttctccctt cgggaagcgt ggcgctttct caatgctcac gctgtaggta tctcagttcg   2160
gtgtaggtcg ttcgctccaa gctgggctgt gtgcacgaac ccccgttca gcccgaccgc    2220
tgcgccttat ccggtaacta tcgtcttgag tccaacccgg taagacacga cttatcgcca   2280
ctggcagcag ccactggtaa caggattagc agagcgaggt atgtaggcgg tgctacagag   2340
ttcttgaagt ggtggcctaa ctacggctac actagaagga cagtatttgg tatctgcgct   2400
ctgctgaagc cagttacctt cggaaaaaga gttggtagct cttgatccgg caaacaaacc   2460
accgctggta gcggtggttt ttttgtttgc aagcagcaga ttacgcgcag aaaaaaagga   2520
tctcaagaag atcctttgat cttttctacg gggtctgacg ctcagtggaa cgaaaactca   2580
cgttaaggga ttttggtcat gagattatca aaaaggatct tcacctagat ccttttaaat   2640
taaaaatgaa gttttaaatc aatctaaagt atatatgagt aaacttggtc tgacagttac   2700
caatgcttaa tcagtgaggc acctatctca gcgatctgtc tatttcgttc atccatagtt   2760
gcctgactcc ccgtcgtgta gataactacg atacgggagg gcttaccatc tggccccagt   2820
gctgcaatga taccgcgaga cccacgctca ccggctccag atttatcagc aataaaccag   2880
ccagccggaa gggccgagcg cagaagtggt cctgcaactt tatccgcctc catccagtct   2940
attaattgtt gccgggaagc tagagtaagt agttcgccag ttaatagttt gcgcaacgtt   3000
gttgccattg ctacaggcat cgtggtgtca cgctcgtcgt ttggtatggc ttcattcagc   3060
tccggttccc aacgatcaag gcgagttaca tgatccccca tgttgtgcaa aaaagcggtt   3120
agctccttcg gtcctccgat cgttgtcaga agtaagttgg ccgcagtgtt atcactcatg   3180
```

```
gttatggcag cactgcataa ttctcttact gtcatgccat ccgtaagatg cttttctgtg    3240
actggtgagt actcaaccaa gtcattctga gaatagtgta tgcggcgacc gagttgctct    3300
tgcccggcgt caatacggga taataccgcg ccacatagca gaactttaaa agtgctcatc    3360
attgaaaaac gttcttcggg gcgaaaactc tcaaggatct taccgctgtt gagatccagt    3420
tcgatgtaac ccactcgtgc acccaactga tcttcagcat cttttacttt caccagcgtt    3480
tctgggtgag caaaaacagg aaggcaaaat gccgcaaaaa agggaataag ggcgacacgg    3540
aaatgttgaa tactcatact cttcctttt  caatattatt gaagcattta tcagggttat    3600
tgtctcatga gcggatacat atttgaatgt atttagaaaa ataaacaaat aggggttccg    3660
cgcacatttc cccgaaaagt gccacctgac gtctaagaaa ccattattat catgacatta    3720
acctataaaa ataggcgtat cacgaggccc tttcgtc                            3757

<210> SEQ ID NO 34
<211> LENGTH: 4234
<212> TYPE: DNA
<213> ORGANISM: Artificial Sequence
<220> FEATURE:
<223> OTHER INFORMATION: plasmid sequence pMOL2744

<400> SEQUENCE: 34
tcgcgcgttt cggtgatgac ggtgaaaacc tctgacacat gcagctcccg gagacggtca      60
cagcttgtct gtaagcggat gccggagcag acaagcccg  tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cagatctaaa gataatatct     420
ttgaattgta acsccctca aaagtaagaa ctacaaaaaa agaatacgtt atatagaaat     480
atgtttgaac cttcttcaga ttacaaatat attcggacgg actctacctc aaatgcttat     540
ctaactatag aatgacatac aagcacaacc ttgaaaattt gaaatataa  ctaccaatga     600 acttgttcat gtgaattatc gctgtattta attttctcaa ttcaatatat aatatgccaa     660
tacattgtta caagtagaaa ttaagacacc cttgatagcc ttactatacc taacatgatg     720
tagtattaaa tgaatatgta aatatattta tgataagaag cgacttattt ataatcatta     780 catattttc  tattggaatg attaagattc caatagaata gtgtataaat tatttatctt     840
gaaaggaggg atgcctaaaa acgaagaaca ttaaaaacat atatttgcac cgtctaatgg     900
atttatgaaa aatcattta  tcagtttgaa aattatgtat tatggccaca ttgaaagggg     960
aggagaatca tgaaacaaca aaaacggctt tacgcccgat tgctgacgct gttatttgcg    1020
ctcatcttct tgctgcctca ttctgcagca gcggcgata  acaaatttaa caagaacag    1080 cagaacgcgt tttatgaaat cctgcatctg ccgaacctga cgaagaaca  gcgcaacgcg    1140 tttatccaga gcctgaaaga tgatccgagc cagagcgcga acctgctggc ggaagcgaaa    1200
aaactgaacg atgcgcaggc gccgaaagtc gacaacaaat taataagga  acaacaaaac    1260 gccttctacg aaattctcca tctacccaat cttaatgaag agcagcgcaa cgcttttatt    1320
caatcgctta aggacgatcc cagccaatcg gcaaatcttc tggctgaagc taaaaagctt    1380
aatgacgcgc aagctcctaa agtggacccg tcaaaagatt ccaaagccca ggtaagtgca    1440
```

```
gctgaagcag gcataacggg aacatggtac aatcaactgg gaagcacgtt tatcgtaaca       1500
gcaggagcgg acggagcgtt gacaggcaca tacgaatctg ccgttggaaa cgcagaatcg       1560
cgttacacac ttacaggtag atacgattca gcaccggcta ccgatggaag cggaactgca       1620
ttgggatgga gagtggcttg gaaaaacaac tatagaaatg cgcatagcgc cacgacatgg      1680
tctggccaat acgtcggagg agcagaagct agaatcaata cacaatggac attaacgagc      1740
gggactacag aagcaaatgc ctggaaatcg acgttaagag gtcatgatac ctttaccaaa      1800
gtaaagccgt ccgcagcatc aattgatgca gcgaagaaag caggagtgaa taacggtaat      1860
cctttggatg cagtgcaaca atagtcgcta gcggccgcgt cgactagaag agcagagagg      1920
acggatttcc tgaaggaaat ccgttttttt attttgcccg tcttataaat ttcgttgaga      1980
tcttgatcat cgataagctt ggcgtaatca tggtcatagc tgtttcctgt gtgaaattgt      2040
tatccgctca caattccaca caacatacga gccggaagca taaagtgtaa agcctggggt      2100
gcctaatgag tgagctaact cacattaatt gcgttgcgct cactgcccgc tttccagtcg      2160
ggaaacctgt cgtgccagct gcattaatga atcggccaac gcgcgggag aggcggtttg       2220 cgtattgggc gctcttccgc ttcctcgctc actgactcgc tgcgctcggt cgttcggctg      2280
cggcgagcgg tatcagctca ctcaaaggcg gtaatacggt tatccacaga atcaggggat      2340
aacgcaggaa agaacatgtg agcaaaaggc cagcaaaagg ccaggaaccg taaaaaggcc      2400
gcgttgctgg cgttttttcca taggctccgc cccctgacg agcatcacaa aaatcgacgc       2460
tcaagtcaga ggtggcgaaa cccgacagga ctataaagat accaggcgtt ccccctgga       2520 agctccctcg tgcgctctcc tgttccgacc ctgccgctta ccggatacct gtccgccttt      2580
ctcccttcgg gaagcgtggc gctttctcaa tgctcacgct gtaggtatct cagttcggtg      2640
taggtcgttc gctccaagct gggctgtgtg cacgaacccc ccgttcagcc cgaccgctgc      2700
gccttatccg gtaactatcg tcttgagtcc aacccggtaa gacacgactt atcgccactg      2760
gcagcagcca ctggtaacag gattagcaga gcgaggtatg taggcggtgc tacagagttc      2820
ttgaagtggt ggcctaacta cggctacact agaaggacag tatttggtat ctgcgctctg      2880
ctgaagccag ttaccttcgg aaaaagagtt ggtagctctt gatccggcaa acaaaccacc      2940
gctggtagcg gtggtttttt tgtttgcaag cagcagatta cgcgcagaaa aaaggatct       3000 caagaagatc ctttgatctt ttctacgggg tctgacgctc agtggaacga aaactcacgt      3060
taagggattt tggtcatgag attatcaaaa aggatcttca cctagatcct tttaaattaa      3120
aaatgaagtt ttaaatcaat ctaaagtata tatgagtaaa cttggtctga cagttaccaa      3180
tgcttaatca gtgaggcacc tatctcagcg atctgtctat ttcgttcatc catagttgcc      3240
tgactccccg tcgtgtagat aactacgata cgggagggct taccatctgg ccccagtgct      3300
gcaatgatac cgcgagaccc acgctcaccg gctccagatt tatcagcaat aaaccagcca      3360
gccgaagggg ccgagcgcag aagtggtcct gcaactttat ccgcctccat ccagtctatt      3420
aattgttgcc gggaagctag agtaagtagt tcgccagtta atagtttgcg caacgttgtt      3480
gccattgcta caggcatcgt ggtgtcacgc tcgtcgtttg gtatggcttc attcagctcc      3540
ggttcccaac gatcaaggcg agttacatga tcccccatgt tgtgcaaaaa agcggttagc      3600
tccttcggtc ctccgatcgt tgtcagaagt aagttggccg cagtgttatc actcatggtt      3660
atggcagcac tgcataattc tcttactgtc atgccatccg taagatgctt ttctgtgact      3720
ggtgagtact caaccaagtc attctgagaa tagtgtatgc ggcgaccgag ttgctcttgc      3780
ccggcgtcaa tacgggataa taccgcgcca catagcagaa ctttaaaagt gctcatcatt      3840
```

```
ggaaaacgtt cttcggggcg aaaactctca aggatcttac cgctgttgag atccagttcg    3900
atgtaaccca ctcgtgcacc caactgatct tcagcatctt ttactttcac cagcgtttct    3960
gggtgagcaa aaacaggaag gcaaaatgcc gcaaaaaagg gaataagggc gacacggaaa    4020
tgttgaatac tcatactctt cctttttcaa tattattgaa gcatttatca gggttattgt    4080
ctcatgagcg gatacatatt tgaatgtatt tagaaaaata aacaataggg gttccgcgc    4140 acatttcccc gaaaagtgcc acctgacgtc taagaaacca ttattatcat gacattaacc    4200
tataaaaata ggcgtatcac gaggccctt cgtc                                 4234
```

<210> SEQ ID NO 35
<211> LENGTH: 6453
<212> TYPE: DNA
<213> ORGANISM: Artificial Sequence
<220> FEATURE:
<223> OTHER INFORMATION: plasmid sequence pMOL2746b

<400> SEQUENCE: 35

```
gaattcagat ctaaagataa tatctttgaa ttgtaacscc cctcaaaagt aagaactaca      60 aaaaagaat acgttatata gaaatatgtt tgaaccttct tcagattaca aatatattcg     120
gacggactct acctcaaatg cttatctaac tatagaatga catacaagca caaccttgaa     180
aatttgaaaa tataactacc aatgaacttg ttcatgtgaa ttatcgctgt atttaattt     240 ctcaattcaa tatataatat gccaatacat tgttacaagt agaaattaag acacccttga     300
tagccttact atacctaaca tgatgtagta ttaaatgaat atgtaaatat atttatgata     360
agaagcgact tatttataat cattacatat ttttctattg gaatgattaa gattccaata     420
gaatagtgta taaattattt atcttgaaag gagggatgcc taaaaacgaa gaacattaaa     480
aacatatatt tgcaccgtct aatggattta tgaaaaatca tttatcagt ttgaaaatta      540 tgtattatgg ccacattgaa agggggaggag aatcatgaaa caacaaaaac ggctttacgc     600
ccgattgctg acgctgttat ttgcgctcat cttcttgctg cctcattctg cagcagcggc     660
ggataacaaa tttaacaaag aacagcagaa cgcgttttat gaaatcctgc atctgccgaa     720
cctgaacgaa gaacagcgca acgcgtttat ccagagcctg aaagatgatc cgagccagag     780
cgcgaacctg ctggcggaag cgaaaaaact gaacgatgcg caggcgccga aagtcgacaa     840
caaatttaat aaggaacaac aaaacgcct ctacgaaatt ctccatctac ccaatcttaa      900
tgaagagcag cgcaacgctt ttattcaatc gcttaaggac gatcccagcc aatcggcaaa     960
tcttctggct gaagctaaaa agcttaatga cgcgcaagct cctaaagtgg acccgtcaaa    1020
agattccaaa gcccaggtaa gtgcagctga agcaggcata acgggaacat ggtacaatca    1080
actgggaagc acgtttatcg taacagcagg agcggacgga gcgttgacag gcacatacga    1140
atctgccgtt ggaaacgcag aatcgcgtta cacacttaca ggtagatacg attcagcacc    1200
ggctaccgat ggaagcggaa ctgcattggg atggagagtg gcttggaaaa caactatag     1260 aaatgcgcat agcgccacga catggtctgg ccaatacgtc ggaggagcag aagctagaat    1320
caatacacaa tggacattaa cgagcgggac tacagaagca aatgcctgga atcgacgtt     1380 aagaggtcat gatacctta ccaaagtaaa gccgtccgca gcatcaattg atgcagcgaa     1440
gaaagcagga gtgaataacg gtaatccttt ggatgcagtg caacaatagt cgctagcggc    1500
cgcgtcgact agaagagcag agaggacgga ttttcctgaag gaaatccgtt tttttatttt    1560
gcccgtctta taaatttcgt tgagatctac gcgtccatgg gctagcgcgg ccgcgtcgac    1620
```

```
aggcctctttt gattacatttt tataattaat tttaacaaag tgtcatcagc cctcaggaag    1680
gacttgctga cagtttgaat cgcataggta aggcggggat gaaatggcaa cgttatctga    1740
tgtagcaaag aaagcaaatg tgtcgaaaat gacggtatcg cgggtgatca atcatcctga    1800
gactgtgacg gatgaattga aaagcttgt  tcattccgca atgaaggagc tcaattatat    1860
accgaactat gcagcaagag cgctcgttca aaacagaaca caggtcgtca agctgctcat    1920
actggaagaa atggatacaa cagaaccta ttatatgaat ctgttaacgg gaatcagccg     1980
cgagctggac cgtcatcatt atgctttgca gcttgtcaca aggaaatctc tcaatatcgg    2040
ccagtgcgac ggcattattg cgacggggtt gagaaaagcc gattttgaag ggctcatcaa    2100 ggttttgaa  aagcgtgtcg ttgtattcgg gacgtcgatt cacaaaaata ggcacacgaa    2160
aaacaagtaa gggatgcagt ttatgcatcc cttaacttac ttattaaata atttatagct    2220
attgaaaaga gataagaatt gttcaaagct aatattgttt aaatcgtcaa ttcctgcatg    2280
ttttaaggaa ttgttaaatt gattttttgt aaatattttc ttgtattctt gttaaaccca    2340
tttcataacg aaataattat acttttgttt atctttgtgt gatattcttg atttttttct    2400
acttaatctg ataagtgagc tattcacttt aggtttagga tgaaaatatt ctcttggaac    2460
catacttaat atagaaatat caacttctgc cattaaaagt aatgccaatg agcgttttgt    2520
atttaataat cttttagcaa acccgtattc cacgattaaa taaatctcat tagctatact    2580
atcaaaaaca attttgcgta ttatatccgt acttatgtta taaggtatat taccatatat    2640
tttataggat tggtttttag gaaatttaaa ctgcaatata tccttgttta aaacttggaa    2700
attatcgtga tcaacaagtt tattttctgt agttttgcat aatttatggt ctatttcaat    2760
ggcagttacg aaattacacc tctttactaa ttcaagggta aaatggcctt ttcctgagcc    2820
gatttcaaag atattatcat gttcatttaa tcttatattt gtcattattt tatctatatt    2880
atgttttgaa gtaataaagt tttgactgtg ttttatattt ttctcgttca ttataaccct    2940
ctttaatttg gttatatgaa ttttgcttat taacgattca ttataaccac ttattttttg    3000
tttggttgat aatgaactgt gctgattaca aaaatactaa aaatgcccat attttttcct    3060
ccttataaaa ttagtataat tatagcacga gctctgataa atatgaacat gatgagtgat    3120
cgttaaattt atactgcaat cggatgcgat tattgaataa aagatatgag agatttatct    3180
aatttctttt ttcttgtaaa aaagaaaagt tcttaaaggt tttatagttt tggtcgtaga    3240
gcacacggtt taacgactta attacgaagt aaataagtct agtgtgttag actttatgaa    3300
atctatatac gttatatat  atttattatc cggaggtgta gcatgtctca ttcaattttg    3360
agggttgcca gagttaaagg atcaagtaat acaaacggga tacaaagaca taatcaaaga    3420
gagaataaaa actataataa taaagacata aatcatgagg aaacatataa aaattatgat    3480
ttgattaacg cacaaaatat aaagtataaa gataaaattg atgaaacgat tgatgagaat    3540
tattcaggga aacgtaaaat tcggtcagat gcaattcgac atgtggacgg actggttaca    3600
agtgataaag atttctttga tgatttaagc ggagaagaaa tagaacgatt ttttaaagat    3660
agcttggagt ttctagaaaa tgaatacggt aaggaaaata tgctgtatgc gactgtccat    3720
ctggatgaaa gagtcccaca tatgcacttt ggttttgtcc ctttaacaga ggacgggaga    3780
ttgtctgcaa aagaacagtt aggcaacaag aaagacttta ctcaattaca agatagattt    3840
aatgagtatg tgaatgagaa aggttatgaa cttgaaagag gcacgtccaa agaggttaca    3900
gaacgagaac ataaagcgat ggatcagtac aagaaagata ctgtatttca taaacaggaa    3960
ctgcaagaag ttaaggatga gttacagaag gcaaataagc agttacagag tggaatagag    4020
```

```
catatgaggt ctacgaaacc ctttgattat gaaaatgagc gtacaggttt gttctctgga    4080
cgtgaagaga ctggtagaaa gatattaact gctgatgaat tgaacgcct  gcaagaaaca    4140
atctcttctg cagaacggat tgttgatgat tacgaaaata ttaagagcac agactattac    4200
acagaaaatc aagaattaaa aaaacgtaga gagagtttga agaagtagt  gaatacatgg    4260
aaagaggggt atcacgaaaa aagtaaagag gttaataaat taaagcgaga gaatgatagt    4320
ttgaatgagc agttgaatgt atcagagaaa tttcaagcta gtacagtgac tttatatcgt    4380
gctgcgaggg cgaatttccc tgggtttgag aaagggttta ataggcttaa agagaaattc    4440
tttaatgatt ccaaatttga gcgtgtggga cagtttatgg atgttgtaca ggataatgtc    4500
cagaaggtcg atagaaagcg tgagaaacag cgtacagacg atttagagat gtagaggtac    4560
ttttatgccg agaaaacttt ttgcgtgtga cagtccttaa aatatactta gagcgtaagc    4620
gaaagtagta gcgacagcta ttaactttcg gtttcaaagc tctaggattt ttaatggacg    4680
cagcgcatca cacgcaaaaa ggaaattgga ataaatgcga aatttgagat gttaattaaa    4740
gacctttttg aggtcttttt ttcttagatt tttggggtta tttaggggag aaaacatagg    4800
ggggtactac gacctccccc ctaggtgtcc attgtccatt gtccaaacaa ataaataaat    4860
attgggtttt taatgttaaa aggttgtttt ttatgttaaa gtgaaaaaaa cagatgttgg    4920
gaggtacagt gatggttgta gatagaaaag aagagaaaaa agttgctgtt actttaagac    4980
ttacaacaga agaaaatgag atattaaata gaatcaaaga aaaatataat attagcaaat    5040
cagatgcaac cggtattcta ataaaaaaat atgcaaagga ggaatacggt gcattttaaa    5100
caaaaaaaga tagacagcac tggcatgctg cctatctatg actaaatttt gttaagtgta    5160
ttagcaccgt tattatatca tgagcgaaaa tgtaataaaa gaaactgaaa acaagaaaaa    5220
ttcaagagga cgtaattgga catttgtttt atatccagaa tcagcaaaag ccgagtggtt    5280
agagtatttta aaagagttac acattcaatt tgtagtgtct ccattacatg atagggatac    5340
tgatacagaa ggtaggatga aaaaagagca ttatcatatt ctagtgatgt atgagggtaa    5400
taaatcttat gaacagataa aaataattac agaagaattg aatgcgacta ttccgcagat    5460
tgcaggaagt gtgaaaggtc ttgtgagata tatgcttcac atggacgatc ctaataaatt    5520
taaatatcaa aaagaagata tgatagttta tggcggtgta gatgttgatg aattattaaa    5580
gaaaacaaca acagatagat ataaattaat taaagaaatg attgagttta ttgatgaaca    5640
aggaatcgta gaatttaaga gtttaatgga ttatgcaatg aagtttaaat ttgatgattg    5700
gttcccgctt ttatgtgata ctcggcgta  tgttattcaa gaatatataa aatcaaatcg    5760
gtataaatct gaccgataga ttttgaattt aggtgtcaca agacactctt ttttcgcacc    5820
agcgaaaact ggtttaagcc gactgcgcaa aagacataat cgactctaga ggatcccgg     5880
gtaccgagct ctgccttta  gtccagctga tttcactttt tgcattctac aaactgcata    5940
actcatatgt aaatcgctcc ttttaggtg  gcacaaatgt gaggcatttt cgctctttcc    6000
ggcaaccact tccaagtaaa gtataacaca ctatacttta tattcataaa gtgtgtgctc    6060
tgcgaggctg tcggcagtgc cgaccaaaac cataaaacct ttaagaccct tcttttttt     6120
acgagaaaaa agaaacaaaa aaacctgccc tctgccacct cagcaaaggg gggttttgct    6180
ctcgtgctcg tttaaaaatc agcaagggac aggtagtatt ttttgagaag atcactcaaa    6240
aaatctccac ctttaaaccc ttgccaattt ttattttgtc cgtttgtct  agcttaccga    6300
aagccagact cagcaagaat aaaatttta  ttgtctttcg gttttctagt gtaacggaca    6360
```
aaaccactca aaataaaaaa gatacaagag aggtctctcg tatctttat tcagcaatcg      6420 cgcccgattg ctgaacagat taataatgag ctc                                  6453

<210> SEQ ID NO 36
<211> LENGTH: 62
<212> TYPE: DNA
<213> ORGANISM: Artificial Sequence
<220> FEATURE:
<223> OTHER INFORMATION: Primer

<400> SEQUENCE: 36
tcattctgca gcagcggcgg ataacaaatt taacaaagaa cagcagaacg cgttttatga     60
aa                                                                    62

<210> SEQ ID NO 37
<211> LENGTH: 52
<212> TYPE: DNA
<213> ORGANISM: Artificial Sequence
<220> FEATURE:
<223> OTHER INFORMATION: Primer

<400> SEQUENCE: 37
aactaagcgg ccgctagcga ctacacttta ggagcttgcg cgtcattaag ct             52

<210> SEQ ID NO 38
<211> LENGTH: 1062
<212> TYPE: DNA
<213> ORGANISM: Artificial Sequence
<220> FEATURE:
<223> OTHER INFORMATION: ORF of protein A fused to streptavidin

<400> SEQUENCE: 38
atgaaacaac aaaaacggct ttacgcccga ttgctgacgc tgttatttgc gctcatcttc     60
ttgctgcctc attctgcagc gcggcagac ccctccaagg actcgaaggc ccaggtctcg    120
gccgccgagg ccggcatcac cggcacctgg tacaaccagc tcggctcgac cttcatcgtg    180
accgcgggcg ccgacggcgc cctgaccgga acctacgagt cggccgtcgg caacgccgag    240
agccgctacg tcctgaccgg tcgttacgac agcgccccgg ccaccgacgg cagcggcacc    300
gccctcggtt ggacggtggc ctggaagaat aactaccgca acgcccactc cgcgaccacg    360
tggagcggcc agtacgtcgg cggcgccgag gcgaggatca acacccagtg gctgctgacc    420
tccggcacca ccgaggccaa cgcctggaag tccacgctgg tcggccacga caccttcacc    480
aaggtgaagc cgtccgccgc ctccatcgac gcggcgaaga aggccggcgt caacaacggc    540
aacccgctcg acgccgttca gcagtcgaca ttacttatat ctggtggcgt aacacctgct    600
gcaaatgctg cgcaacacga tgaagctcaa caaaatgctt tttatcaagt cttaaatatg    660
cctaacttaa atgctgatca acgcaatggt tttatccaaa gccttaaaga tgatccaagc    720
caaagtgcta cgttttaggg tgaagctcaa aaacttaatg actctcaagc tccaaaagct    780
gatgcgcaac aaaataactt caacaaagat caacaaagcg ccttctatga atcttgaac    840 atgcctaact taaacgaagc gcaacgtaac ggcttcattc aaagtcttaa agacgaccca    900
agccaaagca ctaacgtttt aggtgaagct aaaaaattaa acgaatctca agcaccgaaa    960
gctgataaca atttcaacaa agaacaacaa aatgctttct atgaaatctt gaatatgcct   1020
aacttaaacg aagaacaacg caatggtttc atccaaagct ta                      1062

<210> SEQ ID NO 39
<211> LENGTH: 354

```
<212> TYPE: PRT
<213> ORGANISM: Artificial Sequence
<220> FEATURE:
<223> OTHER INFORMATION: ProteinA streptavidin fusion protein

<400> SEQUENCE: 39

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ala Asp Pro Ser
            20                  25                  30

Lys Asp Ser Lys Ala Gln Val Ser Ala Ala Glu Ala Gly Ile Thr Gly
            35                  40                  45

Thr Trp Tyr Asn Gln Leu Gly Ser Thr Phe Ile Val Thr Ala Gly Ala
        50                  55                  60

Asp Gly Ala Leu Thr Gly Thr Tyr Glu Ser Ala Val Gly Asn Ala Glu
65                  70                  75                  80

Ser Arg Tyr Val Leu Thr Gly Arg Tyr Asp Ser Ala Pro Ala Thr Asp
                85                  90                  95

Gly Ser Gly Thr Ala Leu Gly Trp Thr Val Ala Trp Lys Asn Asn Tyr
            100                 105                 110

Arg Asn Ala His Ser Ala Thr Thr Trp Ser Gly Gln Tyr Val Gly Gly
            115                 120                 125

Ala Glu Ala Arg Ile Asn Thr Gln Trp Leu Leu Thr Ser Gly Thr Thr
        130                 135                 140

Glu Ala Asn Ala Trp Lys Ser Thr Leu Val Gly His Asp Thr Phe Thr
145                 150                 155                 160

Lys Val Lys Pro Ser Ala Ala Ser Ile Asp Ala Ala Lys Lys Ala Gly
                165                 170                 175

Val Asn Asn Gly Asn Pro Leu Asp Ala Val Gln Gln Ser Thr Leu Leu
            180                 185                 190

Ile Ser Gly Gly Val Thr Pro Ala Ala Asn Ala Ala Gln His Asp Glu
        195                 200                 205

Ala Gln Gln Asn Ala Phe Tyr Gln Val Leu Asn Met Pro Asn Leu Asn
        210                 215                 220

Ala Asp Gln Arg Asn Gly Phe Ile Gln Ser Leu Lys Asp Asp Pro Ser
225                 230                 235                 240

Gln Ser Ala Asn Val Leu Gly Glu Ala Gln Lys Leu Asn Asp Ser Gln
                245                 250                 255

Ala Pro Lys Ala Asp Ala Gln Gln Asn Asn Phe Asn Lys Asp Gln Gln
            260                 265                 270

Ser Ala Phe Tyr Glu Ile Leu Asn Met Pro Asn Leu Asn Glu Ala Gln
        275                 280                 285

Arg Asn Gly Phe Ile Gln Ser Leu Lys Asp Asp Pro Ser Gln Ser Thr
        290                 295                 300

Asn Val Leu Gly Glu Ala Lys Lys Leu Asn Glu Ser Gln Ala Pro Lys
305                 310                 315                 320

Ala Asp Asn Asn Phe Asn Lys Glu Gln Gln Asn Ala Phe Tyr Glu Ile
            325                 330                 335

Leu Asn Met Pro Asn Leu Asn Glu Glu Gln Arg Asn Gly Phe Ile Gln
        340                 345                 350

Ser Leu
```

US 9,376,463 B2

DUAL AFFINITY POLYPEPTIDES FOR PURIFICATION

CROSS-REFERENCE TO RELATED APPLICATIONS

This application is a continuation of U.S. application Ser. No. 12/740,940 filed Apr. 30, 2010, which is a 35 U.S.C. 371 national application of PCT/EP2008/065346 filed Nov. 12, 2008, which claims priority or the benefit under 35 U.S.C. 119 of European application no. 07120454.9 filed Nov. 12, 2007, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to a process for purification of a target biomolecule on a solid support comprising the steps: (a) contacting (i) a target biomolecule, (ii) a dual affinity polypeptide, and (iii) a solid support comprising a catching ligand.

BACKGROUND OF THE INVENTION

Recovery and purification of therapeutic proteins accounts for approximately 50% of the manufacturing cost of biological drugs. The general industrial purification process often includes a number of unit operation steps, like extraction, precipitation, as well as anion- and cation-exchange chromatography. Affinity chromatography is the preferred downstream process step due to its high recovery, yield and specificity, but the current cost and limitations of affinity chromatography is very substantial and in many cases prohibitive for a more general use of this unit operation. For a general description of conventional purification procedures including affinity chromatography see e.g. Jason and Rydén 1998 (Jason, J-C and Rydén, L., Protein Purification Principles, high-Resolution, Methods and Applications, 2nd edition, Wiley & sons Inc. New York, 1998).

Conventional affinity chromatography is in general characterized by having a capturing ligand immobilised to a solid phase matrix. The ligand reversibly binds a target molecule present in a fluid such as liquid culture medium or serum. Target molecules are recovered by dissociating the complex at eluting conditions. Commercially available affinity matrices are in a ready to use format including capturing ligands covalently attached to the matrices. In conventional affinity chromatography the dissociation constant, $K_D$, between the ligand and the target protein is in the range of about $10^{-5}$-$10^{-7}$M. Interactions with dissociation constants exceeding $10^{-10}$-$10^{-11}$M are often impossible to use, as the conditions required to dissociate the complex are then the same as those that will result in denaturation of the target proteins.

The prior art include alternative variations of affinity chromatography purification methods described in the literature (Wilchek, M. and Gorecki, M. (1973), A New Approach for isolation of Biologically Active Compounds by Affinity Chromatography: Isolation of Trypsin).

FEBS Letters. 31, 1, 149-152, describes antibodies immobilized on an insoluble material. The antibodies have affinity for a certain ligand attached to a complex of two or more proteins, and are independent of the chemical, physical and biological properties of the complex itself. The immobilized antibody matrix serves as means for concentrating the complex. The adsorbed complex can then be recovered from the column by elution. The authors use the trypsin enzyme reacted with dinitrophenylated soybean trypsin inhibitor (DNP-STI) to form the complex. The complex is adsorbed to anti DNP-column and eluted under conditions that dissociate the antigen-antibody binding. The affinity column is then ready for the next purification cycle. The target trypsin is obtained by separation of the trypsin enzyme—dinitrophenylated soybean trypsin inhibitor complex into its components in a later step.

This procedure is different from the present invention in that the affinity column is reusable and it is the binding between the immobilized agent and the linker that is dissociated during elution and not the bond between linker and target biomolecule.

Another concept described by Hammarbergh, B. et al., (Proc. Natl. Acad. Sci USA, 86, 4367-4371 (1989)), is a fusion protein affinity approach and its use to express recombinant human insulin-like growth factor II. The procedure relates to a recombinant target protein of interest (X) fused between two different affinity protein tails (A and B). The protein (X) has a protease-sensitive site. A cell lysate containing the recombinant tripartite fusion protein is first passed through an affinity column containing a tail B-specific ligand. A mixture of full-length protein and proteolytic fragments containing the C-terminal fusion protein region can thus be obtained. In a second passage through a tail A-specific affinity column, the degraded proteins flow through while full-length fusion protein is retained. After site-specific cleavage of the tails, the protein of interest (X) is obtained by passing the cleavage mixture through a mixed affinity column for tails A and B and collecting the flow-through. The authors describe a procedure to obtain the target protein by expressing the target protein as an integrated part in between a dual affinity protein construct.

This is different from the present invention as the described affinity procedure requires two different affinity columns and that the immobilized ligand on the column and the dual affinity fusion protein is dissociated to recover the target biomolecule. Following the elution step and a regeneration procedure, the affinity columns are ready for the next affinity purification cycle. The target protein is only part of the fusion protein and is obtained following enzymatic degrading steps.

In a review article by, Ford, C. F., Suominen, I, Glatz, C. E. (1991) Fusion Tails for the Recovery and Purification of Recombinant Proteins. Protein Expression and Purification, 2, 95-107, the authors discuss the applications and advantages of using fusion tail systems to promote efficient recovery and purification of recombinant proteins from crude cell extracts or culture media. In these systems, a target protein is genetically engineered to contain a C- or N-terminal polypeptide tail, which provides the biochemical basis for specificity in recovery and purification. Fusion tails are useful for enhancing recovery methods for industrial downstream processing. Nevertheless, for the purification of target proteins a site for specific enzymatic cleavage is included, allowing removal of the tail after recovery. The article describes the application of fusion proteins with one binding partner having affinity for the ligand immobilized on a matrix. The procedures include an enzymatic cleavage step to recover the target protein from the fusion tail as required.

This is different from the present invention as the described affinity procedure requires that the fusion protein is dissociated from the ligand immobilized on the column matrix to recover the protein. Following the elution step and a regeneration procedure, the affinity column is ready for the next affinity purification cycle. Also, different from the present invention is that the target protein is part of the fusion protein and is only obtained following an enzymatic processing step.

In Rigaut, G. et al. (1991) (A Generic Protein Purification Method for Protein Complex Characterization and Proteom Exploration. Nature Biotechnology, 17, 1030-1032), is described a generic procedure for purification of protein complexes using tandem affinity purification (TAP) tag. The purification requires one affinity step followed by an enzymatic step cleaving the first affinity tag from the complex and a second affinity purification step to recover the target protein complex from the protease. Overall, the method involves two binding partners in combination both for binding to a ligand immobilized to a column matrix and a protease cleavage step to expose the second binding partner.

This is different from the present invention as the described affinity procedure requires that the fusion protein is dissociated from the ligand immobilized on the column matrix to recover protein. Following the elution step and a regeneration procedure, the affinity column is ready for the next affinity purification cycle. Also, different from the present invention is that the target protein is part of the fusion protein and is obtained following an enzymatic processing step.

EP1529844 describes a method for altering the properties of a recombinant target protein involving co-expression of target protein and the binding partner. The target protein and the binding partner form a complex in the cell. The complex formation result in altered properties such as accumulation, stability and/or integrity, sub-cellular localization, post-translational modifications, purification, and phase partitioning behavior of natural or recombinant target proteins expressed in a host organism. The binding partner may provide an affinity tag that enables co-purification of the complex and the target protein contained therein.

This description is different from the present invention as it describes a co-expression of the binder and the target in order to form a complex in the cell. The disclosed method is for alteration of the target protein properties in general, whereas the present invention describes a dual affinity polypeptide specifically designed to facilitate a dedicated purification process, wherein the dual affinity polypeptides needs to possess specific binding properties.

Linder et al., (Linder, M., Nevanen, T., Söderholm, L., Bengs, O. and Teeri, T., 1998, Biotechnology and Bioengineering, 60(5): 642-647) describes the use of CBD in fusion-proteins for use as an affinity tag for purification. Some leakage from the column was observed.

Shpigel, E. et al. (Biotechnol. Appl. Biochem. (2000) 31, 197-203, "Expression, purification and application of Staphylococcal Protein A fused to cellulose-binding domain"), describes an example of purifying IgG using Protein A-CBD dual affinity polypeptide.

They claim that they save expensive coupling procedures by choosing immobilization of the Protein A functionality to a solid phase through the cellulose-binding domain (CBD) of a fusion protein. The fusion protein is immobilized on the column before adding the target.

Due to leakage problems this choice of dual affinity molecule is unsuitable for biopharmaceutical applications.

Sano et al. (U.S. Pat. No. 5,328,985) describes a fusion protein consisting of streptavidin and one or two immunoglobulin G (IgG) binding domains of protein A expressed in *Escherichia coli*. The strepavidin-protein A (ST-PA) fusion protein has functional biotin and IgG binding sites. Sano further describes complexes of the streptavidin-protein A fusion protein, a monoclonal antibody to bovine serum albumin (BSA) and biotinylated horseradish peroxidise. Sano also describes a method of labelling cell using the ST-PA fusion protein. Cells are incubated with an antibody to the cell surface antigen, Thy-1. The chimeric protein biotinylated marker complex is subsequently added to the cell suspension. This technique was used to deliver biotinylated FITC to the surface of the cells having Thy-1 antigens on their surface.

However, Sano does not describe or suggest using the ST-PA fusion protein as a tool for purification purposes nor does he describe a procedure of single use affinity chromatography column materials, nor recovery of a target protein.

WO 97/19957 describes an invention related to delivering toxins or nucleic acids into specific cell types using ST-PA fusion proteins for the purpose. Similar to Sano et al. (vide supra), an antibody recognise a surface antigen on the cell surface. The ST-PA binds to the antibody and facilitates a linkage to a biotinylated toxin bound to the biotin-binding site. However, it is not described or suggested to use the ST-PA fusion protein as a tool for purification purposes.

WO 01/95857 discloses a method and components for extracting toxic substances from mammalian blood. The method includes preparing an affinity column (extracorporeal device) and a procedure for extracorporeal extraction of toxic material from mammalian body fluids in connection with diagnosis or treatment of a mammalian condition or disease. The extracorporeal affinity column exemplified in the patent is made by coupling biotinylated entities to a matrix containing immobilized avidin. The biotinylated entity includes a part that binds strongly to the toxin in the mammalian blood. The toxic material is removed (i.e. immobilized but not recovered by elution from the column) from the blood following a conventional affinity chromatography procedure. The product from the flow through chromatography procedure is purified blood as the target (toxic materials) stays immobilized on the column after the process.

This is different from the present invention as it describes a procedure that bind the target tightly with high affinity in order to remove target from the product. The purification procedure is also different from the present invention as the product does not bind to the affinity column, but flows through and is collected as depleted from the toxic material (the target). The toxic material is not released or recovered.

WO 97/09068 discloses a method and chemical components that alter the equilibrium dissociation constant between two pairs of bio-molecules. The chemical component is a polymer that can be stimulated to change conformation and thus binding efficiency. The polymer is coupled e.g. to a specific site of the binding partner (the ligand) immobilised to the matrix of the affinity chromatography column. WO 97/09068 does not describe or suggest the use of a dual affinity component for affinity purification, nor recovering of target molecules.

In general, methods that will improve the capturing efficiency and simplify the purification process as well as reduce costs are desirable.

SUMMARY OF THE INVENTION

The present invention significantly improves and simplifies the downstream processing and lowers the cost of affinity chromatography processes in general. The present invention includes a generic capturing ligand immobilised to a matrix, a target biomolecule and a semi generic dual affinity polypeptide with different binding affinity toward the target and the capturing ligand respectively. The dual affinity polypeptide reacts with the target biomolecule to form a complex of medium binding affinity, and the complex binds non-covalently to a generic affinity matrix with a strong binding affinity. The target biomolecule is recovered by specific elution from the generic matrix leaving the dual affinity polypeptide attached to the capturing ligand on the matrix, due to the tight binding to the ligand preventing leakage from the solid phase matrix.

In a first aspect the present invention provides a process for purification of a target biomolecule, comprising the steps: (a) contacting (i) a target biomolecule, (ii) a dual affinity polypeptide, and (iii) a solid support comprising a catching ligand or dual affinity polypeptide binding site, wherein the ratio between the equilibrium dissociation constants of the dual affinity polypeptide, $[K_{D,t}/K_{D,s}]$, is at least $10^0$ at standard conditions; and (b) recovering the target biomolecule by elution.

In a second aspect the present invention provides a process for purification of a target biomolecule, comprising the steps: (a) contacting (i) a target polypeptide, (ii) a dual affinity polypeptide, and (iii) a solid support comprising a catching ligand, wherein the dual affinity polypeptide has an equilibrium dissociation constant, $K_{D,t}$ towards the target biomolecule in the range from $10^{-2}$ to $10^{-13}$ M, more particularly from $10^{-4}$ to $10^{-13}$ M at standard conditions, and wherein binding of the dual affinity polypeptide to the catching ligand on the solid support is provided by cleavage of a para-substituted benzyl guanine resulting in a thioether bond; and (b) recovering the target biomolecule by elution.

DETAILED DESCRIPTION OF THE INVENTION

In conventional affinity chromatography the capturing ligand is attached directly to the support. The main technical challenges are to optimize the entire system with regard to e.g. ligand coupling, nature of the support material, flow, backpressure and physical dimensions of the column. It should be understood that several of the technical limitations in high performance affinity columns are closely linked, making performance and cost optimization as well as scale up difficult. The ligand, in traditional affinity chromatography, preferably posses the following characteristics:
  a) The ligand should have chemical properties that allow easy covalent attachment to the matrix.
  b) The ligand must be able to form a reversible complex with the target molecule.
  c) The specificity of the ligand's affinity for the target molecule must be appropriate for the planned application.
  d) The dissociation constant for the ligand-target molecule complex under "loading conditions" should be strong enough to enable formation of stable complexes or to give sufficient retardation in the elution of the target molecule.
  e) It should be easy to dissociate the ligand from the target molecule by changing the conditions, e.g. pH or salt concentration, without irreversibly damaging either.
  Furthermore, in traditional affinity chromatography, the ligand is normally covalently attached to the matrix and is also the component binding to the target molecule.

The capacity and quality of purification is greatly influenced by the contact time between target and ligand in the affinity column, the so-called residence time.

In addition to the association rate of the target protein to an immobilized ligand, diffusion into the pores within the chromatography beads in the column and mass transfer of the protein from the solute will impact the dynamic binding capacity of a chromatography matrix.

The mass transfer of the target protein from the solute depends on a variety of factors, including type and degree of cross-linking, compressibility of the support material, the size of the pores and the physical size of the target protein.

Flow rates, protein concentrations, column length, temperature, buffer, conductivity, and pH can also influence on pore diffusion and the dynamic binding capacity of the adsorbent.

Due to the requirement for rapid development of downstream processes and regulatory constraints, the residence time for a particular type of biological product such as for example a therapeutic antibody is typically fixed in the early development. Therefore, often the flow rate in the large scale column with e.g. larger bed height is tried adjusted to maintain the desired residence time used during the small scale development.

Due to technical constraints and the major investment required to purchase process-scale chromatography equipment, the scale up of traditional high performance affinity chromatography is a major challenge.

The present invention suggests a more simple and flexible scale up process with less technical constraints.

Furthermore, conventional affinity chromatography is characterised by regeneration procedures to provide repeated uses of the column materials. These cleaning procedures require extensive validation to allow multiple uses of the column.

The present invention differs in several aspects from the conventional affinity chromatography e.g.
  the immobilized ligand binds tightly to the dual affinity polypeptide (DAP) in order to prevent dissociation at elution conditions
  it is intended for single use applications
  It is clear from the above that the role of the ligand in the present invention is to bind the DAP molecule and not the target molecule.

The attractive benefit of affinity chromatography is that it provides a large increase in purity with a minimal loss of target molecule material in a single unit operation. However, affinity chromatography is also characterised by the high cost prohibiting the use of large columns and thus favouring repetitive use of smaller columns. This leads to extended production processes and capacity loss proportional to the number of column reuses, increased loss and/or modification of the target molecule. In principle a typical affinity chromatography matrix can be used for up to 100 or more runs, but the average number of runs in manufacturing scale appears to be several fold lower. One of the reasons that the matrix is discarded long before the end of its theoretical lifespan is that the affinity columns used in manufacturing are dimensioned to process the entire fermentation batch in far less than 100 runs—in order to save cost, but also reduce the risk of contamination and handling failures. Rather than using the same matrix for several fermentation batches, the matrix may be discarded after processing of one fermentation batch, which leads to the relatively low number of average runs on an affinity matrix.

Controlling the flow rate through an affinity chromatography support is important in achieving binding. Flow rate through the column support is inextricably related to the efficiency of the separation; too fast a flow will cause the mobile phase to move past the beads faster than the diffusion time necessary to reach the internal bead volume.

For each application a flow rate can be selected to achieve an optimal balance between efficient binding and elution of the target protein and a fast separation. Gravity driven flow chromatography is very slow and resolution of the protein separation can be adversely affected by secondary diffusion effects. Therefore modern systems have active pumping to control flow rates and continuous monitoring of back pressure to ensure that the maximum operating back pressure is not being exceeded.

In conventional columns fouling is of major concern. Debris, proteins and salts can slowly build up fouling layers in the channels of high performance affinity chromatography supports resulting in changed flow rates, reduced mass transfer rates, increased back pressure and hidden and deactivated affinity ligands. Especially lipids and lipoproteins material can rapidly clog chromatography columns and it is often necessary to remove them before affinity purification. This is especially important for samples derived from ascites fluid.

This pre purification step can be done by precipitation steps with for example dextran sulphate and polyvinylpyrrolidine followed by centrifugation and dialysis or desalting. The step can result in the loss of 5-10% of the target protein.

Omitting the delipidation step may be possible for the affinity purification system of the present invention as the column is single use. This will result in a higher overall target recovery and a more efficient downstream processing workflow.

Because of the intended single use of the columns according to the invention the elution step is also simplified. As the support material of the invention is not to be reused, one can more freely select elution conditions. For example, it is possible to select any elution buffers with an unconventional high concentration of salt, strong chaotropes, organic solvents etc. which will allow the recovery of the intact target and leave the DAP molecule attached to the support. It is of no importance if the properties of the support material are irreversibly changed with respect to e.g. structure and flow characteristics and cannot be reused.

This flexibility in selecting elution conditions is often not possible when using traditional high-performance affinity purification systems as the internal structures and surfaces are highly optimized and sensitive to polymer swelling or precipitation. Additionally, due to the cost of traditional affinity columns, the operators can be reluctant to test new elution conditions further reducing the flexibility in elution optimization.

The traditional operation of affinity purification includes cycles of equilibration, sample loading, elution and cleaning-in-place (CIP).

The cleaning steps or sanitization protocols have to be designed for each specific target purification. As described above, a major concern during operation is the build up of fouling layers or cross contamination between runs.

The cleaning step often includes using chemically harsh buffers like 0.1 M NaOH/1 M NaCl or 0.1 M phosphoric acid in a combination with sodium chloride or ethanol, followed by regeneration. It is well established that in general the dynamic binding capacity decreases as the number of CIP cycles increases. Therefore, one needs to find an optimum between the quality of the purified target, the number of runs, CIP's and the size and cost of the particular column. Further, the change of purification quality needs to be monitored for most pharmaceutical purifications.

As suggested by the present invention, the cost of this quality validation and the optimization of the CIP and runs can be greatly reduced.

In the conventional affinity chromatography outlined above for purification of e.g. monoclonal antibodies, the capturing ligand (Protein A) is attached to a solid phase matrix and has the affinity towards the target biomolecule (monoclonal antibodies). The present invention provides advantages compared to conventional affinity purification technologies for the downstream processing industry due to lower costs, high specificity and ease of use without compromising the quality of the down stream process. An essential feature of the present invention is the use of a dual affinity polypeptide as a linker between the target molecule and the solid support comprising a ligand. These dual affinity polypeptides are particularly useful for the downstream processing of biopharmaceutical and diagnostic proteins and peptides.

The invention suggests the improvement of the entire method of affinity purification by eliminating several of the constraints in current systems.

By using the dual affinity polypeptide (DAP) and the generic supports of the invention, the majority of the above problems and limitations can be completely eliminated or reduced.

According to the present invention the dual affinity purification technology is characterized by a generic solid support, which in one embodiment is a solid phase matrix, plus ready-to-use specific dual affinity polypeptides serving as linker molecules. A dual affinity polypeptide reacts with the target biomolecule. The dual affinity polypeptide-target biomolecule complex subsequently connects non-covalently to a capturing ligand immobilized on a solid support by contacting the complex and the solid support. The target biomolecule is recovered by specific elution. The dual affinity polypeptide remains attached to the ligand on the solid support during elution.

In one aspect the present invention therefore relates to a process for purification of a target biomolecule, comprising the steps: (a) contacting (i) a target biomolecule, (ii) a dual affinity polypeptide, and (iii) a solid support comprising a catching ligand or dual affinity polypeptide binding site, wherein the ratio between the equilibrium dissociation constants of the dual affinity polypeptide, $[K_{D,t}/K_{D,s}]$, is at least $10^0$ at standard conditions; and (b) recovering the target biomolecule by elution.

The dual affinity polypeptide acts as the linking partner between the solid support and the target molecule. In one particular embodiment the affinity of the dual affinity polypeptide towards the immobilized ligand is stronger than the affinity towards the target molecule. Furthermore this difference in binding affinity, can be expressed as the ratio between the equilibrium dissociation constants. In one embodiment this ration is at least 1.

The dual affinity polypeptide according to the invention comprises at least two binding sites, of which one binding site has affinity for the ligand and another binding site has affinity for the target molecule. These binding sites are polypeptide based meaning that they comprise either complete proteins or fragments of proteins. Such fragments should at least comprise the part of the protein containing the binding site for the specific target. The dual affinity polypeptide could be a fusion polypeptide or could be two or more polypeptides chemically linked in any suitable way e.g. by a linker segment.

Therefore the present invention in further embodiments relates to a dual affinity polypeptide having an equilibrium dissociation constant towards a target biomolecule, $K_{D,t}$ in the range from $10^{-2}$ to $10^{-13}$ M, e.g. $10^{-8}$ M, and an equilibrium dissociation constant towards a catching ligand, $K_{D,s}$ in the range from $10^{-9}$ to $10^{-16}$ M, e.g. $10^{-10}$ M, and at the same time the ratio, $K_{D,t}/K_{D,s}$, should be matched such that the ratio is at least $10^0$, more particularly at least $10^1$, more particularly $10^2$, more particularly $10^3$ and even more particularly $10^4$.

The above in other words means that binding of DAP to the target is in preferred embodiments weaker than binding of DAP to the ligand.

Particularly the said dual affinity polypeptide has an equilibrium dissociation constant, $K_{D,t}$ towards the target polypeptide in the range from $10^{-4}$ to $10^{-13}$ M, more particularly in the range from $10^{-6}$ to $10^{-13}$ M, and an equilibrium dissociation constant, $K_{D,s}$ towards the catching ligand in the range from $10^{-9}$ to $10^{-16}$ M, more particularly in the range from $10^{-11}$ to $10^{-16}$ M.

In general the binding towards the ligand or the column cannot be too strong. Therefore the value at the upper end of the range is not important in respect of $K_{D,s}$.

In the context of the present invention the equilibrium dissociation constant are measured according to the reaction:

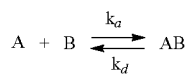

A and B represents the binding partners: the target biomolecule and the dual affinity polypeptide or the dual affinity polypeptide and the catching ligand immobilized on the solid phase matrix.

The rate constants for the reaction above represent the rate at which the two molecules A and B associates and dissociates $$\text{Dissociation rate} - \frac{d[AB]}{dt} = k_d[AB]$$

$$\text{Association rate:} \frac{d[AB]}{dt} = k_a[A][B]$$

When the rates are equal at equilibrium $k_a[A][B]=k_d[AB]$, which gives $$\frac{k_d}{k_a} = \frac{[A][B]}{[AB]} = K_D$$

$$\frac{k_a}{k_d} = \frac{[AB]}{[A][B]} = K_A$$

The candidate binding domains to be employed in the dual affinity polypeptide should be evaluated according to the apparent equilibrium dissociation constants based on the total binding affinity of each of the dual affinities in a given DAP molecule irrespective of whether it contains one or several binding domains for each specificity (target/capturing ligand). If e.g. A and B represent protein A (has four to five binding domains) and avidin (having four binding sites) respectively the above ranges should apply for one protein A molecule fused to one avidin molecule. However, this does not exclude the possibility that e.g. the DAP molecule could be composed of several binding candidates for the target and several candidates for the ligand on the matrix. The DAP could e.g. in another embodiment consist of 3 protein A molecules linked to one or more avidin molecules. Therefore the specified ranges as defined above should in the context of the present invention be evaluated based on the apparent binding constants for the binding domains in common.

In the context of the present invention the specified equilibrium dissociation constants are determined by surface plasmon resonance (SPR) technology using a Biacore Instrument as illustrated in detail in the examples. The conditions described herein represent the standard conditions. As a suitable starting point for selecting different binding domains to be combined in the DAP molecule published $K_D$'s may be used.

The two binding pairs should be selected based on the $K_D$'s during specific binding conditions, but also considering the planned elution conditions, when the target is recovered and the DAP molecule remains on the support.

As described above determination of dissociation affinities of various binding domains in the context of a DAP molecule was accomplished by using surface plasmon resonance (SPR). Such evaluation can be done with the Biacore system. Biacore has commercial instrumentation where measurements based on SPR make determinations on protein-protein interactions. The evaluation was conducted having the complete DAP immobilized on the sensor chip used in the Biacore instrument. The Biacore system defines the characteristics of proteins in terms of their specificity of interaction with other molecules, the rates at which they interact (association and dissociation), and their affinity (how tightly they bind to another molecule). This technique has been described e.g. for determining the binding interactions between specific antibodies and their target (see e.g. Ronnmark, 2002, Eur. J. Biochem., 269: 2647-2655).

In the examples below several DAP candidates have been evaluated and their binding affinities under standard conditions (as described in the examples) have been measured for the complete DAP. Other methods may also be used, however, results may then differ. A list of alternative methods has been described below.

Quantitative measurement of non-covalent protein-ligand interactions is well known. The methods suited for quantitative measurement of binding constants of particular relevance for the present invention include various versions of surface plasmon resonance (SPR) and circular dichroism (CD).

Other methods include mass spectrometry methods for dynamic titrations like ESIMS titration, HPLC-ESI-MS titration or MALDI-SUPREX titration.

Other methods are based on determining the dissociation constant of a ligand at a binding site indirectly by competitive displacement of a radioactive ligand or by measurement of NMR chemical shift as function of concentration, fluorescence spectroscopy analysis of e.g. signal quenching, X-ray crystallographic measurement of the ligand occupancy, isothermal calorimetry (ITC) or enzyme inhibition.

Yet other methods use labeled ligands, for example capillary electrophoresis with laser-induced fluorescence detection of enzyme labeled ligands.

Alternatively, binding constants can be found from computational techniques by using de novo design, data mining and sophisticated algorithms.

In the context of the present invention the appropriate ranges for the equilibrium dissociation constants as specified in the claims should apply to the complete dual affinity polypeptide and not to the individual binding parts measured separately.

Moreover, if a single candidate binding domain has a weaker binding affinity towards the target or ligand than required according to the present invention, it still could be applicable by combining several such candidate binding domains into one DAP.

This is due to the valence effect. It is possible to obtain an increased binding strength due to an avidity gain. Single domains with a low intrinsic affinity combined into multimers often generates avidity effects which lead to slower dissociation rates and increased functional affinities by more than 100 fold (MacKenzie, C. R. et al (1996), Analysis by surface plasmon resonance of the influence of valence on the ligand binding affinities and kinetics of and anti carbohydrate antibody. Journal of Biological Chemistry, 271, 1527-1533). It is possible to measure effects from monovalent and bivalent bindings, but at higher binding valences the situation becomes so complex that it is impossible to distinguish between different binding valances. Nevertheless relative data can be obtained and are used in the context of the present invention The invention provides a purification procedure wherein the first reaction between the target molecule and the dual affinity polypeptide in one particular embodiment can be completed in free solution. Reaction binding kinetics is about 1000 times faster in free solution compared to interface reactions (Nygren, H. and Stenberg, M. (1989) Immunochemistry at interfaces. Immunology, 66, 321-327).

The target molecule-dual affinity polypeptide complexes are subsequently presented to and bind efficiently to the ligand on the solid support. The strong binding (fast association rate and slow dissociation rate of the ligand towards the dual affinity polypeptide) depletes the mobile phase of target-DAP complexes. The target molecules are recovered from solution through this sequential procedure facilitated by the second binding functionality of the dual affinity polypeptide.

Due to the described differences in equilibrium dissociation constants the target polypeptide can be efficiently eluted without eluting the dual affinity polypeptide. Elution can in one embodiment be performed by changing either pH, ionic strength or chaotropic ions in solution, or any combination thereof.

The $K_D$ value can be influenced by changing conditions like pH, ionic strength, temperature and polar properties. Unfortunately, the literature values for $K_D$ are not always listed at relevant elution conditions. Though, the skilled in the art will be able to find elution conditions which will only break the weakest binding without disturbing the stronger binding in cases were the binding to the solid matrix is sufficiently strong (i.e. $K_{D,s} < 10^{-9}$ M and the ratio between $K_D$ values is at least 1 when measured at standard binding conditions).

The criteria for selecting the target specific binding pairs of the invention resemble those for the traditional affinity chromatography with regard to dissociation constant, specificity, binding and possible elution conditions. However, since elution conditions are usually different from the conditions applied when measuring $K_D$'s on the Biacore instrument in the present invention the limits set for the applicable ranges of the two distinct binding affinities of the DAP has been determined under standard conditions, which equals the conditions used in the examples.

The criteria for selecting the specific ligand binding domains of the invention are somewhat different from the criteria used in the traditional affinity chromatography, as the DAP molecule is not to be eluted from the support.

Binding domains which are specific and strong, but cannot be broken under normal elution conditions are not suited for traditional affinity chromatography. Such binding domains can be used in the present invention. Examples include the very specific biotin-Streptavidin binding, which for most practical applications cannot be reversed under elution conditions and consequently is well suited as one of the binding pairs of the invention.

In general, the binding between DAP and the ligand should be stronger than the binding between DAP and the target and strong enough to prevent leakage of the DAP molecule from the support during elution of the target.

Preferred ligand-DAP binding pairs are strong and exhibit no or little reduction in binding strength due to changing pH, ionic strength, solvents, chaotropic agents, temperature etc.

It should be clear that when changing the scale of purification, using the system of the invention, the amount of DAP added is adjusted to the amount and concentration of target protein. As the DAP molecule can be supplied as a concentrate, the binding conditions can be adjusted with respect to e.g. pH and salts. Also, the temperature and time can be selected to give the best binding and subsequently purification.

The size and capacity of the generic column is selected to be large enough to capture the DAP molecules. Potentially several columns are used in parallel or in a bundle.

If purifying another target, another appropriate DAP molecule is selected. The same or another column can be used.

In one embodiment the dual affinity polypeptide is a fusion polypeptide. Such fusion polypeptides can either be prepared by chemically linking two appropriate proteins or alternatively in another embodiment the fusion protein can be synthesized as a recombinant polypeptide. The fusion polypeptide can be linked in any suitable way e.g. by a linker segment, and the fusion polypeptide should at least comprise the binding domains of the selected proteins. The linker peptide should be selected in such a way that it is not unstable resulting in degradation. The linker could e.g. be a highly O-glycosylated linker as linkers between catalytic domains and carbohydrate binding domains known from fungal carbohydrases, or it could be proline rich linkers.

The dual affinity polypeptide comprises at least one binding domain capable of binding to the target biomolecule with the desired binding specificity as described. The binding domain can be comprised in the complete protein or it can be a fragment of the protein which has retained its binding specificity. Many proteins have been described in the literature displaying affinity towards biomolecules, e.g. peptides, proteins, DNA, RNA, carbohydrates, and all such proteins or fragments thereof are potentially useful in the context of the present invention as candidates for the dual affinity polypeptide.

The said binding domain directed towards the target biomolecule can in one embodiment therefore be selected from but not limited to the group consisting of protein A, protein A fragments, protein A derived domains (e.g. domains known as an Affibody®), antibodies, antibody fragments, lipocalins, and lectins.

Combinatorial protein engineering has been applied to develop artificial proteins that can bind to selected targets with high affinity and be used as alternatives to antibodies (Nygren, P.-Å. & Skerra, A. (2004). Binding proteins from alternative scaffolds. J. Immunol. Methods, 290, p. 3-28; Binz, H. K. & Plückthun, A. (2005). Engineered proteins as specific binding reagents. Curr. Opin. Biotech. 16, p. 459-469). In the context of the present invention the term "affibody" defines a class of engineered proteins selected for their specific binding activity towards a desired target and based on the Z domain, which is a 58 residue three-helical bundle derived by a single amino acid substitution in the B domain of staphylococcal protein A (SPA) (Nilsson, B., Moks, T., Jansson, B., Abrahmsén, L., Elmblad, A., Holmgren, E. et al. (1987) Protein Eng. 1, p. 107-113). The Z domain binds to the Fc region of immunoglobulins as do the five homologous SPA domains, but unlike the parental domain it does not bind to the Fab region. Such affibodies are examples of a protein A derived binding domain.

The dual affinity polypeptide also comprises at least one binding domain capable of binding to the catching ligand immobilized on the solid support. This second binding domain can be comprised in the complete protein or it can be a fragment of the protein which has retained its binding specificity. In one embodiment the second binding domain is selected from but not limited to the group consisting of avidin, streptavidin, neutravidin, steroid receptor, antibody, antibody fragment, amyloglucosidase (AMG), enzyme domain (e.g. cellulose binding domain, CBD), lipocalins, and lectins. As stated above these candidates, for the second binding domain, are meant as examples illustrating the invention, however, these examples should not be seen as the only usable combinations.

In one embodiment the antibody is selected from the group consisting of Llama and camel antibodies.

In a particular embodiment the dual affinity polypeptide according to the invention comprises at least one binding domain of protein A fused to at least one biotin binding domain of avidin, streptavidin or neutravidin.

In a particular embodiment the dual affinity polypeptide according to the invention comprises at least one binding domain of a protein A derived binding domain fused to at least one biotin binding domain of avidin, streptavidin or neutravidin.

In another particular embodiment the dual affinity polypeptide comprises at least one binding domain of an affibody fused to at least one biotin binding domain of avidin, streptavidin or neutravidin.

In another particular embodiment the dual affinity polypeptide comprises at least one binding domain of an antibody fused to at least one biotin binding domain of avidin, streptavidin or neutravidin.

In another particular embodiment the dual affinity polypeptide comprises at least one binding domain of protein A fused to AMG, CBD or (VhhRR6(R2)).

In another particular embodiment the dual affinity polypeptide comprises at least one binding domain of a protein A derived binding domain fused to AMG, CBD or (VhhRR6(R2)).

In another particular embodiment the dual affinity polypeptide comprises at least one binding domain of an affibody fused to AMG, CBD or (VhhRR6(R2)).

In another particular embodiment the dual affinity polypeptide comprises at least one binding domain of an antibody fused to AMG, CBD or (VhhRR6(R2)).

The dual affinity polypeptide can as illustrated in the examples be linked chemically; however, a more cost efficient way to produce the dual affinity polypeptide would be to express it as a recombinant fusion protein.

In one embodiment of the invention, the fusion polypeptide is produced as a recombinant polypeptide.

Another possibility also envisioned would be to co-express the fusion protein and the target biomolecule in the host cell making it possible to load the crude cell culture extract directly on the solid support.

In a further embodiment the target biomolecule and the DAP is expressed separately but in the same type of host cell.

In a particular embodiment the fusion protein is expressed as a recombinant protein, particularly the fusion protein is in one embodiment recombinant Streptavidin linked to protein A. Such fusion protein can be produced intracellular in *E. coli* as described in Sano (T. Sano and C. R. Cantor (1991) Bio-Technology 9 p 1378-1381), preferentially using the construct pTSAPA-2 carrying two IgG binding domains. However this construct is not industrially feasible as intracellular production with recovery of inclusion bodies in *E. coli* do not give industrially relevant yields and the production process is highly complex. A process based on a secreted fusion produced in e.g. *Bacillus* or *Aspergillus* is of much higher industrial relevance.

The nucleotide sequence encoding the fusion protein according to the invention may preferably be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like.

A conditionally essential gene may function as a non-antibiotic selectable marker. Non-limiting examples of bacterial conditionally essential non-antibiotic selectable markers are the dal genes from *Bacillus subtilis*, *Bacillus licheniformis*, or other Bacilli, that are only essential when the bacterium is cultivated in the absence of D-alanine. Also the genes encoding enzymes involved in the turnover of UDP-galactose can function as conditionally essential markers in a cell when the cell is grown in the presence of galactose or grown in a medium which gives rise to the presence of galactose. Non-limiting examples of such genes are those from *B. subtilis* or *B. licheniformis* encoding UTP-dependent phosphorylase (EC 2.7.7.10), UDP-glucose-dependent uridylyltransferase (EC 2.7.7.12), or UDP-galactose epimerase (EC 5.1.3.2). Also a xylose isomerase gene such as xylA, of Bacilli can be used as selectable markers in cells grown in minimal medium with xylose as sole carbon source. The genes necessary for utilizing gluconate, gntK, and gntP can also be used as selectable markers in cells grown in minimal medium with gluconate as sole carbon source. Other examples of conditionally essential genes are known in the art. Antibiotic selectable markers confer antibiotic resistance to such antibiotics as ampicillin, kanamycin, chloramphenicol, erythromycin, tetracycline, neomycin, hygromycin or methotrexate.

Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, Gene 98:61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into the host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The present invention also relates to recombinant host cells, comprising a polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be a unicellular microorganism, e.g., a prokaryote, or a non-unicellular microorganism, e.g., a eukaryote.

Useful unicellular microorganisms are bacterial cells such as gram positive bacteria including, but not limited to, a *Bacillus* cell, e.g., *Bacillus alkalophilus*, *Bacillus amyloliquefaciens*, *Bacillus brevis*, *Bacillus circulans*, *Bacillus clausii*, *Bacillus coagulans*, *Bacillus lautus*, *Bacillus lentus*, *Bacillus licheniformis*, *Bacillus megaterium*, *Bacillus stearothermophilus*, *Bacillus subtilis*, and *Bacillus thuringiensis*; or a *Streptomyces* cell, e.g., *Streptomyces lividans* and *Streptomyces murinus*, or gram negative bacteria such as *E. coli* and *Pseudomonas* sp. In a preferred aspect, the bacterial host cell is a *Bacillus lentus*, *Bacillus licheniformis*, *Bacillus stearothermophilus*, or *Bacillus subtilis* cell. In another preferred aspect, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278).

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, Ainsworth and Bisby's Dictionary of The Fungi, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series No. 9*, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell.

In a most preferred aspect, the yeast host cell is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis* or *Saccharomyces oviformis* cell. In another most preferred aspect, the yeast host cell is a *Kluyveromyces lactis* cell. In another most preferred aspect, the yeast host cell is a *Yarrowia lipolytica* cell.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium, Aspergillus, Aureobasidium, Bjerkandera, Ceriporiopsis, Coprinus, Coriolus, Cryptococcus, Filobasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

In a most preferred aspect, the filamentous fungal host cell is an *Aspergillus awamori, Aspergillus fumigatus, Aspergillus foetidus, Aspergillus japonicus, Aspergillus nidulans, Aspergillus niger* or *Aspergillus oryzae* cell. In another most preferred aspect, the filamentous fungal host cell is a *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides,* or *Fusarium venenatum* cell. In another most preferred aspect, the filamentous fungal host cell is a *Bjerkandera adusta, Ceriporiopsis aneirina, Ceriporiopsis aneirina, Ceriporiopsis caregiea, Ceriporiopsis gilvescens, Ceriporiopsis pannocinta, Ceriporiopsis rivulosa, Ceriporiopsis subrufa,* or *Ceriporiopsis subvermispora, Coprinus cinereus, Coriolus hirsutus, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The contact between the target biomolecule, the dual affinity polypeptide (DAP), and the solid support can be performed in several optional ways. In one embodiment all components could be brought into contact in one step, eg. by loading the target polypeptide and the fusion protein on the solid support without pre-incubation in solution. The dual affinity polypeptide can however, be contacted with the target before loading this complex on the solid support. In this embodiment the target biomolecule and the dual affinity polypeptide are contacted first, e.g. in solution, and subsequently the formed complex is contacted with the solid support. Depending on the nature of the solid support preferred embodiments of this principle could differ.

In one preferred embodiment the solid support is a solid phase matrix. This includes conventional solid phase matrixes. In the case of solid phase matrixes in the form of columns, the target and the dual affinity polypeptide can in one embodiment be contacted first in solution and subsequently contacted with the solid phase matrix by loading the complex onto the column.

It can be envisioned however, that e.g. the dual affinity polypeptide can be loaded on the solid support first and subsequently loading the target biomolecule In another embodiment the solid support is in the form of particles, in which case the order of contact is of less importance, and the contact of all the components could conveniently be performed in solution in one step or in several steps.

The catching ligand according to the invention is covalently attached to the solid support. As explained above the ligand according to the present invention is different from the ligand used in traditional affinity chromatography where the purpose of the ligand is to bind the target. In the present invention the ligand should bind to the DAP. Ligands are well known in the art and below are given examples that can be applied according to the invention. In the context of the present invention in one particular embodiment instead of a ligand attached to the solid phase the solid phase could alternatively comprise a binding affinity or binding site towards the DAP. An example could be cellulose as the solid phase and CBD (cellulose binding domain) as part of the DAP.

In one embodiment the ligand is chosen from but not limited to the group consisting of biotin, acarbose, steroids, haptens, epitope-peptides, dyes and enzyme inhibitors. In a particular embodiment the ligand is biotin. The ligand can be chemically attached to the solid support as described in the examples where the chemical attachment of acarbose and reactive red 6 is illustrated.

The coupling of affinity ligands to supports strongly influences the specificity, capacity and cost of traditional affinity chromatography columns.

The current state of the art in covalent coupling technology allows for chemo and regio selective coupling of the binding ligands to the support, often using spacers or linkers to anchor the ligand to the surface.

Great care is taken to avoid using functional groups that are close to a binding site or that play a role in the interaction between the ligand and target molecule.

If a suitable functional group does not exist on the ligand, further derivatizing of the ligand can be done to add an appropriate functional group. Numerous references describe appropriate chemistries, including "Bioconjugate Techniques", by Greg T. Hermanson, Academic Press, 2008 and "Chemistry of Protein Conjugation and Cross-linking", by Shan S. Wong, CRC Press, 1991.

It is commonly accepted that a high concentration of coupled ligand often has adverse effects on affinity chromatography, also the binding efficiency of the medium may be reduced due to steric hindrance between the active sites. This is particularly pronounced when large molecules such as antibodies, antigens and enzymes interact with small ligands.

In addition, the target substances may become more strongly bound to closely packed ligands making elution difficult and also the extent of nonspecific binding increases at very high ligand concentrations, thus reducing the selectivity of the affinity column.

Ligand-surface interface interaction is known to be important for the affinity ligand performance. The length of spacer arms between the ligand and the surface is critical. If it is too short, the arm is ineffective and the ligand fails to bind the target in the sample. If it is too long, proteins may bind non-specifically to the spacer arm and reduce the selectivity of the separation. Often 4-12 atom long hydrophilic arms are used.

MabSelect™ Media and HiTrap MabSelect™ (GE Healthcare) are examples of affinity columns using oriented coupling of recombinant Protein A to the matrix via an engineered C-terminal cysteine and a hydrophilic spacer arm.

The present invention suggests the use of soluble dual affinity polypeptide which can be characterized and used in any concentration appropriate for the specific target concentration. The technical challenge of coupling delicate target specific binding ligands to a solid support is substituted with more simple preparation of soluble molecules making it possible to utilize the entire arsenal of analytical methods.

There are numerous types of support material for affinity chromatography.

The size and uniformity of beads, the distribution of internal channels and the nature of the surfaces has all been optimized to produce numerous types of supports.

In general, smaller particle size and greater porosity, ensures increased dynamic binding capacity. On the other hand, resistance to mechanical collapses is reduced.

Both compressible and the incompressible support material needs to be robust enough to survive multiple cycles without change of flow rates which will influence the residence time.

The solid support are in the form of beads, gels or granulates. The quality of packing of the solid support material in columns for traditional affinity purification and the flow rates during operation greatly influence the performance.

Specialized equipment is used to successfully pack large columns above 5-10 cm in diameter. High performance columns are normally purchased pre-packed and in standard sizes. Consequently, the practical dimensions during scale up depend on available column systems for the purification of the particular target molecule.

The present invention suggests a general method using target DAP molecules and a generic column.

One of the most important factors in determining the cost and quality of the large scale purification is the chemical and mechanical stability of the adsorbent.

Traditional affinity columns with immobilized protein ligands are susceptible to further degradation due to for example oxidation or microbial growth.

Therefore, due to the cost of large affinity columns, great care has to be taken to control the storage condition between uses. Often the column is washed and stored with a special buffer solution containing anti microbial agents, alcohols or similar. These storage solutions must be washed away before use.

Some affinity ligands are also sensitive to proteases and the column lifetime will be reduced unless special cleaning and regeneration procedures are followed rigorously. The freedom to design efficient affinity purification procedures is therefore somewhat restricted.

A single use column system according to the invention or a column system using synthetic ligands will not have the above technical limitations.

In one embodiment of the invention the solid support is in the form of a solid phase matrix. The solid phase matrix may comprise, as the matrix backbone, any natural or synthetic and organic or inorganic material known per se to be applicable in solid phase separation of proteins and other biomolecules, e.g. natural or synthetic polysaccharides such as agar-agar and agaroses; celluloses, cellulose ethers such as hydroxypropyl cellulose, carboxymethyl celluose; starches; gums such as guar gum, and gum arabic, gum ghatti, gum tragacanth, locust bean gum, xanthan gum; pectins; mucins; dextrans; chitins; chitosans; alginates; carrageenans; heparins; gelatins; synthetic polymers such as polyamides such as polyacrylamides and polymethacrylamides; polyimides; polyesters; polyethers; polymeric vinyl compounds such as polyvinylalcohols and polystyrenes; polyalkenes; inorganic materials such as silicious materials such as silicon dioxide including amorphous silica and quartz; silicas; metal silicates, controlled pore glasses and ceramics; metal oxides and sulfides, or combinations of these natural or synthetic and organic or inorganic materials.

The matrix backbone is preferably selected from agar-agar, agaroses, celluloses, cellulose ethers such as hydroxypropyl cellulose, carboxymethyl cellulose, polyamides such as poly(meth)acrylamides, polyvinylalcohols, silicas, and controlled pore glasses.

Especially interesting solid phase materials as matrix backbones are e.g. agar or agarose beads such as Sepharose and Superose beads from GE Healthcare, USA, and Biogel A from Biorad, USA; dextran based beads such as Sephadex, GE Healthcare; cellulose based beads and membranes such as Perloza cellulose from Iontosorb, Czech Republic; composite beads such as Sephacryl and Superdex, GE Healthcare, USA; beads of synthetic organic polymers such as Fractogel from Tosoh Lifesciences LLC, USA; POROS media from Applied Biosystems, USA, Bio-Rex, Bio-Gel P and Macro Prep from Biorad, HEMA and Separon from TESSEK and Hyper D and Trisacryl media from Pall Corporation, USA, Enzacryl and Azlactone, 3M, USA; beads of siliceous materials such as controlled pore glass, PROSEP, from Millipore, USA, and Spherocil, Pall Corporation, USA; and coated silica composites in the form of beads or membranes such as ACTI-DISK, ACTI-MOD and CycloSep from Arbor Technologies, USA.

The ligand (e.g. biotin or similar specific molecules of low molecular weight (LMW)) is then covalently attached to this material. Several coupling chemistries of ligand molecules to the solid support can be selected from text books on the subject (Protein Purification, 1998, 2ed, eds. Janson, J-C., Rydén, L, Wiley & sons inc. New York). Based on the particular purification task the best candidate of ligand derivatives is coupled to the best choice of solid support, e.g. solid phase matrix or particles. Production process properties of the affinity solid matrix are analyzed through practical laboratory and pilot testing.

The ligands may be attached to the solid phase material by any type of covalent bond known per se to be applicable for this purpose, either by a direct chemical reaction between the ligand and the solid phase material or by a preceding activation of the solid phase material or of the ligand with a suitable reagent known per se making it possible to link the matrix backbone and the ligand. Examples of such suitable activating reagents are epichlorohydrin, epibromohydrin, allyl glycidylether; bis-epoxides such as butanedioldiglycidylether; halogen-substituted aliphatic compounds such as di-chloropropanol, divinyl sulfone; carbonyldiimidazole; aldehydes such as glutaric dialdehyde; quinones; cyanogen bromide; periodates such as sodium-meta-periodate; carbodiimides; chloro-triazines such as cyanuric chloride; sulfonyl chlorides such as tosyl chlorides and tresyl chlorides; N-hydroxy succinimides; 2-fluoro-1-methylpyridinium toluene-4-sulfonates; oxazolones; maleimides; pyridyl disulfides; and hydrazides. Among these, the activating reagents leaving a spacer group SP1 different from a single bond, e.g. epichlorohydrin, epibromohydrin, allyl-glycidylether; bis-epoxides;

halogen-substituted aliphatic compounds; divinyl sulfone; aldehydes; quinones; cyanogen bromide; chloro-triazines; oxazolones; maleimides; pyridyl disulfides; and hydrazides, are preferred.

In one embodiment the solid support is in the form of particles. Particles can be selected from the group comprising microspheres, latex particles or beads. The particles can be made from but not limited to the group consisting of e.g. polystyrene, silica, naphtaleen, polybutylmethacrylate.

The generic solid support can be produced at costs comparable to ion exchange matrices and the recombinant dual affinity protein can also be produced as a recombinant fusion protein by fermentation at low cost. Due to the lowered cost of the novel downstream procedure materials, the purification technology may be provided as disposables, which eliminate the need for expensive cleaning in place (CIP) and certain validations. Another consequence of the reduced cost is optional large column-volume applications, which saves manufacturing labour expenses, prevent repeated purification re-runs and limit time occupations of the downstream process plant.

The use of a generic solid support including the capturing ligand and the potentially improved binding efficiency and capacity due to complex formation in solution poses several advantages over the conventional affinity chromatography. These advantages are listed below.

No time consuming and expensive chemical conjugation reactions, purifications and QC procedures of protein ligands to prepare the affinity column material prior to affinity purification of the target molecule.

The generic matrix is more cost efficient to manufacture compared to the present commercial affinity matrices matrices (e.g. Protein A). Only one type of capturing column material is required for all affinity purifications using the dual affinity polypeptide principle. The low molecular weight ligand, e.g. biotin, dye molecules or similar specific low molecular weight (LMW) molecules are covalently attached by simple low cost conjugation procedures to make the generic solid phase matrix.

The preferred fermentation of a dual affinity polypeptide fusion protein is "simple", based on known technology and provide the conjugation needed between binding domains in DAP The manufacturing cost of DAP molecules is comparable or cheaper than recombinant Protein A molecules.

The DAP fusion protein and the generic matrix required for purification purposes costs a fraction of the ready-to-use Protein A affinity matrix for similar purposes The DAP transport and immobilize the target molecules to the generic matrix during the purification process. The is no need for an expensive and time consuming immobilization of a dedicated ligand to make an specific purification matrix as known in conventional affinity chromatography.

The low cost of the components in the presented invention facilitate a disposable affinity purification process featuring
- elimination of CIP procedures
- elimination of validation procedures
- save time on regulatory issues
- exclude repetitions of down stream process cycles
- limit operational failures
- lower labor expenses during processing
- shorter manufacturing run time
- limit risk of contamination
- easy to use
- lower capacity cost investments due to flexible plant designs
- better down stream process economy Substitution of conventional multi-cycle protein separation procedures to a single step using the disposable affinity purification technology.

In a particular modified form of the invention it could be envisioned that the DAP molecule could bind covalently to the solid support. This would still allow the possibility of having the DAP and the target reacting in solution. Such a covalent bond could in one embodiment be formed by cleavage of a para-substituted benzyl guanine resulting in a thioether bond.

One embodiment of this modified form of the invention therefore relates to a process for purification of a target biomolecule, comprising the steps: (a) contacting (i) a target polypeptide, (ii) a dual affinity polypeptide, and (iii) a solid support comprising a catching ligand, wherein the dual affinity polypeptide has an equilibrium dissociation constant, $K_{D,t}$ towards the target biomolecule in the range from $10^{-2}$ to $10^{-13}$ M, more particularly from $10^{-4}$ to $10^{-13}$ M at standard conditions, and wherein binding of the dual affinity polypeptide to the catching ligand on the solid support is provided by cleavage of a para-substituted benzyl guanine resulting in a thioether bond; and (b) recovering the target biomolecule by elution.

The basic principle of the affinity purification technology, for purifying a target molecule (polyclonal antibody) is illustrated below.

EXAMPLES

Example 1

Preparation of Dual Affinity Linker by Chemical Conjugation

Based on published values for binding affinities, dual linker binding functionalities were selected that fit both to the binding to the ligand matrix ($K_{D,s}$~$10^{-6}$ to $10^{-16}$M) and to the target biomolecules (products, $K_{D,t}$~$10^{-2}$ to $10^{-13}$ M). To investigate the influence of the $K_{D,s}$, some components with $K_{D,s}$-values outside the above interval were also tested.

In order to prepare a conjugate made from Protein A and a biotin binding protein e.g. Avidin, Streptavidin or Neutravidin the two proteins were chemically activated separately as a first step and joined together by cross linking in a second step afterwards.

Protein A do not have accessible sulphydryl (—SH) on the surface, so these were introduced be reaction with SATA (N-succinimidyl S-acetylthioacetate) to primary amine (—NH2) functional groups on Protein A. SATA (or SATP) is a reagent for introducing protected sulfhydryls into proteins, peptides and other molecules. They are the N-hydroxysuccinimide (NHS) esters of S-acetylthioacetic and propionic acid. A stable, covalent amide bond was formed from the reaction of the NHS ester with primary amines. The amine was reacted with the NHS ester by nucleophilic attack, with N-hydroxysuccinimide being released as a by-product. Deprotection (deacylation) to generate a sulfhydryl for use in cross-linking and other applications was accomplished using hydroxylamine.HCl.

The maleimide groups were introduced to the Avidin using Sulfo-SMCC. Sulfo-SMCC is a heterobifunctional cross-linker that contains a N-hydroxysuccinimide (NHS) ester and a maleimide group. NHS esters react with primary amines at pH 7-9 to form covalent amide bonds. SMCC and Sulfo- SMCC are often used to prepare protein-protein conjugates in a two-step reaction scheme. First, the amine-containing protein was reacted with a several-fold molar excess of the cross linker, followed by removal of excess (nonreacted) reagent by desalting or dialysis; finally, the sulfhydryl-containing molecule is added to react with the maleimide groups already attached to the first protein.

The conjugates prepared by cross linking were obtained by reacting maleimides with sulphydryl groups at pH 6.5-7.5 to form stable thioether bonds.

An alternative to the procedure above is to use commercially available Malimide activated Neutravidin instead of the activated Avidin. Maleimide Activated NeutrAvidin™ Protein is for directly preparing NeutrAvidin™ Protein (NAP) conjugates with proteins, peptides, and other molecules that contain a free sulfhydryl (—SH) group.

Preparation of Dual Affinity Polypeptide (DAP) by Chemical Cross-Linking

Procedure for chemically cross-linking Protein A, and either Avidin or Neutravidin into a conjugate with the required properties of a DAP linker.
Materials
SATA (N-Succinimidyl S-Acetylthioacetate), (Pierce, no. 26102)
D-Salt™ Excellulose™ Desalting Column, 5 ml (Pierce No. 20449)
Hydroxylamine.HCl (Pierce, No. 26103), DMSO (Dimethylsulfoxide, Pierce, No. 20688), Sulfo-SMCC: (sulfosuccinimidyl 4-(N-maleimidomethyl)cyclohexan-1-carboxylate) (Pierce, 22322), Protein A (GE Health Care, 17-0872-50), Avidin (Kem-En-Tec, 4020H), Maleimide activated neutravidin (Pierce, no. 31007), PD-10 Sephadex G-25M (GE; 17-0851-01), HiPrep 26/60 Sephacryl S-100 HR (MW range 1.000-100.000) (GE, 17-1194-01)
Anti-IgG Affibody (Affibody, 10.0623.01.0050)
Dithiothreitol ([3483-12-3], Sigma-Aldrich D0632).
Buffers:
PBS Reaction Buffer:
200-500 ml of PBS: 0.1 M phosphate, 0.15 M NaCl, pH 7.2
Deacetylation Solution:
0.5 M Hydroxylamine, 25 mM EDTA in PBS, pH 7.2
PBS-EDTA Solution:
200-500 ml of PBS: 0.1 M phosphate, 0.15 M NaCl, 5 mM EDTA, pH 7.2.
Phosphate-buffered saline (PBS, pH 7.2; or other amine- and sulfhydrylfree buffer at pH 6.5-7.5 adding EDTA to 1-5 mM helps to chelate divalent metals, thereby reducing disulfide formation in the sulfhydryl-containing protein.
Procedure for Sulfhydryl Modification of Protein A
A. Reaction of Protein A with SATA (or SATP)
Immediately before reaction, 6.4 mg of SATA was dissolved in 0.5 ml of DMSO (resulting in ~55 mM solution).
1.0 ml of Protein A solution (2.6 mg/mL) was then combined with 10 µl of the SATA solution. The contents were mixed and incubated at room temperature for 30 minutes.
The level of sulfhydryl incorporation may be altered by using different molar ratios of SATA to protein. The default reaction uses 60 nmol Protein A and 550 nmol SATA, a 9:1 molar ratio of SATA to protein. The amount of SATA in the reaction may be increased or decreased by adding more or less than 10 µl of the SATA solution per ml of Protein Solution.

B. Desalt to Purify Acylated Protein a from Excess Reagent and by-Products

A desalting column was equilibrated with two column volumes of Reaction Buffer. Use at least a 5 ml desalting column for each 1 ml of reaction volume to be processed.

1.01 ml reaction mixture was applied to the column. Collection of 1 ml fractions was started immediately. After the reaction mixture had completely entered the column bed and the first fraction was collected, at least 10 mL Reaction Buffer was added to the column and collection continued as separate 1 ml fractions as they emerged from the column.

Fraction(s) that contain Protein A were identified as those having peak absorbance at 280 nm. With a 5 ml desalting column, fractions 2 and 3 contained most of the protein, while excess SATA came out in the following fractions. The fractions that contain the modified Protein A were pooled.

The modified Protein A may be stored indefinitely for later deacetylation and generation of sulfhydryl groups (Section C).
C. Deacetylate SATA-Modified Protein A to Generate Sulfhydryl Groups 1.0 ml of SATA-modified (acetylated) Protein A was combined with 100 µl of the Deacetylation Solution. The contents were mixed and incubated 2 hours at room temperature.

A desalting column was used to purify the sulfhydryl-modified protein from the Hydroxylamine in the Deacetylation Solution.

Desalting was done into Reaction Buffer containing 10 mM EDTA to minimize disulfide bond formation using the same procedure as in Section B. Fractions that contained the modified Protein A were pooled. The protein concentration should be ~1.3 mg/ml. In order to minimize disulfide formation Section D was performed immediately.

Before or after desalting, the protein may be assayed for sulfhydryl content using Ellman's Reagent (Pierce, no 23460 (kit for sulfhydryl group detection)).
D. Conjugation of SATA modified Protein A to maleimide activated Avidin or Neutravidin.

This method uses approximately equimolar amounts of activated Protein A to Avidin or Neutravidin.

Example 1a

Procedure for Maleimide Modification of Avidin and Preparation of the DAP molecule [Protein A—Avidin]

Generally, a 10- to 50-fold molar excess of cross-linker over the amount of amine-containing protein results in sufficient maleimide activation to enable several sulfhydryl-containing proteins to be conjugated to each amine-containing protein.

More dilute protein solutions require greater fold molar excess of reagent to achieve the same activation level. Empirical testing is necessary to determine optimal activation levels and final conjugation ratios for the intended application.
Protocol For best results, ensure that Protein A-SH is prepared as described above and ready to combine with maleimide activated Avidin in step 5.

32 mg Avidin was prepared in 5 mL PBS Buffer, and 4.36 mg sulfo-SMCC was prepared in 1 mL PBS/EDTA buffer. Then 500 µL of the activation solution was transferred to the Avidin solution. The mixture was incubated 30 minutes at room temperature. Excess cross-linker was remove using a desalting column equilibrated with PBS-EDTA Buffer.

Protein A-SH and desalted maleimid activated Avidin were combined and mixed in a molar ratio corresponding to approximately 1:1. The reaction mixture was incubated at room temperature overnight.

Generally, there is no harm in allowing the reaction to proceed for several hours or overnight, although usually the reaction will be complete in about 30 min. To stop the conjugation reaction before completion, add buffer containing reduced cysteine at a concentration several times greater than the sulfhydryls of Protein A-SH.

Example 1b

Preparation of the DAP Molecule [Protein A—Neutravidin]

For best results, ensure that Protein A-SH is prepared as described above and ready to combine with maleimide activated Avidin.

Maleimide activated Neutravidin (Pierce, no 31007) is commercially available for directly preparing NeutrAvidin™ Protein (NAP) conjugates with proteins, peptides, and other molecules that contain a free sulfhydryl (—SH) group. NeutrAvidin™ Protein is a modified avidin derivative with several key features that provide a biotin-binding protein with exceptionally low nonspecific binding properties. NeutrAvidin™ Protein does not contain carbohydrates, rendering lectin-binding activity to undetectable levels. Additionally, the isoelectric point of NAP is 6.3±0.3, which is much lower than native Avidin and not as acidic as streptavidin.

Protocol 1.0 mL of ultra pure water was added to suspend 5 mg lyophilized Neutravidin.

Protein A-SH and maleimid activated Neutravidin were combined and mixed in a molar ratio corresponding to 1:1. The reaction mixture was incubated at room temperature overnight.

Generally, there is no harm in allowing the reaction to proceed for several hours or overnight, although usually the reaction will be complete in the specified time. To stop the conjugation reaction before completion, add buffer containing reduced cysteine at a concentration several times greater than the sulfhydryls of Protein A-SH.

Example 1c

Preparation of the DAP Molecule [Affibody (IgG)—Avidin]

Protocol

Avidin (10 mg) was activated with sulfo-SMCC as described in Example 1a.

Anti-IgG Affibody disulfide dimers were reduced to monomers:

Anti-IgG Affibody (5 mg) is dissolved in PBS-buffer (5 mL), and 3.8 mL of this solution is transferred to a vial containing 12.3 mg dithiothreitol (DTT) giving a final DTT concentration of 20 mM solution. This mixture is turned at RT for 2 h.

Upon this, excess DTT is removed by splitting the reaction mixture in two portions, passing each portion through a PD-10 column (bedvolume 8 mL). The columns had been equilibrated with 25 mL PBS buffer before use. The monomeric Anti-IgG Affibody is eluted from the columns in 2×9-10 fractions, each containing 1 mL.

By measuring $A_{280}$ of the fractions the protein was located in 2 fractions from each column. These fractions were pooled and mixed with the desalted maleimid activated avidin solution (20 mL) in a molar ratio corresponding to approximately 1:1 (avidin calculated as monomer; MW=17.000), and the coupling was allowed to proceed overnight at room temperature with gently turning of the coupling mixture.

The following day, 1500 µL of the conjugation mixture was concentrated in an Amicon Ultra (cut off 3 kDa) to a total volume of 400 µL, which was used for analysis by SDS PAGE. This showed that all avidin had reacted, and that there was still some unreacted anti-IgG Affibody present.

The conjugation mixture was freezed until purified by SEC.

The above protocol can be used for the preparation of all derivatives of Affibody-Avidin dual affinity polypeptides.

Example 1d

Preparation of the DAP Molecule [Affibody (Insulin)—Avidin]

Avidin (9 mg) was activated with sulfo-SMCC as described in Example 1a.

Anti-Insulin Affibody ($His_6$-Z000810-Cys; PB00014) disulfide dimers were reduced to monomers as described in Example 1c.

The pooled fractions from the PD-10 columns were mixed with the desalted maleimid activated avidin solution (16.1 mL) in a molar ratio corresponding to approximately 1:1, and the coupling was allowed to proceed overnight at room temperature with gently turning of the coupling mixture.

The following day, the conjugation mixture was analyzed by SDS PAGE. This showed that all avidin had reacted, and that there was still some unreacted anti-Insulin Affibody present.

The conjugation mixture was freezed until purified by SEC.

Example 1e

Preparation of the DAP Molecule [Affibody (Insulin)—Avidin]

Avidin (9 mg) was activated with sulfo-SMCC as described in Example 1a. Anti-Insulin Affibody (Insulin, $His_6$-Z01139-Cys; PB00022) disulfide dimers were reduced to monomers as described in Example 3c.

The pooled fractions from the PD-10 columns were mixed with the desalted maleimid activated avidin solution (16.1 mL) in a molar ratio corresponding to approximately 1:1, and the coupling was allowed to proceed overnight at room temperature with gently turning of the coupling mixture.

The following day, the conjugation mixture was analyzed by SDS PAGE. This showed that all avidin had reacted, and that there was still some unreacted anti-Insulin Affibody present. The conjugation mixture was freezed until purified by SEC.

Example 2

Recombinant Dual Affinity Constructs for Expression in *Aspergillus oryzae*

Strains

*Aspergillus oryzae* BECh2 is described in WO 00/39322, example 1, which is further referring to JaL228 described in WO 98/12300, example 1.

JaL1168 is described in example 2g.
JaL1171 is described in example 2g.
JaL1174 is described in example 2g.
JaL1176 is described in example 2g.
JaL1181 is described in example 2g.
JaL1210 is described in example 2g.

MT173 is a derivative of MC1000 (Casadaban & Cohen J. Mol. Biol. 138 (1980) 179-207) which are ara+ and leuB6.

Genes

AMG: indicate the *Aspergillus niger* glucoamylase gene (Boel et al. EMBO Journal 3 (1984) 1581-1585)

Z: indicated the Z domain from *Staphylococcus aureus* protein A (Nilsson et al. Protein Engineering 1 (1987) 107-113).

Pre-CBD$_{(C315)}$: indicate the *Meripilus giganteus* endoglucanase II (DSM971) signal (pre)+cellulose binding domain (CBD)+linker region.

CBD(egv): indicated the *Humicola insulens* endoglucanase V (DSM1800) linker region+cellulose binding domain.

VhhRR6(2): indicated the variable region from a Llama single chain antibody reacting against the hapten azo-dye Reactive Red (RR6) (Frenken et al. J. Biotechnology 78 (2000) 11-21.

Plasmids p775 is described in EP 238023.

pA2C315 is deposited at DSM under the accession no. DSM971. The plasmid contains a cDNA clone from *Meripilus giganteus* encoding an endoglucanase II gene.

pCAMG91 is described in Boel et al. EMBO Journal 3 (1984), 1581-1585.

pJaL790 is described in WO2005070962, example 1.
pJaL1153 is described in example 2c.
pJaL1154 is described in example 2a.
pJaL1158 is described in example 2d.
pJaL1159 is described in example 2a.
pJaL1164 is described in example 2c.
pJaL1165 is described in example 2d.
pJaL1168 is described in example 2e.
pJaL1169 is described in example 2b.
pJaL1170 is described in example 2f.
pJaL1171 is described in example 2b.
pMT2786 is described in WO2006050737 example 2.
pSX320 is described in EP 0 531 372.

Primer and DNA Sequences

Synthetic DNA 1 (SEQ ID NO 1)
Synthetic DNA 2 (SEQ ID NO 4)
Adaptor sequence 1 (SEQ ID NO 5)
Adaptor sequence 2 (SEQ ID NO 6)
primer 8683 (SEQ ID NO 10)
primer CBD:Z-NA (SEQ ID NO 11)
primer Z-NA (SEQ ID NO 12)
primer Z-CA (SEQ ID NO 13)
primer Z-CA:CBD (SEQ ID NO 14)
primer 8654 (SEQ ID NO 15)
Primer CBD:Z-NB (SEQ ID NO 19)
Primer Z-NB (SEQ ID NO 20)
Primer Z-CB (SEQ ID NO 21)
Primer Z-NB:CBD (SEQ ID NO 22)

Methods

General methods of PCR, cloning, ligation nucleotides etc. are well-known to a person skilled in the art and may for example be found in in "Molecular cloning: A laboratory manual", Sambrook et al. (1989), Cold Spring Harbor lab., Cold Spring Harbor, N.Y.; Ausubel, F. M. et al. (eds.); "Current protocols in Molecular Biology", John Wiley and Sons, (1995); Harwood, C. R., and Cutting, S. M. (eds.); "DNA Cloning: A Practical Approach, Volumes I and II", D. N. Glover ed. (1985); "Oligonucleotide Synthesis", M. J. Gait ed. (1984); "Nucleic Acid Hybridization", B. D. Hames & S. J. Higgins eds (1985); "A Practical Guide To Molecular Cloning", B. Perbal, (1984).

PCR Amplification

All PCR amplifications were performed in a volume of 100 microL containing 2.5 units Taq po-lymerase, 100 ng of pSO2, 250 nM of each dNTP, and 10 pmol of each of the two primers described above in a reaction buffer of 50 mM KCl, 10 mM Tris-HCl pH 8.0, 1.5 mM MgCl2. Amplification was carried out in a Perkin-Elmer Cetus DNA Termal 480, and consisted of one cycle of 3 minutes at 94° C., followed by 25 cycles of 1 minute at 94° C., 30 seconds at 55° C., and 1 minute at 72° C.

*Aspergillus* Transformation

*Aspergillus* transformation was done as described by Christensen et al.; Biotechnology 1988 6 1419-1422. In short, *A. oryzae* mycelia were grown in a rich nutrient broth. The mycelia were separated from the broth by filtration. The enzyme preparation Novozyme® (Novo Nordisk) was added to the mycelia in osmotically stabilizing buffer such as 1.2 M MgSO$_4$ buffered to pH 5.0 with sodium phosphate. The suspension was incubated for 60 minutes at 37 degrees C. with agitation. The protoplast was filtered through mira-cloth to remove mycelial debris. The protoplast was harvested and washed twice with STC (1.2 M sorbitol, 10 mM CaCl$_2$, 10 mM Tris-HCl pH 7.5). The protoplasts were finally re-suspended in 200-1000 microl STC.

For transformation, 5 microg DNA was added to 100 microl protoplast suspension and then 200 microl PEG solution (60% PEG 4000, 10 mM CaCl$_2$, 10 mM Tris-HCl pH 7.5) was added and the mixture is incubated for 20 minutes at room temperature. The protoplast were harvested and washed twice with 1.2 M sorbitol. The protoplast was finally re-suspended 200 microl 1.2 M sorbitol. Transformants containing an intact niaD gene were selected for its ability to used nitrate as the sole source for nitrogen on minimal plates (Cove D. J. 1966. Biochem. Biophys. Acta. 113:51-56) containing 1.0 M sucrose as carbon source, 10 mM Sodium nitrate as nitrogen source. After 4-5 days of growth at 37 degrees C., stable transformants appeared as vigorously growing and sporulating colonies. Transformants were purified twice through conidiospores.

Media and Reagents

YPM medium (2 g/l yeast extract, 2 g/l peptone, and 2% maltose)

Growth of *Aspergillus* Transformants

Shake flask containing 10 ml YPM medium was inoculated with spores from the respective transformants and incubated at 30 degrees C., at 200 rpm for 4 days.

SDS-Gage

SDS gel used was Criterion™ XT precast gels, 10% Bis-Tris, from BIO-RAD and was run and stained with Coomassie blue as recommend by the manufactory.

Example 2a

Construction of *Aspergillus* Expression Cassette pJaL1159 (Pre-CBD$_{(C315)}$-KR::VhhRR6(R2)::Z::Z)

Plasmid pJaL1154 contains a synthetic DNA SEQ ID NO 1 in pUC19 encoding a fusion protein composed of: signal+cellulose binding domain+linker from C315, the amino acids KR, the variable region of a llama single chain antibody raised against the reactive dye RR6, and a repeat of the Z domain from protein A (pre-CBD$_{(C315)}$-KR::VhhRR6(R2)::Z::Z).

Expression vector pJaL1159 was constructed for transcription of the fusion protein pre-CBD$_{(C315)}$-KR::VhhRR6(R2)::Z::Z (SEQ ID NO 2). The plasmid pJaL1154 harboring the fusion protein was digested with BamHI-XhoI. The 966 bp fragment was gel-purified and ligated into the *Aspergillus* expression cassette pMT2786 digested with BamH I-XhoI (a 6936 bp fragment). The ligation mixture was transformed into *E. coli* MT173 using the *Saccharomyces cerevisiae* Leu2 gene as selective marker to create the expression plasmid pJaL1159. The amplified plasmid was recovered using a QIAprep® Spin Miniprep kit (QIAGEN, Chatsworth, Calif.) according to the manufacturer's instructions.

Plasmid pMT2786 comprise an expression cassette based on the *Aspergillus niger* neutral amylase II promoter fused to the *Aspergillus nidulans* triose phosphate isomerase non translated leader sequence (Na2/tpi promoter) and the *Aspergillus niger* amyloglycosidase terminator (AMG terminator), the selective marker amdS from *Aspergillus nidulans* enabling growth on acetamide as nitrogen source and having the *Saccharomyces cerevisiae* Leu2 gene for selection in *E. coli*.

Example 2b

Construction of *Aspergillus* Expression Cassette pJaL1171 Pre-CBD$_{(C315)}$-KR::VhhRR6(R2)::Z For construction of the fusion protein pre-CBD$_{(C315)}$-KR::VhhRR6(R2)::Z (SEQ ID NO 3) plasmid pJaL1154 was digested with BglII and the 3472 bp fragment was gel-purified and ligated with itself resulting in pJaL1169. The 795 bp BamHI-XhoI fragment from pJaL1169 was purified and ligated into the *Aspergillus* expression cassette pMT2780 digested with BamH I and XhoI (a 6936 bp fragment). The ligation mixture was transformed into *E. coli* MT173 using the *Saccharomyces cerevisiae* Leu2 gene as selective marker to create the expression plasmid pJaL1171. The amplified plasmid was recovered using a QIAprep® Spin Miniprep kit (QIAGEN, Chatsworth, Calif.) according to the manufacturer's instructions.

Example 2c

Construction of *Aspergillus* Expression Cassette pJaL1164 AMG$_{(1-526aa)}$::Z::Z Plasmid pJaL1153 contains a synthetic DNA SEQ ID NO 4 in pUC19 encoding a fusion protein composed of: *Aspergillus niger* AMG DNA encoding amino acids 488-526 and a repeat of the Z domain from protein A (AMG$_{(488-526aa)}$::Z::Z).

Plasmid pToC100 contains the *Aspergillus niger* AMG (Boel et al. EMBO Journal 3 (1984), 1581-1585) regulated by the TAKA promoter from p775 and at the same time a BamHI site was introduce upfront of the AMG start codon. pToC100 was constructed by ligating the following fragments together: 4306 bp BamHI-NcoI fragment from p775, an adapter SEQ ID NO: 5 and SEQ ID NO.: 6, 860 bp BssHII-Pst1 from pCAMG91 and 1410 bp PstI-NcoI fragment from pCAMG91.

Expression vector pJaL1164 was constructed for transcription of the fusion protein AMG$_{(1-526aa)}$::Z::Z (SEQ ID NO 7). A 1723 bp BamHI-DraIII fragment and a 458 bp DraIII-XhoI fragment was gel-purified from plasmid pToC100 and pJaL1153, respectively, and ligated into the *Aspergillus* expression cassette pMT2786 digested with BamH I-XhoI (a 6936 bp fragment). The ligation mixture was transformed into *E. coli* MT173 using the *Saccharomyces cerevisiae* Leu2 gene as selective marker to create the expression plasmid pJaL1164. The amplified plasmid was recovered using a QIAprep® Spin Miniprep kit (QIAGEN, Chatsworth, Calif.) according to the manufacturer's instructions.

Example 2d

Construction of *Aspergillus* Expression Cassette pJaL1165 AMG$_{(1-526aa)}$::Z

For construction of an expression plasmid encoding for the fusion protein AMG$_{(1-526aa)}$::Z (SEQ ID NO 8) plasmid pJaL1153 was digested with BglII and the 2969 bp fragment was gel-purified and ligated with itself resulting in pJaL1158. A 1723 bp BamHI-DraIII fragment from pToC100 and a 287 bp fragment from pJaL1158 was purified and ligated into the *Aspergillus* expression cassette pMT2786 digested with BamH I and XhoI (a 6936 bp fragment). The ligation mixture was transformed into *E. coli* MT173 using the *Saccharomyces cerevisiae* Leu2 gene as selective marker to create the expression plasmid pJaL1165. The amplified plasmid was recovered using a QIAprep® Spin Miniprep kit (QIAGEN, Chatsworth, Calif.) according to the manufacturer's instructions.

Example 2e

Construction of *Aspergillus* Expression Cassette pJaL1168 Pre-CBD$_{(C315)}$::Z::Z::CBD$_{(Egv)}$ Construction of the expression plasmid pJaL1168 encoding for the fusion protein pre-CBD$_{(C315)}$::Z::Z::CBD$_{(EGV)}$ (SEQ ID NO 9) was done by amplification by PCR: 1) of the pre-CBD$_{(C315)}$ region using pA2C315 as template and the primer pair 8683/CBD:Z-NA (SEQ ID NO 10 and 11), 2) of the Z::Z region using pJaL1153 as template and the primer pair Z-NA/Z-CA (SEQ ID NO 12 and 13) and 3) of the CBD$_{(EGV)}$ region using pSX320 as template and the primer pair Z-CA:CBD/8654 (SEQ ID NO 14 and 15), resulting in 3 DNA fragments of 337 bp, 382 bp and 344 bp, respectively. The 3 fragments were mixed and used as template for amplification by PCR with primer pair 8653/8654 of a 983 bp fragment. The PCR fragment was digested with BamHI-HindIII and the 798 bp fragment was purified and clone ligated into the *Aspergillus* expression cassette pJaL790 digested with BamH I-HindIII (a 7386 bp fragment). The ligation mixture was transformed into *E. coli* DB6507 using the *Saccharomyces cerevisiae* Ura3 gene as selective marker to create the expression plasmid pJaL1168. The amplified plasmid was recovered using a QIAprep® Spin Miniprep kit (QIAGEN, Chatsworth, Calif.) according to the manufacturer's instructions.

Plasmid pJaL790 comprised an expression cassette based on the *Aspergillus niger* neutral amylase II promoter fused to the *Aspergillus nidulans* triose phosphate isomerase non translated leader sequence (Na2/tpi promoter) and the *Aspergillus niger* amyloglycosidase terminator (AMG terminator), the selective marker amdS from *Aspergillus oryzae* enabling growth on acetamide as nitrogen source.

Example 2f

Construction of *Aspergillus* Expression Cassette pJaL1170 Pre-CBD$_{(C315)}$-KR::Z::Z::CBD$_{(C315)}$::CBD$_{(EGV)}$ Plasmid pJaL802 is an *Aspergillus* expression plasmid builds on pJaL790 which contains a DNA (SEQ ID NO 16) encoding for the fusion protein pre-CBD$_{(C315)}$::CBD$_{(EGV)}$ (SEQ ID NO 17).

Construction of the expression plasmid pJaL1170 encoding for the fusion protein pre-CBD$_{(C315)}$-KR::Z::Z::CBD$_{(C315)}$::CBD$_{(EGV)}$ (SEQ ID NO 18) was done by amplification by PCR: 1) of the pre-CBD$_{(C315)}$-KR region using pA2C315 as template and the primer pair 8683/CBD:Z-NB (SEQ ID NO 10 and 19), 2) of the Z::Z region using pJaL1153 as template and the primer pair Z-NB/Z-CB (SEQ ID NO 20 and 21) and 3) of the CBD$_{(C315)}$-CBD$_{(EGV)}$ region using pJaL802 as template and the primer pair Z-CB:CBD/8654 (SEQ ID NO 22 and 15), resulting in 3 DNA fragments of 343 bp, 382 bp and 443 bp, respectively. The 3 fragments were mixed and used as template for amplification by PCR with primer pair 8653/8654 of a 1088 bp fragment. The PCR fragment was digested with BamHI-HindIII and the 894 bp fragment was purified and clone ligated into the *Aspergillus* expression cassette pJaL790 digested with BamH I-HindIII (a 7386 bp fragment). The ligation mixture was transformed into *E. coli* DB6507 using the *Saccharomyces cerevisiae* Ura3 gene as selective marker to create the expression plasmid pJaL1170. The amplified plasmid was recovered using a QIAprep® Spin Miniprep kit (QIAGEN, Chatsworth, Calif.) according to the manufacturer's instructions.

Example 2g

Expression of DAP in *Aspergillus oryzae* Strains

The *Aspergillus oryzae* strains BECh2 was transformed with the expression plasmid pJaL1159, pJaL1164, pJaL1165, pJaL1168, pJaL1170 and pJaL1171 as described under methods.

A shake flask containing 10 ml YPM medium (2 g/l yeast extract, 2 g/l peptone, and 2% maltose) was inoculated with spores from the generated transformants and the host BECh2 and incubated at 30° C., with shaking (200 rpm) for 4 days. Supernatants (10 µl) were analysed on SDS-page. A transformant producing the desired protein from each plasmid pJaL1159, pJaL1164, pJaL1165, pJaL1168, pJaL1170 and pJaL1171 was named JaL1210, JaL1168, JaL1171, JaL1174, JaL1176 and JaL1181, respectively. Products of the expected size from each transformant were confirmed by SDS-page. The amino acids sequence of each construct produced in JaL1210 (VhhRR6(R2)::Z::Z), JaL1168 (AMG$_{(1-526aa)}$::Z::Z), JaL1171 (AMG$_{(1-526aa)}$::Z), JaL1174 (CBD$_{(C315)}$::Z::Z::CBD$_{(egv)}$), JaL1176 (Z::Z::CBD$_{(C315)}$::CBD$_{(egv)}$) and JaL1181 (VhhRR6(R2)::Z) are shown in SEQ ID NO 23, SEQ ID NO 24, SEQ ID NO 25, SEQ ID NO 26, SEQ ID NO 27 and SEQ ID NO 28, respectively.

Example 3

Recombinant Dual Affinity Constructs for Expression in *Bacillus licheniformis*

Media

LB agar, TY buillon medium and BPX shake flask medium have all been described in Patent Publication WO 94/14968.

CAL 18-2 media (1l): Yeast extract (#0127-17-9 Difco Laboratories, MI, USA) 40 g; Magnesium Sulfate (#5886 Merck, Darmstadt, Germany) 1.3 g; Glucidex 12 (Roquette Feres, France) 50 g; Sodium Di-hydrogenphosphate (#6346 Merck, Darmstadt, Germany) 20 g; EDF-Tracemetals (recipe see below) 6.7 ml; Na$_2$MoO$_4$-Tracemetals (recipe see below) 6.7 ml; Pluronic PE6100 (BASF, Germany) 0.1 ml; Ionexchanged water adjust to 1000 ml. All is mixed, volume is adjusted, pH is measured and adjusted to pH 6.0 using NaOH. The media is sterilised by aotoclaving at 121° C. for 20 min.

EDF-Tracemetals (1l): Mangan (II) sulphate (#5963 Merck, Darmstadt, Germany) 4.48 g; Iron (III) chloride (#3943 Merck, Darmstadt, Germany) 3.33 g; Copper (II) sulphate (#2790 Merck, Darmstadt, Germany) 0.625 g; Zinksulphate (#8883 Merck, Darmstadt, Germany) 7.12 g; Ionexchanged water adjust to 1000 ml. All is mixed, volume is adjusted. Solution is filter-sterilized and kept at 4° C. Na$_2$MoO$_4$-Tracemetals (1l): SodiumMolybdat (#6521 Merck, Darmstadt, Germany) 2.0 g; Ionexchanged water adjust to 1000 ml. All is mixed, volume is adjusted. Solution is filtersterilized and kept at 4° C.

Strains and Donor Organisms

*Bacillus subtilis* PL1801. This strain is the *B. subtilis* DN1885 with disrupted apr and npr genes (Diderichsen, B., Wedsted, U., Hedegaard, L., Jensen, B. R., Sjoholm, C. (1990) Cloning of aldB, which encodes alpha-acetolactate decarboxylase, an exoenzyme from i *Bacillus brevis*. J. Bacteriol., 172, 4315-4321).

*Bacillus subtilis* PP289-5. This strain is a donor strain for conjugation of plasmids to *Bacillus licheniformis* described in U.S. Pat. No. 5,843,720

*Bacillus licheniformis* MDT223 described in patent WO2005/123915

Genes

Z: indicate the Z domain from *Staphylococcus aureus* protein A (Nilsson et al. Protein Engineering 1 (1987) 107-113). The Z gene is a synthetic gene assembled by primers (SEQ ID NO 29)

Streptavidin gene: indicate the gene encoding Streptavidin from *Streptomyces avidinii* as described by Argarana (Argarana et. Al. (1986) Nucleic Acids Res. 14, 1871-1882). The gene encoding streptavidin is a synthetic gene (SEQ ID NO 30)

A synthetic gene can be constructed by PCR assembly of overlapping oligonucleotides in various methods described eg. by Stemmer et al, Gene 164, pp-49-53, 1995; Dillon and Rossen, BioTechniques 9, 298-300, 1990; Prodromou and Pearl, Protein Engineering 5, 827-829, 1992; Chn et al., Journal of American Chemical Society 11, 8799-8800, 1994 and others. Such genes may also simply be purchased through one of many commercial companies.

Plasmids pSJ6208 is an *E. coli* pUC derivative described in SEQ ID NO 31.

pSJ6321 is a pE194 derivative with an erythromycin marker gene. The plasmid also holds cryIIIA stabilizer sequence, DNA encoding the signal peptide of amyL fused to a protease followed by a downstream sequence of amyL (SEQ ID NO 32).

pMOL2743 is described in this example (SEQ ID NO 33)
pMOL2744 is described in this example (SEQ ID NO 34)
pMOL2746b is described in this example (SEQ ID NO 35)
Construction of Integration Vector Z::Z::Streptavidin for *B. Licheniformis* Expression The synthetic gene (SEQ ID NO 29) encoding the Z::Z domaine was amplified by the primers SEQ ID NO 36 and SEQ ID NO 37:

```
SEQ ID NO 36:
TCATTCTGCAGCAGCGGCGGATAACAAATTTAACAAAGAACAG-

CAGAACGCGTTTTATGAAA

SEQ ID NO 37:
AACTAAGCGGCCGCTAGCGACTACACTTTAGGAGCTT-

GCGCGTCATTAAGCT
```

The PCR fragment was digested with PstI-EagI and the 368 bp fragment was purified and ligated into the *E. coli* pUC derivative plasmid pSJ6208 (SEQ ID NO 31) digested with PstI-EagI giving a 3389 bp fragment. The ligation mixture was transformed into *E. coli* SJ2 (Diderichsen, B., Wedsted, U., Hedegaard, L., Jensen, B. R., Sjoholm, C. (1990). Cloning of aldB, which encodes acetolactate decarboxylase, an exoenzyme from *Bacillus brevis*). The plasmid holding the sub cloned Z::Z gene pMOL2743 (SEQ ID NO 33), was recovered using a QIAprep® Spin Miniprep kit (QIAGEN, Chatsworth, Calif.) according to the manufacturer's instructions.

The synthetic gene (SEQ ID NO 30) encoding streptavidin was digested with HindIII giving a fragment of 620 bp. The plasmid pMOL2743 was restricted with HindIII and treated with alcaline phosphatase to avoid relegation. The two fragments were ligated and transformed to the *E. coli* SJ2. The colonies were screened for presence of the streptavidin gene and clones were picked where the streptavidin gene is inserted in the right orientation giving rise to the plasmid pMOL2744 (SEQ ID NO 34). In this plasmid the genes encoding the Z::Z domaine and Streptavidin if translationally fused.

The hybrid gene encoding Z::Z::Streptavidin was transferred to an integration vector designed to allow integration of the amylase expression cassette into the chromosome of a *B. licheniformis* strain, that already contains an artificial tandem promoter integrated at the amyL locus, as described in example 6 of WO2005/123915. This was achieved by a ligation of three fragments. The first fragment is a PstI-BgIII restriction digest of pMOL2744 giving rise to a 931 bp fragment. The second fragment is a BgIII-BamHI restriction digest of the plasmid pSJ6321 (SEQ ID NO 32) isolating a 4288 bp fragment. The third fragment is a BamHI-PstI digest of pSJ 6321 isolating a 1234 bp fragment. The three fragments were ligated and introduced by transformation into PL1801 giving rise to an integration vector pMOL2746b (SEQ ID NO 35).

This pMOL2746b plasmid is then re-transformed by either competence, electroporation or conjugation into a protease deficient *Bacillus licheniformis* and inserted by double homologoes integration at the amyL locus using an already inserted cryIIIA sequence and the amyl downstream sequence. The resulting *Bacillus licheniformis* strain has the artificial tandem promoter and cryIIIA sequence driving the Z::Z::Strepavidin expression from the amyL locus. The *Bacillus licheniformis* host is preferred to be protease deficient to allow expression of the Z::Z::Streptavidin hybrid protein. The following proteases can be deleted by standard techniques using double homologous recombination: mpr, aprE, nprE, vpr, bpr, epr, wprA and ispA.

The protease deficient *Bacillus licheniformis* host with the expression cassette encoding the Z::Z::Strepatavidin hybrid DAP protein is fermented in 100 ml shake flasks with CAL18-2 medium described above at 30° C., 300 rpm for 2 days. Samples are taken out day one and day two to evaluate the DAP expression on an SDS gel. The data show a protein band at the right size of 30 KDa.

The PCR fragment is digested with the restriction enzymes Rsa I and Hind III and the resulting 489 bp fragment is cloned into the 5327 pStrExp1 digested with the restriction enzymes Nru I and Hind III by DNA ligation and cloning into *B. subtilis* PL1801.

The DNA sequence of the open reading frame encoding the fusion protein is shown in SEQ ID NO: 38, and the protein sequence in SEQ ID NO: 39.

Example 4

Expression of the DAP Construct in *Bacillus subtilis*

Transformants of *B. Subtilis* PL1801 is grown in shake flasks as described in patent WO 2000/075344 and the fusion protein is recovered from the supernatant. The antibody binding and biotin binding properties of the fusion protein is confirmed as shown elsewhere herein.

Example 5

Purification of DAP

5a. Chemically Synthesized DAP Purified by Size Exclusion Chromatography

The conjugation mixtures from example 1 were loaded on a size exclusion column in order to purify the DAP-molecules by removing reactants. The size exclusion chromatography was performed on a prepacked Superdex 200 16/60 column. 1 mL of DAP reaction solution was loaded on the column. The pump flow was 1.00 mL/min, the eluent was 150 mM NaCl, 50 mM Hepes pH 7.0 and fractions of 1 mL were collected. Fractions were pooled based on absorbance measurements at 280 nm in order to remove reactants.

The collected and pooled fractions were concentrated 10× using Amicon Ultracentrifuge tubes with a NWCO of 3000.

5b. Recombinant DAP by IgG-Sepharose Affinity Chromatography

Recombinant DAP molecules were purified from the fermentation broth by sterile filtration and subsequent column purification by IgG affinity chromatography.

The IgG-sepharose column was prepared by following the procedure supplied by the vendor:

15 g CNBr-activated sepharose 4B from GE Healthcare was washed for 15 min with 3 L 1 mM HCl. The washed medium was added to 25 mL 20 mg/mL IgG solution from DAKO A/SA (X0903) and 50 mL 0.75 M NaCl, 0.15 M NaHCO$_3$ pH 8.3. The mixture was gently rotated for 95 min. at room temperature. Excess IgG was washed away with 75 mL 0.1 M NaHCO$_3$ pH 8.3 containing 0.5 M NaCl before the medium was incubated in 0.1 M Tris/HCl pH 8.0 for 2 hours. The medium was stored in 20% ethanol until use.

Generic Procedure for Purification of Recombinant DAP

The recombinant DAP molecules from examples 2 and 3 were purified by a generic affinity chromatographic method that takes advantage of the IgG binding domain shared by all the recombinant DAP constructs. The DAP molecules were purified from the sterile filtered fermentation broth.

The chromatography was performed on a XK26/20 column packed with approx. 30 mL IgG-sepharose. The fermentation broths were sterile filtered and between 65 mL and 80 mL was loaded depending on the volume of the filtered fermentation broth. The pump flow was 1.50 mL/min during sample load and 2 mL/min during wash and elution. Buffer A was 0.1 M NaH$_2$PO$_4$ pH 7.2, 0.15 M NaCl and buffer B: 0.1 M Citric acid pH 3.5. The column was washed with 15 column volumes buffer A following the sample load. The bound material was eluted with 5 column volumes buffer B before the column was regenerated with 10 column volumes buffer A. Fractions of 10 mL were collected. Eluate having an increase of absorbance at 280 nm was pooled and the pH was adjusted to 7.2 using 1 M Tris. The concentration of the DAP protein was calculated from the absorption at 280 nm and the theoretical absorption coefficients calculated from the primary sequence using GPMAW 8.0 (Trends in Biochemical Science, Vol 26, No. 11, November 2001, pp 687-689, "GPMAW—a software tool for analyzing proteins and peptides"; see also http://www.gpmaw.com/). The Mw of the purified proteins were determined by SDS-PAGE. The samples were stored at −18° C. before further analysis.

Example 6

Characterization of DAP Molecules with Regard to Binding Strength Measured on the Biacore Instrument The commercialised surface plasmon resonance (SPR) technology for real time monitoring biomolecular binding event is used to measure the binding affinities for the prepared DAP candidates. The general principle of this technology is that a SPR sensor chip measures changes in refractive index, and the changes in refractive index correlate to changes in mass in the aqueous layer close to the sensor surface. When target molecules in solution bind to ligands, immobilised on the sensor surface, the mass increases, and when they dissociate from the ligands the mass decreases. This principle facilitates a continuous, real time monitoring of the association and dissociation of interacting molecules. The graphical presentation of the relationship provides quantitative information in real time on the binding specificity, active concentration of molecule in a sample, reaction kinetics and affinity.

In order to evaluate the binding affinities for both of the binding affinities present in the DAP either IgG or the capturing ligand had to be immobilized onto the sensor chip. For IgG rabbit anti-Mannanase was used and for the ligand the chip was coated with streptavidin and the ligand was then immobilized via biotin linked to the appropriate ligand.

In order to measure the binding to RR6 and acarbose the following compounds were prepared; biotin-linked acarbose and biotin-linked RR6.

Preparation of Biotin Linked Acarbose

Biotin (5 mg, 26 µmol) was dissolved in DMF (250 µL) in a 2 mL eppendorf tube, and to this EDC.HCl (5 mg, 26 µmol) was added. The mixture was stirred at RT for 30 min. Acarbose (16.1 mg, 25 µmol) was dissolved in DMF (250 µL) in a 2 mL eppendorf tube, and to this the activated biotin solution was added dropwise, while the reaction mixture was gently stirred. When all activated biotin solution was added, 100 µL DMF was used to wash the reaction container, and these 100 µL were also added to the acarbose solution. The reaction mixture was left stirring for 2 h at RT. Upon this, the DMF was removed by freeze-drying overnight at −5° C. The crude product was stored at −18° C., until used in the Biacore experiments.

Preparation of Biotin Linked Reactive Red 6

Biotin (5 mg, 26 µmol) was dissolved in DMF (250 µL) in a 2 mL eppendorf tube, and to this EDC.HCl (5 mg, 26 µmol) was added. The mixture was stirred at RT for 30 min. 1,4-Diaminobutane (25.1 µL, 25 µmol) was dissolved in DMF (250 µL) in a 2 mL eppendorf tube, and to this the activated biotin solution was added dropwise, while the reaction mixture was gently stirred. When all activated biotin solution was added, 100 µL DMF was used to wash the reaction container, and these 100 µL were also added to the diaminobutane solution. The reaction mixture was left stirring for 2 h at RT.

Reactive Red 6 (24.4 mg, 25 µmol) was dissolved in DMF (250 µL) in a 2 mL eppendorf tube, and to this the biotin-amide solution was added dropwise, while the reaction mixture was gently stirred. When all biotin-amide solution was added, 100 µl DMF was used to wash the reaction container and these 100 µL were also added to the RR6 solution.

The reaction mixture was left stirring overnight at RT. The DMF was removed by freeze-drying overnight at −5° C. The crude product was stored at −18° C., until used in the Biacore experiments.

Biacore Evaluation:

The DAP candidates were analysed for binding to the capturing ligand sensor chip and the target biomolecule sensor chip respectively. A Biacore 3000 instrument was used.

To study the interactions between the IgG-binding end of the DAP molecule and IgG on the one hand, and the interaction between the ligand-binding end and the ligand (biotin, acarbose, reactive red) on the other hand, IgG and ligand were immobilized onto the sensor surface of a sensor chip as described below.

Immobilisation occurred by direct covalent coupling to the surface (using the Amine Coupling Kit, BiaCore, GE Health Care) or via a capturing molecule as prescribed by the manufacturer (BiaCore, GE Health Care). The amount of coupled target was quantified and expressed in Refractive Units (RU).

Interactions were monitored by injecting samples (20 µl/min) over the prepared sensor surface of the chip. Unless stated otherwise, the binding was assessed in 10 mM sodium acetatbuffer pH 5.0 at room temperature.

Experiment 1:

Chip: CM5

Immobilized target: rabbit anti-Mannanase (10 µg/ml) in 10 mM acetatbuffer pH 5.0.

Target RU: 1250 RU

Actual RU:

FC1: 1349

FC2: 1492

FC3: 1338

FC4: 1331

Samples:

FC1: Protein A, 1 µg/ml injected

FC2: Protein A—Avidin, 0.5 µg/ml injected

FC3: Protein A—Avidin, 0.5 µg/ml injected

FC4: Affibody (IgG)—Avidin, 0.6 µg/ml injected

Results:

|  | ka | kd | KA | KD | Final RU |
|---|---|---|---|---|---|
| Protein A |  |  |  |  |  |
| $Chi_2 = 0.06$ | 4.35e5 | 3.4e−6 | 1.28e11 | 7.81e−12 | 140 |
| Protein A-Avidin |  |  |  |  |  |
| $Chi_2 = 0.737$ | 6.99e5 | 1.75e−7 | 3.99e12 | 2.5e−13 | 130 |
| $Chi_2 = 1.82$ | 1.21e6 | 5.03e−5 | 2.41e10 | 4.15e−11 | 130 |
| Affibody(IgG)-Avidin |  |  |  |  |  |
| $Chi_2 = 0.505$ | 9.56e4 | 6.41e−8 | 1.49e12 | 6.7e−13 | 105 |

Experiment 2:
Chip: CM5
Immobilized target: rabbit anti-Mannanase (10 µg/ml) in 10 mM acetatbuffer pH 5.0.
Target RU: 1250 RU
Actual RU:
FC2: 1697
FC3: 1665
Samples:
FC2: CBD-Z-Z-CBD, 10 µg/ml injected
FC3: CBD-Z-Z-CBD, 10 µg/ml injected
Results:

| CBD-Z-Z-CBD | ka | kd | KA | KD | Final RU |
|---|---|---|---|---|---|
| $Chi_2 = 2.3$ | 1.46e5 | 2e−4 | 7.3e8 | 1.37e−9 | 200 |
| $Chi_2 = 3.78$ | 1.23e5 | 2.08e−4 | 5.93e8 | 1.69e−9 | 200 |

Experiment 3:
Chip: CM5
Immobilized target: rabbit anti-Mannanase (10 µg/ml) in 10 mM acetatbuffer pH 5.0.
Target RU: 1250 RU
Actual RU:
FC3: 1485
FC4: 1760
Samples:
FC3: AMG-Z, 10 µg/ml injected
FC4: AMG-ZZ, 10 µg/ml injected
Results:

|  | ka | kd | KA | KD | Final RU |
|---|---|---|---|---|---|
| AMG-Z |  |  |  |  |  |
| $Chi_2 = 6.76$ | 2.69e6 | 1.08e−2 | 2.49e8 | 4.02e−9 | 5 |
| AMG-ZZ |  |  |  |  |  |
| $Chi_2 = 2.97$ | 3.46e5 | 4.1e−4 | 8.42e8 | 1.19e−9 | 150 |

Experiment 4:
Chip: CM5
Immobilized target: rabbit anti-Mannanase (1 µg/ml) in 10 mM acetatbuffer pH 5.0.
Target RU: 625 RU
Actual RU:
FC1: 683
FC2: 731
FC3: 881
FC4: 716

Samples:
FC1: Protein A, 1 µg/ml injected
FC2: ZZ-CBD-CBD, 0.1 µg/ml injected
FC3: VhhRR6(R2)-Z, 1 µg/ml injected
FC4: CBD-Z-Z-CBD, 1 µg/ml injected
Results:

|  | ka | kd | KA | KD | Final RU |
|---|---|---|---|---|---|
| Protein A |  |  |  |  |  |
| $Chi_2 = 1.22$ | 4.27e5 | 1.26e−4 | 3.38e9 | 2.95e−10 | 55 |
| ZZ-CBD-CBD |  |  |  |  |  |
| $Chi_2 = 0.116$ | 4.6e6 | 3.3e−4 | 1.39e10 | 7.18e−11 | 70 |
| VhhRR6(R2)-Z |  |  |  |  |  |
| $Chi_2 = 2.35$ | 3.2e5 | 1e−3 | 3.2e8 | 3.13e−9 | 70 |
| CBD-Z-Z-CBD |  |  |  |  |  |
| $Chi_2 = 1.96$ | 2.65e5 | 2.97e−4 | 8.94e8 | 1.12e−9 | 50 |

Experiment 5:
Chip: SA
Immobilization: None. The Chip is pre-coated with Streptavidin.
Immobilisation of the ligand through Biotin-Streptavidin binding
FC1: Biotin—Acarbose, 10 µg/ml
FC2: Biotin—Acarbose, 10 µg/ml
FC3: Biotin—Reactive Red 6, 10 µg/ml
Binding of the DAP via the ligand-binding end of the molecule to the ligand.
FC1: AMG-Z-Z, 10 µg/ml
FC2: AMG-Z, 10 µg/ml
FC3: VhhRR6(R2)-Z, 10 µg/ml
Results:

|  | ka | kd | KA | KD | Final RU |
|---|---|---|---|---|---|
| AMG-Z-Z |  |  |  |  |  |
| $Chi_2 = 1.38$ | 6.29e3 | 2.69e−3 | 2.34e6 | 4.27e−7 | 15 |
| AMG-Z |  |  |  |  |  |
| $Chi_2 = 2.9$ | 1.02e4 | 1.8e−3 | 5.64e6 | 1.77e−7 | 20 |
| VhhRR6(R2)-Z |  |  |  |  |  |
| $Chi_2 = 3.24$ | 1.72e4 | 3.99e−3 | 4.31e6 | 2.32e−7 | 15 |

Experiment 6:
Chip: SA
Immobilization: None. The Chip is pre-coated with Streptavidin.
Immobilisation of the ligand through Biotin-Streptavidin binding
FC4: Biotin-Reactive Red 6, 10 µg/ml
Binding of the DAP via the ligand-binding end of the molecule to the ligand in the presence of IgG binding to the Z-domain of the DAP molecule.
FC4: VhhRR6(R2)-Z+IgG 9.3 µg/ml
Result:

| VhhRR6(R2)-Z + IgG | ka | kd | KA | KD | Final RU |
|---|---|---|---|---|---|
| $Chi_2 = 5.3$ |  | 225 | 6.18e−3 | 3.65e4 | 2.74e−5 | 5 |

TABLE 1

| DAP | IgG binding | | | Ligand | Ligand binding | | |
|---|---|---|---|---|---|---|---|
| | $k_a$ (1/Ms) | $k_d$ (1/s) | $K_D$ (M) | | $k_a$ (1/Ms) | $k_d$ (1/s) | $K_D$ (M) |
| Avidin-Protein A | $1 \times 10^6$ | $3 \times 10^{-5}$ | $2 \times 10^{-11}$ | Biotin[a] | — | — | — |
| Avidin-Affibody (IgG) | $1 \times 10^3$ | $6 \times 10^{-8}$ | $7 \times 10^{-13}$ | Biotin | — | — | — |
| AMG-ZZ | $4 \times 10^5$ | $4 \times 10^{-4}$ | $1 \times 10^{-9}$ | Acarbose | $6 \times 10^3$ | $3 \times 10^{-3}$ | $4 \times 10^{-7}$ |
| AMG-Z | $3 \times 10^6$ | $1 \times 10^{-2}$ | $4 \times 10^{-9}$ | Acarbose | $1 \times 10^4$ | $2 \times 10^{-3}$ | $2 \times 10^{-7}$ |
| CBD-ZZ-CBD | $2 \times 10^5$ | $2 \times 10^{-4}$ | $1 \times 10^{-9}$ | Cellulose | | | |
| ZZ-CBD-CBD | $5 \times 10^6$ | $3 \times 10^{-4}$ | $7 \times 10^{-11}$ | Cellulose | | | |
| VhhRR6(R2)-Z | $3 \times 10^5$ | $1 \times 10^{-3}$ | $3 \times 10^{-9}$ | RR6[b] | $2 \times 10^4$ | $4 \times 10^{-3}$ | $2 \times 10^{-7}$ |
| Protein A control | $5 \times 10^5$ | $7 \times 10^{-5}$ | $2 \times 10^{-10}$ | — | — | — | — |

[a] Binding between biotin and avidin/streptavidin is not measured, since it is known to be very tight, and no dissociation can therefore be measured.
[b] If VhhRR6(R2)-Z is mixed with IgG before loading to the Biacore, the $K_D$ is $10^{-5}$M, however, the binding is broken completely as soon as the injection is stopped.

Example 7

Purification of Antibodies Using Dual Affinity Polypeptide Purification Technology Below is a short description of a generally applicable procedure for immunoglobulin purification:

1. A disposable generic solid phase with a low molecular weight capturing ligand molecule.
2. The dual affinity polypeptide DAP (e.g. Avidin-Protein A) reacts with the IgG (target biomolecule) in the solution. The DAP molecules are immobilized on the solid phase (e.g. biotin-agarose) in a complex together with the target protein (IgG).
3. The column is washed to eliminate interfering non-product components.
4. The immunoglobulin is eluted from the column using an appropriate buffer at low pH.
5. The antibody containing fractions are collected and pH is neutralized.
6. The generic matrix containing immobilized dual affinity polypeptide may be discarded.

Materials and Methods:

All buffer ingredients were pro-analysis. Rabbit serum proteins and Rabbit IgG fraction, code X0903 were from DAKO A/S, Denmark. Biotin Agarose was from Sigma-Aldrich; B6885-5ML.

The purification experiments were performed using a chromatography system comprising a fraction collector (Frac-100), a recorder (Rec-1), an optical unit and a control UV-1, all from GE Healthcare. For all experiments we used a Bio-RAd Econo-column ID 1.0 cm with a flow adaptor. The equilibration and dilution buffer was 0.1 M phosphate, 0.15 M NaCl, pH=7.2 (PBS). The elution buffer was 0.1 M citrate, pH=3.5, or alternatively 0.1 M glycine, pH=2.8.

The data processing was based on Abs 280 nm measurement using a Pharmacia Gene Quant II and the extinction coefficient for Rabbit IgG (1 g/L) of 1.35.

IgG Purification Analysis

All experiments were performed at room temperature.

Example 7a

Recovery of Rabbit IgG with free DAP [Protein A—Neutravidin]

The sorbent (Biotin Agarose, 5 mL) was allowed to settle in the column for 10 min. The column was packed at a flow of 1.46 mL/min. The column was equilibrated with 7.5 column volumes (CV) PBS. DAP (Protein A-Neutravidin) solution (4.5 mL from example 1b) was mixed with 100 μL Rabbit IgG stock solution (20 g/L) and incubated for 5 minutes on a magnetic stirrer. The reaction solution was loaded on the column and washed with 7.5 CV of PBS to remove excess of target protein. The IgG was recovered by elution with 3 CV of 0.1 M glycine buffer (pH 2.8). 5 mL fractions were collected and analyzed for IgG content by Abs 280. See Table 2 for results.

Example 7b

Recovery of Rabbit IgG with Immobilized DAP [Protein A—Neutravidin]

The gel material from example 7a with immobilized DAP [Protein A—Neutravidin] was regenerated with 7.5 CV PBS before analyzing the conventional affinity purification capabilities.

We loaded 2 mg IgG in 4.6 mL PBS solution on the column. After sample loading, the column was washed with 7.5 CV of PBS to remove excess of protein. Then the column was eluted with 3 CV of 0.1 M Glycine buffer (pH 2.8) to recover the IgG. 5 mL fractions were collected and analyzed for IgG content by Abs 280 and SDS-PAGE. See Table 2 for results.

TABLE 2

| | Flow through | Recovered |
|---|---|---|
| Example 1b - Free DAP | 74% | 26% |
| Example 1b - Immobilized DAP | 86% | 14% |

As seen in Table 2, we obtained approximately twice the binding capability (26% versus 14%) when DAP and IgG are reacted in solution prior to loading on the column compared to the conventional affinity chromatography applying immobilized DAP.

Example 7c

Purification of Rabbit IgG from serum with free DAP [Protein A—Neutravidin]

We studied purification of IgG from rabbit serum to show the specificity of the DAP purification technology.

Approximately 1 mL of sorbent (Biotin Agarose) was allowed to settle in the column for 10 min. The column was packed at a flow of 1.46 mL/min. The column was equilibrated with 7.5 column volumes (CV) PBS. A 4.5 mL DAP (Protein A—Neutravidin) solution (from example 1b) were mixed with 115 µL rabbit serum and incubated for 5 minutes on a magnetic stirrer. The reaction solution was loaded on the column following a wash with 7.5 CV of PBS to remove excess of target protein. The IgG was recovered by elution with 3 CV of glycine buffer. 2.5 mL fractions were collected and analyzed for IgG content by Abs 280 and SDS-PAGE. See Table 3 for results.

Example 7d

Purification of Rabbit IgG from serum with immobilized DAP [Protein A—Neutravidin]

The gel from example 1c with immobilized DAP [Protein A—Neutravidin] was regenerated with 7.5 CV PBS before analyzing the conventional affinity purification capabilities We loaded rabbit serum (115 µL rabbit serum in 4.5 mL PBS) solution on the column. After sample loading, the column was washed with 7.5 CV of PBS to remove excess of protein. Then the column was eluted with 3 CV of 0.1 M Glycine buffer (pH 2.8) to recover the target IgG. The gel was regenerated with 7.5 CV PBS before the next affinity purification cycle. 2.5 mL fractions were collected and analyzed for IgG content by Abs 280 and SDS-PAGE. See Table 3 for results.

TABLE 3

| | Recovered IgG (mg) from serum |
|---|---|
| Example 1b - Free DAP | 0.31 |
| Example 1b - Immobilised DAP | 0.18 |

As seen in Table 3, we obtained approximately twice the binding capability (0.31 mg versus 0.18 mg IgG), when DAP was reacted with rabbit serum in solution prior to contacting the biotin-agarose column compared to the conventional affinity chromatography applying immobilized DAP.

SDS-PAGE showed that only IgG molecules were obtained from serum, showing that the DAP purification technology is specific.

We repeated the analysis using the other DAP conjugate (Protein A-Avidin) and performed similar tests as above but included an analysis of the leakage of DAP from the column by repeated binding analysis to the immobilized DAP.

Example 7e

Recovery of Rabbit IgG with free DAP [Protein A—Avidin]

The sorbent (Biotin Agarose, 1 mL) was allowed to settle in the column for 10 min. The column was packed at a flow of 1.46 mL/min. The column was equilibrated with 7.5 column volumes (CV) PBS. 2 mL of DAP (Protein A—Avidin) solution (from example 3a) was mixed with 160 µL Rabbit IgG stock solution (20 g/L) and incubated for 5 minutes on a magnetic stirrer. The reaction solution (~2 CV) was loaded on the column following a wash with 7.5 CV of PBS to remove excess of target protein. The IgG was recovered by elution with 3 CV of 0.1 M Citrate, pH=3.5. 2.5 mL fractions were collected and analyzed for IgG content by Abs 280. The results are shown in Table 4.

TABLE 4

Free DAP versus reuses of immobilised DAP technology
(Protein A - Avidin conjugate)
Rabbit IgG recovery

| | Free DAP | 1. reuse of immobilsed DAP | 2. reuse of immobilsed DAP | 3. reuse of immobilsed DAP | 4. reuse of immobilsed DAP |
|---|---|---|---|---|---|
| IgG Recovered (mg) | 1.20 | 0.30 | 0.40 | 0.40 | 0.30 |

Example 7f

Recovery of Rabbit IgG with immobilized DAP [Protein A—Avidin]

The gel from example 7e with immobilized DAP [Protein A—Avidin] was regenerated with 7.5 CV PBS before analyzing the conventional affinity purification capabilities The rabbit IgG stock solution (20 g/L) was diluted to a concentration of 1.5 mg/mL with PBS. In each runs 3.2 mg of IgG was loaded (in 2.16 mL) on the column. After sample loading (~2 CV), the column was washed with 7.5 CV of PBS to remove excess of protein. Then the column was eluted with 3 CV of elution buffer (0.1 M Citrate, pH=3.5) to recover the target IgG. The gel was regenerated with 7.5 CV PBS before the next affinity purification cycle. 2.5 mL fractions were collected and analyzed for IgG content by Abs 280.

When DAP is reacted with 3.2 mg of IgG in solution prior to contacting with the Biotin-Agarose we recovered 1.2 mg of IgG compared to the 0.35 mg IgG which was recovered on average in four repeated cycles with immobilized DAP.

The above results thus illustrate the advantageous effect of using a DAP according to the invention compared to conventional chromatography.

Example 8

Recovery of IgG Using Dual Affinity Chromatography

The purified DAP molecules from examples 5a and 5b were evaluated in a generic purification assay.

The experiments were conducted at room temperature using an Äkta explorer system. 0.6 mL solid phase material was packed at a flow rate of 1.2 mL/min in an empty glass column (6.6×100 mm) equipped with an adjustable flow adaptor (Omnifit). The column was packed in 0.1 M sodium phosphate, 0.15 M NaCl, pH=7.2 (PBS) and allowed to equilibrate with 10 column volumes PBS followed by 3 column volumes 0.1 M citrate, pH=3.5 and finally 10 column volumes PBS before use.

ZZ-CBD-CDB and CBD-ZZ-CBD were analyzed using a column packed with cellulose. 1.2 g Avicel (Merck product no. 1.02331) was suspended in 8 ml PBS in a test tube and the suspension was allowed to settle for 30 min. Subsequently the fine particles were decanted before the column was packed.

AMG-Z and AMG-ZZ were evaluated using a column packed with Acarbose-agarose. Approx. 0.6 mL of the Acarbose-agarose from Example 9 was transferred to the column and allowed to settle for 10 min before the column was packed.

VhhRR6(R2)-Z was analysed using a column packed with RR6-agarose. Approx. 0.6 mL of the Reactive Red-agarose from Example 9 was transferred to the column and allowed to settle for 10 min before the column was packed.

Avidin-Protein A, Avidin-Affibody and ZZ-Streptavidin were evaluated using a column packed with Biotin-agarose. Approx. 0.6 mL of Biotin-agarose (Sigma B6885) was transferred to the column and allowed to settle for 10 min before the column was packed.

The packed column was operated at a flow rate of 0.6 mL/min. Buffer A was 0.1 M sodium phosphate pH 7.2, 0.15 M NaCl and buffer B was 0.1 M Citric acid pH 3.5. The column was initially washed with 10 column volumes buffer A before 0.6 mL sample was injected. The column was washed with 7.5 column volumes buffer A and the bound target protein was eluted with 5 column volumes buffer B. The column was finally regenerated with 10 column volumes buffer A. Detection was at 280 nm. The data were evaluated by determining the height of the peak observed during elution.

Purified DAP (8 nmole) was mixed with IgG (code X0903, DAKO A/S, 8 nmole) and water was added ad 660 µL. The reaction mixture was incubated on a magnetic stirrer for 10 minutes before it was injected onto the column. The solution of target protein was prepared as a 2 mg/mL IgG solution in water. The following sequence of injections was carried out in all experiments: Water; target protein (7.1 nmole); target protein and DAP reaction mixture; and finally 10 times subsequent injections of target protein (7.1 nmole).

The column employed for evaluating the Protein A—Avidin DAP molecule was subsequently used for assessing the effect of changing the load of target protein by varying the injection volume. Four injections were made: (0.6; 0.45; 0.3; 0.15) mL of the same IgG solution (12 µM). The results showed that the height of the peak observed during elution was almost constant whereas the height of peak observed in the flow through decreased markedly as the column load was lowered (Table 5). These results are in accordance with the nature of affinity chromatography and demonstrate that the applied approach of evaluating the data by using the height of the peak observed during elution is valid.

TABLE 5

Peak heights determined from injections of different volumes of IgG

| Injection volume mL | Peak height of flow through mAU | Peak height eluate mAU |
|---|---|---|
| 0.6 | 154 | 126 |
| 0.45 | 116 | 124 |
| 0.3 | 61 | 120 |
| 0.15 | 14 | 109 |

The non-specific binding of target protein to the column was evaluated by injecting water and subsequently the target protein before the DAP molecule was introduced to the column material. The peak heights observed from injections of water and IgG were comparable in all the experiments performed. This demonstrates that the peak observed during elution is unaffected of potential non-specific binding of target protein to the column. Thus the peak observed during elution is a measure of the recovered amount of target protein from the non-covalently immobilized DAP.

The ability of the DAP molecules to recover the target protein was analyzed by comparing the chromatograms obtained from injection of water, target protein and the target protein/DAP reaction mixture. The results are shown in Table 6. Only two DAP molecules were unable to recover the target protein. 1) VhhRR6(R2)-Z did not recover IgG, which may be explained by results from the Biacore analysis showing that the binding between DAP and ligand is broken completely as soon as the injection is stopped (Table 1 footnote). This indicates that the DAP molecule is quickly released from the solid phase and thus not suitable for affinity chromatography. 2) The ZZ-streptavidin DAP did not recover IgG which is likely explained by a blocking of the biotin binding sites due to the reaction with endogenous biotin present in the fermentation broth. Thus this ZZ-streptavidin preparation is likely not to bind to the solid phase.

TABLE 6

Ability of DAP molecules to recover the target protein

| DAP | Column materiale | Binding and elution of target protein |
|---|---|---|
| AMG-ZZ | Acarbose-agarose | + |
| AMG-Z | Acarbose-agarose | + |
| ZZ-CBD-CBD | Cellulose | + |
| CBD-ZZ-CBD | Cellulose | + |
| VhhRR6(R2)-Z | Reactive red-agarose | − |
| ZZ-streptavidin | Biotin-agarose | − |
| Affibody(IgG)-avidin | Biotin-agarose | + |
| ProteinA-avidin | Biotin-agarose | + |

The leakage of DAP from the column was assessed by 10 consecutive injections of the target protein following the initial injection of the DAP/target protein reaction mixture. The heights of the peaks observed during elution were determined and the relative responses were calculated relative to the first injection of IgG. The relative responses were plotted as a function of the injection number and the relative decrease in peak height was calculated by linear regression. The results from the different DAP—ligand combinations are shown in Table 7 together with the dissociation constants.

TABLE 7

Dissociation constants and relative leakage

| DAP | $K_{D,t}$ M | $K_{D,s}$ M | $K_{D,t}/K_{D,s}$ | Rel decrease %/inj | $r^2$ |
|---|---|---|---|---|---|
| AMG-ZZ | $1 \times 10^{-9}$ | $4 \times 10^{-7}$ | $3 \times 10^{-3}$ | −1.1 | 0.8 |
| AMG-Z | $4 \times 10^{-9}$ | $2 \times 10^{-7}$ | $2 \times 10^{-2}$ | −1.7 | 1.0 |
| ZZ-CBD-CBD[a] | $7 \times 10^{-11}$ | $10^{-6}$ | $7 \times 10^{-5}$ | −1.7 | 1.0 |
| CBD-ZZ-CBD[a] | $1 \times 10^{-9}$ | $10^{-6}$ | $1 \times 10^{-3}$ | −1.7 | 0.9 |
| Affibody(IgG)-avidin[b] | $7 \times 10^{-13}$ | $10^{-15}$* | $7 \times 10^{2}$ | −0.2 | 0.3[c] |
| Protein A-avidin[b] | $2 \times 10^{-11}$ | $10^{-15}$* | $2 \times 10^{4}$ | −0.7 | 0.9 |

[a]The dissociation constant ($K_D$) of CBDs binding to cellulose is generally considered to be ≈$10^{-6}$ M (Linder et al, Biotechnology and Bioengineering, Vol. 60, No. 5, Dec. 5, 1998).
[b]The dissociation constant ($K_D$) of avidin binding to biotin is well known to be $10^{-15}$ M (Green, N. (1963). Biochem J, 89, 585-591).
[c]The correlation coefficient reflects that the calculated leakage is mainly determined by a single point. The relative leakage is −0.05% with $r^2 = 0.0$ if this point is removed.

The results in Table 7 show purification schemes of the same target molecule (IgG) using various compositions of DAP molecules. It is concluded that the most efficient DAP molecules in affinity chromatography are those with tighter binding to the ligand on the matrix, i.e. those having a relative $K_{D,t}/K_{D,s} > 10^0 = 1$.

Specifically, the strong binding towards the column provided by the avidin-biotin bond prevents leakage of the bound DAP molecules.

Example 9

Preparation of Functionalized Resins

Materials
Resin: Mini-Leak-Low (loading 2-5 mM, Kem-En-Tec).
Ligands: 1,4-Diaminobutane ([110-60-1], Sigma-Aldrich, D13208), Reactive Red 6 (Cherry red #14, Grateful Dyes inc.), Acarbose ([56180-94-0] Sigma-Aldrich, A8980).
Coupling buffer: 0.5M $K_2HPO_4$—pH 8.5
Washing buffer: 0.5M $K_2HPO_4$—pH 7.0
Blocking buffer 0.1M Ethanolamine in Milli-Q water Preparation of an RR6-Agarose Resin Resin (10 ml, suspended) was washed 2× with destilled water and the water removed by filtration. 1,4-Diaminobutane (2.0 mL) was dissolved in coupling buffer (20 mL) and the resin was added slowly with gentle shaking. The resin was left shaking overnight at RT, whereupon it was washed with coupling buffer and sucked dry.

Reactive Red 6 (15.9 g) was dissolved in coupling buffer (50 mL) and to this solution, the amino-functionalized resin was added slowly with shaking. Again the resin was left shaking overnight at RT. After washing with water and washing buffer, the resin was transferred to blocking buffer (20 mL) and shaken for 2 h. Finally the resin was washed in water until the filtrate was colorless, and the red resin was suspended in 30% ethanol in Milli-Q water.

Preparation of an Acarbose-Agarose Resin

Resin (10 ml, suspended) was washed 2× with destilled water and the water removed by filtration. Acarbose (500 mg) was dissolved in coupling buffer (20 mL) and the resin was added slowly with gentle shaking. The resin was left shaking overnight at RT, whereupon it was washed with water and washing buffer.

The resin was transferred to blocking buffer (20 mL) and shaken for 2 h. Finally the resin was washed in water, and the resulting resin was suspended in 30% ethanol in Milli-Q water.

---

The invention claimed is:

1. A process for purification of a target biomolecule, comprising: (a) contacting a target biomolecule and, a dual affinity polypeptide in solution to form a binding of the target biomolecule to the dual affinity polypeptide having an equilibrium dissociation constant $K_{D,t}$, (b) subsequently contacting the target biomolecule bound dual affinity polypeptide, and a solid support comprising a catching ligand to form a binding of the dual affinity polypeptide to the solid support having an equilibrium dissociation constant $K_{D,s}$, wherein the ratio between the equilibrium dissociation constants of the dual affinity polypeptide [$K_{D,t}/K_{D,s}$] is at least $10^1$ at standard conditions, and (c) recovering the target biomolecule by elution while the dual affinity polypeptide remains immobilized on the solid support.

2. The process according to claim 1, wherein the solid support is selected from the group comprising solid phase matrices and particles.

3. The process according to claim 1, wherein the dual affinity polypeptide has an equilibrium dissociation constant, $K_{D,t}$ in the range from $10^{-2}$ to $10^{-13}$ M, from $10^{-4}$ to $10^{-13}$ M, or from $10^{-6}$ to $10^{-13}$ M and an equilibrium dissociation constant, $K_{D,s}$ in the range from $10^{-9}$ to $10^{-16}$ M, or the range from $10^{-11}$ to $10^{-16}$ M.

4. The process according to claim 1, wherein the ratio between the equilibrium dissociation constants of the dual affinity polypeptide, [$K_{D,t}/K_{D,s}$], is selected from the group consisting of at least $10^2$, at least $10^3$, and at least $10^4$.

5. The process according to claim 1, wherein elution of the target is accomplished by changing either of pH, ionic strength, or content of chaotropic ions in the solution, or any combinations thereof.

6. The process according to claim 1, wherein the dual affinity polypeptide is a fusion polypeptide.

7. The process according to claim 6, wherein a target biomolecule binding part of the dual affinity polypeptide is selected from the group consisting of protein A, antibodies, antibody fragments, protein A fragments, protein A derived IgG binding domains, lipocalins, and lectins; and a ligand binding part of the dual affinity polypeptide is selected from the group consisting of avidin, streptavidin, neutravidin, steroid receptor, antibody, antibody fragment, lipocalins, lectins, amyloglucosidase, and cellulose binding domains.

8. The process according to claim 7, wherein the antibodies are selected from the group consisting of llama and camel antibodies.

9. The process according to claim 6, wherein the fusion polypeptide is made by fusion of at least one IgG binding domain of protein A or protein A derived IgG binding domain and at least one biotin binding domain of avidin, streptavidin, or neutravidin.

10. The process according to claim 1, wherein the ligand is selected from the group consisting of biotin, acarbose, steroids, hapten, epitope-peptides, dyes, and enzyme inhibitors.

11. The process according to claim 9, wherein the catching ligand attached to the solid support is biotin and the target biomolecule is IgG.

12. The process according to claim 1, wherein the solid support is a solid phase matrix, selected from the group consisting of agar-agar, agaroses, celluloses, cellulose ethers, carboxymethyl cellulose, polyamides, polyvinylalcohols, silicas, and controlled pore glasses.

13. The process according to claim 6, wherein the fusion polypeptide is produced as a recombinant polypeptide in a recombinant host cell.

14. The process according to claim 13, wherein the fusion polypeptide and the target biomolecule is expressed in the same type of host cell.

15. The process according to claim 13, wherein the host cell is selected from the group consisting bacterial cells, fungal cells, mammalian cells, plant cells, and insect cells.

16. The process according to claim 1, wherein the dual affinity polypeptide is chemically fused.

17. A process for purification of a target biomolecule, comprising the steps: (a) contacting a target biomolecule and a dual affinity polypeptide in solution to form a binding of the target biomolecule to the dual affinity polypeptide having an equilibrium dissociation constant $K_{D,t}$, (b) contacting the target biomolecule bound dual affinity polypeptide and a solid support comprising a catching ligand, wherein the dual affinity polypeptide has an equilibrium dissociation constant, $K_{D,t}$ towards the target biomolecule in the range from $10^{-2}$ to $10^{-13}$ M at standard conditions, and wherein binding of the dual affinity polypeptide to the catching ligand on the solid support is provided by cleavage of a para-substituted benzyl guanine resulting in a thioether bond; and (c) recovering the target biomolecule by elution while the dual affinity polypeptide remains immobilized on the solid support.

18. The process of claim 17, wherein the equilibrium dissociation constant, $K_{D,t}$ towards the target biomolecule is in the range from $10^{-4}$ to $10^{-13}$ M.

19. The process of claim 17, wherein the equilibrium dissociation constant, $K_{D,t}$ towards the target biomolecule is in the range from $10^{-6}$ to $10^{-13}$ M.

* * * * *